(12) United States Patent
Winters et al.

(10) Patent No.: US 8,846,949 B2
(45) Date of Patent: Sep. 30, 2014

(54) PYRROLOPYRAZOLES AS N-TYPE CALCIUM CHANNEL BLOCKERS

(71) Applicant: Janssen Pharmaceutica NV, Beerse (BE)

(72) Inventors: Michael Winters, Morgantown, PA (US); Zhihua Sui, Piscataway, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/968,476

(22) Filed: Aug. 16, 2013

(65) Prior Publication Data

US 2014/0051688 A1     Feb. 20, 2014

Related U.S. Application Data

(60) Provisional application No. 61/683,780, filed on Aug. 16, 2012.

(51) Int. Cl.
    *C07D 231/56*      (2006.01)
    *A61K 31/695*      (2006.01)
    *C07D 487/04*      (2006.01)

(52) U.S. Cl.
    CPC .................. *C07D 487/04* (2013.01)
    USPC ........................ 548/360.1; 514/63

(58) Field of Classification Search
    CPC .................................................. C07D 231/54
    See application file for complete search history.

(56) References Cited

FOREIGN PATENT DOCUMENTS

| WO | WO 98/22442 A2 | 5/1998 |
| WO | WO 2004/094429 A1 | 11/2004 |
| WO | WO 2005/073197 A1 | 8/2005 |

OTHER PUBLICATIONS

Subasinghe, N., et al., "A Novel Series of Pyrazolylpiperidine N-Type Calcium Channel Blockers", Bioorganic & Medicinal Chemistry Letters, vol. 22, No. 2, pp. 4080-4083 (2012).
International Search Report for Application No. PCT/US2013/055275 mailed Oct. 21, 2013.

*Primary Examiner* — Heidi Reese
(74) *Attorney, Agent, or Firm* — Peter L. Herridge

(57) ABSTRACT

Disclosed are compounds, compositions and methods for treating various diseases, syndromes, conditions and disorders, including pain. Such compounds are represented by Formula I as follows:

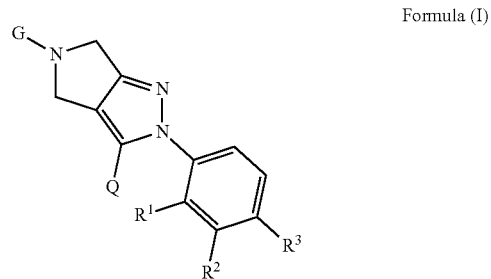

Formula (I)

wherein $R^1$, $R^2$, $R^3$, Q, and G are defined herein.

17 Claims, No Drawings

PYRROLOPYRAZOLES AS N-TYPE CALCIUM CHANNEL BLOCKERS

CROSS REFERENCE TO RELATED APPLICATIONS

This application claims priority of the benefits of the filing of U.S. Provisional Application Ser. No. 61/683,780, filed Aug. 16, 2012. The complete disclosures of the aforementioned related U.S. patent application is/are hereby incorporated herein by reference for all purposes.

STATEMENT REGARDING FEDERALLY SPONSORED RESEARCH OR DEVELOPMENT

The research and development of the invention described below was not federally sponsored.

BACKGROUND OF THE INVENTION

Calcium ions play a fundamental role in the physiology and biochemistry of organisms and of cells. The entry of calcium into cells through ion channels mediates a variety of cellular and physiological responses, including gene expression, signal transduction, neurotransmitter release, muscle contraction and hormone secretion. Ion channels are classified by gating, or what opens and closes the channel to the flux of ions. Voltage-gated ion channels open or close depending on the voltage gradient across the plasma membrane, whereas ligand-gated ion channels open or close depending on the binding of ligands to the channel. The classification of voltage-gated calcium channels divides them into three groups: (i) high voltage-activated channels, which include L-, N-, P- and Q-type channels; (ii) intermediate voltage-activated R-type channels; and (iii) low voltage-activated T-type channels.

The N-type calcium channel is distributed mainly in central and peripheral neurons, being localized primarily to presynaptic nerve terminals. This channel regulates the calcium flux required for depolarization-evoked release of neurotransmitters from synaptic endings. The transmission of pain signals from the periphery to the central nervous system (CNS) is mediated, inter alia, by N-type calcium channels located in the spinal cord. Inhibition of the N-type calcium channel in the superficial dorsal horn leads to a decrease in membrane excitability and neurotransmitter release, resulting in pain relief. In addition, knock-out mice lacking the N-type calcium channel exhibit reduced nociceptive behaviors in animal models of pain.

N-type calcium channels have been shown to mediate the development and maintenance of the neuronal sensitization processes associated with neuropathic pain and therefore provide attractive targets for the development of analgesic drugs. Three N-type calcium channel modulators are currently approved for the treatment of pain: ω-conotoxin MVIIA (ziconotide), marketed as Prialt®, potently and selectively blocks the N-type calcium channel and is indicated for the management of severe chronic pain; gabapentin, marketed as Neurontin®, and pregabalin, marketed as Lyrica®, bind with high affinity to the 2 subunit of the N-type calcium channel and are indicated for the treatment of fibromyalgia, diabetic nerve pain and/or post-herpetic neuralgia pain.

It is an object of the present invention to provide N-Type calcium channel blockers. It is also an object of the invention to provide a method of treating, ameliorating or preventing pain by the administration of a compound of Formula (I). And, it is an object of the invention to provide a pharmaceutical composition comprising a compound of Formula (I), useful for treating, ameliorating or preventing pain.

SUMMARY OF THE INVENTION

The present invention is directed to a compound of Formula (I)

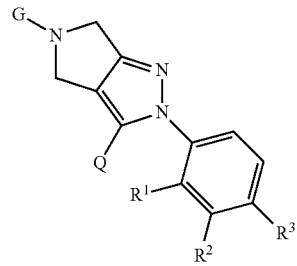

Formula (I)

wherein
$R^1$ is selected from the group consisting of $C_{1-4}$alkyl, $C_{1-4}$alkoxy, 2,2-difluoroethoxy, di($C_{1-4}$alkyl)amino, trifluoromethoxy, fluoro, and trifluoromethyl;
$R^2$ is hydrogen; or, $R^2$ may be taken with $R^1$ and the phenyl ring to which $R^1$ and $R^2$ are both attached to form 2,3-dihydrobenzofuran-7-yl or 1,3-benzodioxol-4-yl;
$R^3$ is hydrogen, methyl, methoxy, chloro, or fluoro;
Q is selected from the group consisting of Q1, Q2, and Q3;

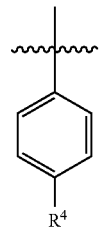

Q1

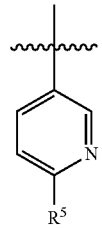

Q2

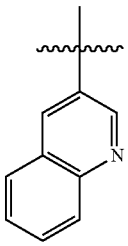

Q3 wherein
$R^4$ is selected from the group consisting of hydrogen, $C_{1-4}$alkyl, $C_{1-4}$alkoxy, cyano, fluoro, and chloro;
$R^5$ is independently selected from the group consisting of hydrogen, $C_{1-4}$alkyl, $C_{1-4}$alkoxy, cyano, chloro, and di($C_{1-4}$alkyl)amino;

G is selected from the group consisting of 4-methylphenyl, 3-cyanophenyl, 4-cyanophenyl, 4-methoxycarbonylphenyl, 2-chloro-quinolin-6-yl, morpholin-4-ylsulfonyl, morpholin-4-yl($C_{1-4}$alkyl)aminosulfonyl, 2,6-dimethylmorpholin-4-ylsulfonyl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, $C_{1-4}$alkoxycarbonyl($C_{1-4}$)alkyl-sulfonyl, trifluoromethylsulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$)alkyl-sulfonyl, $C_{1-4}$alkylsulfonylamino($C_{1-4}$)alkyl-sulfonyl, 2,5-dione-pyrrolidin-1-yl-($C_{1-4}$)alkyl-sulfonyl, (2H)-1,3-dione-1H-isoindol-1-yl-($C_{1-4}$)alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-($R^6$)-piperidin-1-ylsulfonyl wherein $R^6$ is $C_{1-4}$alkoxycarbonyl or $C_{1-4}$alkyl; azepan-1-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, trifluoromethylsulfonylaminomethylcarbonyl, trifluoromethoxycarbonyl, $C_{1-4}$alkylsulfonylaminomethyl-carbonyl, $C_{1-4}$alkoxycarbonyl, di($C_{1-4}$alkyl)aminocarbonyl, $C_{1-4}$alkoxycarbonyl, pyridinylcarbonyl, furanylcarbonyl, and 5-methylisoxazol-3-ylcarbonyl;

and enantiomers, diastereomers, solvates and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (I), or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a N-Type calcium channel-modulated disorder in a subject, including a human or other mammal in which the disease, syndrome, or condition is affected by the modulation of the N-Type calcium channel, such as pain and the diseases that lead to such pain, using a compound of Formula (I).

The present invention also provides, inter alia, methods for producing the instant compounds and pharmaceutical compositions and medicaments thereof.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g. $C_{1-8}$) refer independently to the number of carbon atoms in an alkyl moiety or to the alkyl portion of a larger alkyl-containing substituent. In substituent groups with multiple alkyl groups such as ($C_{1-6}$alkyl)$_2$-amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members and which contains carbon atoms and from 1 to 4 heteroatoms independently selected from the group consisting of N, O, and S. Included within the term heterocyclyl is a nonaromatic cyclic ring of 5 to 7 members in which 1 to 2 members are nitrogen, or a nonaromatic cyclic ring of 5 to 7 members in which 0, 1 or 2 members are nitrogen and up to 2 members are oxygen or sulfur and at least one member must be either nitrogen, oxygen or sulfur; wherein, optionally, the ring contains zero to one unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine.

The term "formyl" refers to the group —C(═O)H.

The term "oxo" refers to the group (═O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

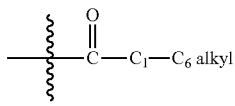

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "N-Type calcium channel blocker" is intended to encompass a compound that interacts with the N-Type calcium channel to substantially reduce or eliminate its functional activity, thereby decreasing the flow of calcium ions through the channel and the rise of intracellular calcium concentrations.

The term "N-Type calcium channel-modulated" is used to refer to the condition of being affected by the modulation of the N-Type calcium channel, including the condition of being affected by the inhibition of the N-Type calcium channel, such as, for example, pain, the diseases that lead to such pain and treatments that lead to the reduction of such pain.

As used herein, unless otherwise noted, the term "affect" or "affected" (when referring to a disease, syndrome, condition or disorder that is affected by the inhibition of N-Type calcium channel) shall include a reduction in the frequency and/or severity of one or more symptoms or manifestations of said disease, syndrome, condition or disorder and/or include the prevention of the development of one or more symptoms or manifestations of said disease, syndrome, condition or disorder or the development of the disease, condition, syndrome or disorder.

The compounds of Formula (I) are useful in methods for treating, ameliorating and/or preventing a disease, a syndrome, a condition or a disorder that is affected by the inhibition of N-Type calcium channel. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt form thereof. In particular, the compounds of Formula (I) are useful for treating, ameliorating and/or preventing pain as well as diseases, syndromes, conditions or disorders causing such pain. More particularly, the compounds of Formula (I) are useful for treating, ameliorating and/or preventing acute pain, inflammatory pain and/or neuropathic pain, comprising administering to a subject in need thereof a therapeutically effective amount of a compound of Formula (I), as herein defined.

Acute pain, as used herein, refers to pain that comes on quickly, can be of varying severity but is self-limiting and of relatively short duration. Examples of acute pain include, but are not limited to, post-operative pain, post-surgical pain, toothache, burn, sunburn, insect/animal bites and stings, headache and/or any pain associated with acute trauma or injury.

Inflammatory pain refers to pain arising from an inflammatory disease, condition, syndrome or disorder, including but not limited to inflammatory bowel disease, irritable bowel syndrome, visceral pain, migraine, post-operative pain, osteoarthritis, rheumatoid arthritis, back pain, low back pain, joint pain, abdominal pain, chest pain, labor pain, musculoskeletal diseases, skin diseases, toothache, pyresis, burn, sunburn, snake bite, venomous snake bite, spider bite, insect sting, neurogenic or overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, post-mastectomy pain syndrome, menstrual pain, endometriosis, pain due to physical trauma, headache, sinus headache, tension headache or arachnoiditis.

A further embodiment of the present invention is directed to a method for treating, ameliorating and/or preventing neuropathic pain. Neuropathic pain refers to a disease, syndrome, condition and/or disorder involving damage to the peripheral or central nervous system, including cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, post-herpetic neuralgia, causalgia, red neuralgia, Sluder's neuralgia, splenopalatine neuralgia, supraorbital neuralgia, trigeminal neuralgia, vulvodynia, or vidian neuralgia.

Embodiments of the present invention include a compound of Formula (I)

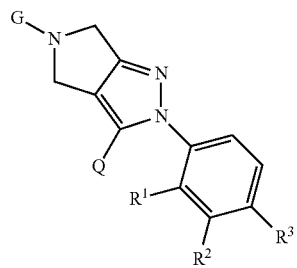

Formula (I)

wherein
a) $R^1$ is selected from the group consisting of $C_{1-4}$alkyl, $C_{1-4}$alkoxy, 2,2-difluoroethoxy, di($C_{1-4}$alkyl)amino, and trifluoromethoxy;
b) $R^1$ is selected from the group consisting of ethyl, methoxy, ethoxy, isopropyloxy, difluoroethoxy, dimethylamino, and trifluoromethoxy;
c) $R^3$ is hydrogen, methyl, chloro, or fluoro;
d) Q is selected from the group consisting of Q1, Q2, and Q3;

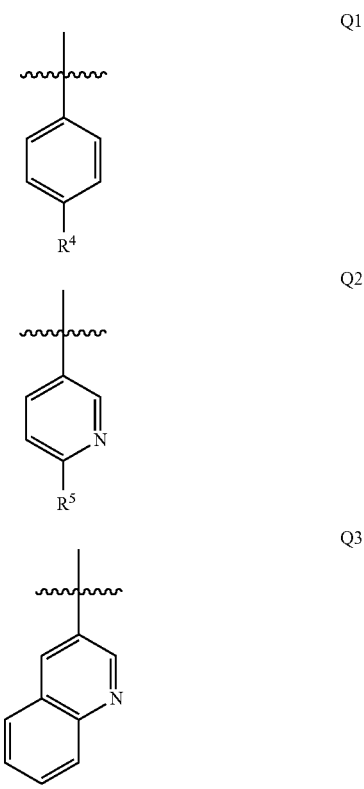

wherein
$R^4$ is chloro;
$R^5$ is independently selected from the group consisting of $C_{1-4}$alkyl, $C_{1-4}$alkoxy, and chloro;
e) Q is selected from the group consisting of Q1, Q2, and Q3;

-continued

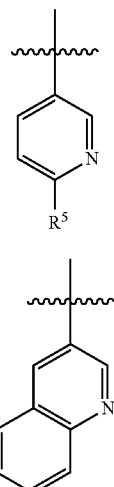

wherein
R⁴ is chloro;
R⁵ is independently selected from the group consisting of $C_{1-4}$alkoxy and chloro;

f) G is selected from the group consisting of 4-methylphenyl, 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, trifluoromethylsulfonyl, $C_{1-4}$alkoxycarbonyl($C_{1-4}$alkyl-sulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkyl-sulfonyl, $C_{1-4}$alkylsulfonylamino($C_{1-4}$)alkyl-sulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R⁶)-piperidin-1-ylsulfonyl wherein R⁶ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, $C_{1-4}$alkylsulfonylaminomethyl-carbonyl, $C_{1-4}$alkoxycarbonyl, di($C_{1-4}$alkyl)aminocarbonyl, $C_{1-4}$alkoxycarbonyl, pyridinylcarbonyl, and furanylcarbonyl;

g) G is selected from the group consisting of methylphenyl, 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, 4-$C_{1-4}$alkoxycarbonyl($C_{1-4}$alkyl-sulfonyl, trifluoromethylsulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkylsulfonyl, $C_{1-4}$alkylsulfonylamino($C_{1-4}$alkyl-sulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R⁶)-piperidin-1-ylsulfonyl wherein R⁶ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonyl-aminomethyl-carbonyl, $C_{1-4}$alkoxycarbonyl, di($C_{1-4}$alkyl)aminocarbonyl, $C_{1-4}$alkoxycarbonyl, and pyridinylcarbonyl;

h) G is selected from the group consisting of 2-chloro-quinolin-6-yl, $C_{6-10}$aryl($C_{1-4}$)alkylsulfonyl, $C_{6-10}$aryloxy($C_{1-4}$alkylsulfonyl, 3,5-dimethylisoxazol-4-yl-sulfonyl, $C_{1-4}$alkoxycarbonyl($C_{1-4}$alkyl-sulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkyl-sulfonyl, $C_{1-4}$alkylsulfonylamino($C_{1-4}$)alkyl-sulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R⁶)-piperidin-1-ylsulfonyl wherein R⁶ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, $C_{1-4}$alkoxycarbonylamino($C_{2-4}$)alkylcarbonyl, and $C_{1-4}$alkoxycarbonyl;

and any combination of embodiments a) through h) above, provided that it is understood that combinations in which different embodiments of the same substituent would be combined are excluded;

and enantiomers, diastereomers, solvates and pharmaceutically acceptable salts thereof.

An embodiment of the present invention is directed to a compound of Formula (I)

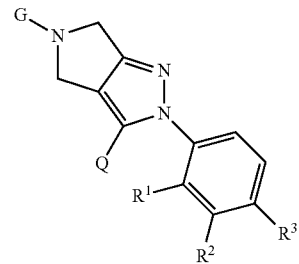

Formula (I)

wherein
R¹ is selected from the group consisting of $C_{1-4}$alkyl, $C_{1-4}$alkoxy, 2,2-difluoroethoxy, di($C_{1-4}$alkyl)amino, trifluoromethoxy, fluoro, and trifluoromethyl;

R² is hydrogen; or, R² may be taken with R¹ and the phenyl ring to which R¹ and R² are both attached to form 2,3-dihydrobenzofuran-7-yl or 1,3-benzodioxol-4-yl;

R³ is hydrogen, methyl, methoxy, chloro, or fluoro;

Q is selected from the group consisting of Q1, Q2, and Q3;

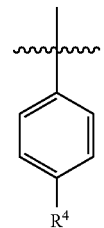

Q1

-continued

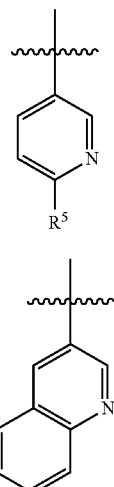

Q2

Q3 wherein
R[4] is selected from the group consisting of chloro;
R[5] is independently selected from the group consisting of $C_{1-4}$alkoxy and chloro;
G is selected from the group consisting of 4-methylphenyl, 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, trifluoromethylsulfonyl, $C_{1-4}$alkoxycarbonyl($C_{1-4}$)alkyl-sulfonyl, $C_{3-7}$cycloalkylsulfonyl, 2,2,2-trifluoroethyl-sulfonyl, di($C_{1-4}$alkyl)aminosulfonyl, di($C_{1-4}$-alkyl)aminosulfonylamino($C_{1-4}$alkyl-sulfonyl, $C_{1-4}$alkylsulfonylamino($C_{1-4}$alkylsulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R[6])-piperidin-1-ylsulfonyl wherein R[6] is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, $C_{1-4}$alkylsulfonylaminomethyl-carbonyl, $C_{1-4}$alkoxycarbonyl, di($C_{1-4}$alkyl)aminocarbonyl, $C_{1-4}$alkoxycarbonyl, pyridinylcarbonyl, and furanylcarbonyl;
and enantiomers, diastereomers, solvates and pharmaceutically acceptable salts thereof.

An embodiment of the present invention is directed to a compound of Formula (I)

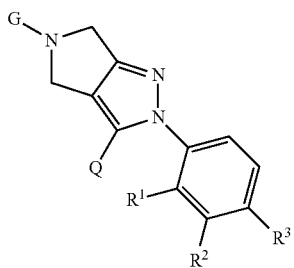

Formula (I)

wherein
R[1] is selected from the group consisting of $C_{1-4}$alkyl, $C_{1-4}$alkoxy, 2,2-difluoroethoxy, di($C_{1-4}$alkyl)amino, trifluoromethoxy, fluoro, and trifluoromethyl;

R[2] is hydrogen; or, R[2] may be taken with R[1] and the phenyl ring to which R[1] and R[2] are both attached to form 2,3-dihydrobenzofuran-7-yl or 1,3-benzodioxol-4-yl;
R[3] is hydrogen, methyl, methoxy, chloro, or fluoro;
Q is selected from the group consisting of Q1, Q2, and Q3;

Q1

Q2

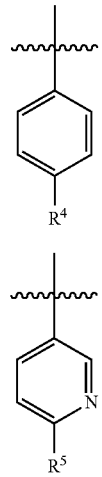

Q3 wherein
R[4] is chloro;
R[5] is independently selected from the group consisting of $C_{1-4}$alkoxy and chloro;
G is selected from the group consisting of methylphenyl, 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, 4-$C_{1-4}$alkoxycarbonyl($C_{1-4}$)alkyl-sulfonyl, trifluoromethylsulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkyl-sulfonyl, $C_{1-4}$alkylsulfonylamino($C_{1-4}$alkyl-sulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R[6])-piperidin-1-ylsulfonyl wherein R[6] is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, $C_{1-4}$alkoxycarbonyl, di($C_{1-4}$alkyl)aminocarbonyl, $C_{1-4}$alkoxycarbonyl, and pyridinylcarbonyl;
and enantiomers, diastereomers, solvates and pharmaceutically acceptable salts thereof.

An embodiment of the present invention is directed to a compound of Formula (I)

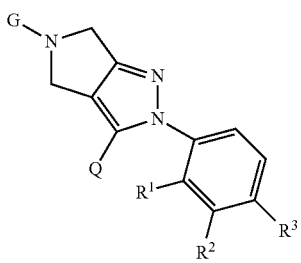

Formula (I)

wherein
R¹ is selected from the group consisting of ethyl, methoxy, ethoxy, isopropyloxy, difluoroethoxy, dimethylamino, and trifluoromethoxy;

R² is hydrogen; or, R² may be taken with R¹ and the phenyl ring to which R¹ and R² are both attached to form 2,3-dihydrobenzofuran-7-yl or 1,3-benzodioxol-4-yl;

R³ is hydrogen, methyl, chloro, or fluoro;

Q is selected from the group consisting of Q1, Q2, and Q3;

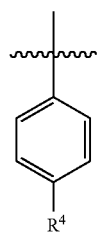

Q1

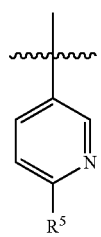

Q2

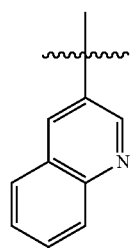

Q3 wherein
R⁴ is chloro;
R⁵ is independently selected from the group consisting of $C_{1-4}$alkoxy and chloro;
G is selected from the group consisting of 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, $C_{1-4}$alkoxycarbonyl($C_{1-4}$alkyl-sulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkyl-sulfonyl, $C_{1-4}$alkylsulfonylamino($C_{1-4}$)alkyl-sulfonyl, 2,5-dione-pyrrolidin-1-yl-($C_{1-4}$)alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R⁶)-piperidin-1-ylsulfonyl wherein R⁶ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, $C_{1-4}$alkoxycarbonylamino($C_{2-4}$)alkyl-carbonyl, and $C_{1-4}$alkoxycarbonyl;

and enantiomers, diastereomers, solvates and pharmaceutically acceptable salts thereof.

An embodiment of the present invention is directed to a compound of Formula (I)

Formula (I)

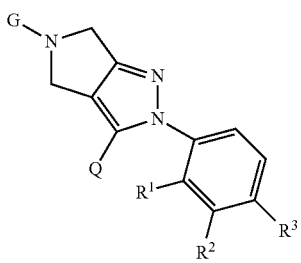

wherein
R¹ is selected from the group consisting of ethyl, methoxy, ethoxy, isopropyloxy, difluoroethoxy, dimethylamino, and trifluoromethoxy;

R² is hydrogen;

R³ is hydrogen, methyl, chloro, or fluoro;

Q is selected from the group consisting of Q1, Q2, and Q3;

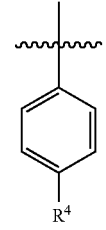

Q1

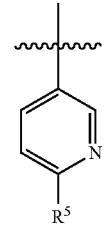

Q2

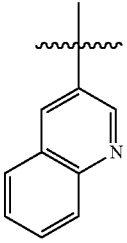

Q3 wherein
R⁴ is chloro;
R⁵ is independently selected from the group consisting of $C_{1-4}$alkoxy and chloro;

G is selected from the group consisting of 2-chloro-quinolin-6-yl, $C_{6-10}$aryl($C_{1-4}$)alkylsulfonyl, $C_{6-10}$aryloxy($C_{1-4}$) alkylsulfonyl, 3,5-dimethylisoxazol-4-yl-sulfonyl, $C_{1-4}$alkoxycarbonyl($C_{1-4}$alkyl-sulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkyl-sulfonyl, $C_{1-4}$alkylsulfonylamino($C_{1-4}$alkyl-sulfonyl, 2,5-dione-pyrrolidin-1-yl-($C_{1-4}$alkyl-sulfonyl, (2H)-1,3-dione-1H-isoindol-1-yl-($C_{1-4}$)alkyl-sulfonyl, 1,1-dioxidotetrahydrothiophen-3-yl)sulfonyl, $C_{1-6}$alkylsulfonyl, di($C_{1-4}$alkyl) aminosulfonyl, pyrrolidin-1-ylsulfonyl, piperidin-1-ylsulfonyl, 4-($R^6$)-piperidin-1-ylsulfonyl wherein $R^6$ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, $C_{1-4}$alkoxycarbonylamino($C_{2-4}$)alkyl-carbonyl, and $C_{1-4}$alkoxycarbonyl;

and enantiomers, diastereomers, solvates and pharmaceutically acceptable salts thereof.

Further embodiments of the present invention are directed to a compound of Formula (I)

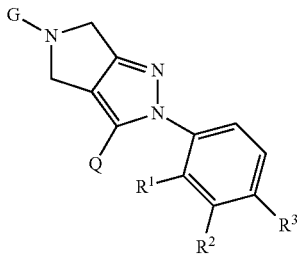

Formula (I)

selected from the group consisting of

Cpd 1, tert-Butyl 3-(4-chlorophenyl)-2-(2-ethylphenyl)-2,6-dihydropyrrolo[3,4-c]pyrazole-5(4H)-carboxylate;

Cpd 2, 3-(4-Chlorophenyl)-2-(2-ethylphenyl)-5-(methylsulfonyl)-2,4,5,6-tetrahydropyrrolo[3,4-c]pyrazole;

Cpd 3, 3-(4-Chlorophenyl)-2-(2-ethylphenyl)-5-[(trifluoromethyl)sulfonyl]-2,4,5,6-tetrahydropyrrolo[3,4-c]pyrazole;

Cpd 4, 3-(4-Chlorophenyl)-2-(2-ethylphenyl)-5-(pyridin-3-ylcarbonyl)-2,4,5,6-tetrahydropyrrolo[3,4-c]pyrazole;

Cpd 5, 3-(4-Chlorophenyl)-2-(2-ethylphenyl)-5-(pyridin-4-ylcarbonyl)-2,4,5,6-tetrahydropyrrolo[3,4-c]pyrazole;

Cpd 6, 3-(4-Chlorophenyl)-2-(2-ethylphenyl)-5-(trifluoroacetyl)-2,4,5,6-tetrahydropyrrolo[3,4-c]pyrazole;

Cpd 7, 3-(4-Chlorophenyl)-2-(2-ethylphenyl)-5-(pyridin-2-ylcarbonyl)-2,4,5,6-tetrahydropyrrolo[3,4-c]pyrazole;

Cpd 8, 3-(4-Chlorophenyl)-2-(2-ethylphenyl)-5-(furan-2-ylcarbonyl)-2,4,5,6-tetrahydropyrrolo[3,4-c]pyrazole;

Cpd 9, 3-(4-Chlorophenyl)-2-(2-ethylphenyl)-5-[(5-methylisoxazol-3-yl)carbonyl]-2,4,5,6-tetrahydropyrrolo[3,4-c]pyrazole;

Cpd 10, 3-(4-Chlorophenyl)-2-(2-ethylphenyl)-5-(methoxyacetyl)-2,4,5,6-tetrahydropyrrolo[3,4-c]pyrazole;

Cpd 11, tert-Butyl{2-[3-(4-chlorophenyl)-2-(2-ethylphenyl)-2,6-dihydropyrrolo[3,4-c]pyrazol-5 (4H)-yl]-2-oxo ethyl}carbamate;

Cpd 12, N-{2-[3-(4-Chlorophenyl)-2-(2-ethylphenyl)-2,6-dihydropyrrolo[3,4-c]pyrazol-5(4H)-yl]-2-oxoethyl}methanesulfonamide;

Cpd 13, N-{2-[3-(4-Chlorophenyl)-2-(2-ethylphenyl)-2,6-dihydropyrrolo[3,4-c]pyrazol-5(4H)-yl]-2-oxoethyl}-1,1,1-trifluoromethanesulfonamide;

Cpd 14, tert-Butyl 3-(4-chlorophenyl)-2-[2-(trifluoromethyl)phenyl]-2,6-dihydropyrrolo[3,4-c]pyrazole-5(4H)-carboxylate;

Cpd 15, 3-(4-Chlorophenyl)-5-(methylsulfonyl)-2-[2-(trifluoromethyl)phenyl]-2,4,5,6-tetrahydropyrrolo[3,4-c]pyrazole;

Cpd 16, 3-(4-Chlorophenyl)-5-[(1-methylethyl)sulfonyl]-2-[2-(trifluoromethyl)phenyl]-2,4,5,6-tetrahydropyrrolo[3,4-c]pyrazole;

Cpd 17, 3-(4-Chlorophenyl)-5-[(4-methylphenyl)sulfonyl]-2-[2-(trifluoromethyl)phenyl]-2,4,5,6-tetrahydropyrrolo[3,4-c]pyrazole;

Cpd 18, tert-Butyl{2-[3-(4-chlorophenyl)-2-[2-(trifluoromethyl)phenyl]-2,6-dihydropyrrolo[3,4-c]pyrazol-5(4H)-yl]-2-oxo ethyl}carbamate;

Cpd 19, tert-Butyl 3-(4-chlorophenyl)-2-[2-(trifluoromethoxy)phenyl]-2,6-dihydropyrrolo[3,4-c]pyrazole-5(4H)-carboxylate;

Cpd 20, 3-(4-Chlorophenyl)-5-(methylsulfonyl)-2-[2-(trifluoromethoxy)phenyl]-2,4,5,6-tetrahydropyrrolo[3,4-c]pyrazole;

Cpd 21, 3-(4-Chlorophenyl)-5-(trifluoroacetyl)-2-[2-(trifluoromethoxy)phenyl]-2,4,5,6-tetrahydropyrrolo[3,4-c]pyrazole;

Cpd 22, tert-Butyl{2-[3-(4-chlorophenyl)-2-[2-(trifluoromethoxy)phenyl]-2,6-dihydropyrrolo[3,4-c]pyrazol-5(4H)-yl]-2-oxo ethyl}carbamate;

Cpd 23, 3-[3-(4-Chlorophenyl)-2-[2-(trifluoromethoxy)phenyl]-2,6-dihydropyrrolo[3,4-c]pyrazol-5(4H)-yl]benzonitrile;

Cpd 24, Methyl 4-[3-(4-chlorophenyl)-2-[2-(trifluoromethoxy)phenyl]-2,6-dihydropyrrolo[3,4-c]pyrazol-5(4H)-yl]benzoate;

Cpd 25, 4-[3-(4-Chlorophenyl)-2-[2-(trifluoromethoxy)phenyl]-2,6-dihydropyrrolo[3,4-c]pyrazol-5(4H)-yl]benzonitrile;

Cpd 26, 4-[3-(4-Chlorophenyl)-2-[2-(trifluoromethoxy)phenyl]-2,6-dihydropyrrolo[3,4-c]pyrazol-5(4H)-yl]-N-(2-morpholin-4-ylethyl)benzenesulfonamide;

Cpd 27, 2-Chloro-6-[3-(4-chlorophenyl)-2-[2-(trifluoromethoxy)phenyl]-2,6-dihydropyrrolo[3,4-c]pyrazol-5(4H)-yl]quinoline;

Cpd 28, tert-Butyl 3-(4-chlorophenyl)-2-(2-methoxyphenyl)-2,6-dihydropyrrolo[3,4-c]pyrazole-5(4H)-carboxylate;

Cpd 29, tert-Butyl{2-[3-(4-chlorophenyl)-2-(2-methoxyphenyl)-2,6-dihydropyrrolo[3,4-c]pyrazol-5(4H)-yl]-2-oxoethyl}carbamate;

Cpd 30, 3-(4-Chlorophenyl)-2-(2-methoxyphenyl)-5-(methylsulfonyl)-2,4,5,6-tetrahydropyrrolo[3,4-c]pyrazole;

Cpd 31, 3-(4-Chlorophenyl)-2-(2-methoxyphenyl)-5-[(1-methylethyl)sulfonyl]-2,4,5,6-tetrahydropyrrolo[3,4-c]pyrazole;

Cpd 32, 3-(4-Chlorophenyl)-5-(cyclopropylsulfonyl)-2-(2-methoxyphenyl)-2,4,5,6-tetrahydropyrrolo[3,4-c]pyrazole;

Cpd 33, 3-(4-Chlorophenyl)-2-(2-methoxyphenyl)-N,N-dimethyl-2,6-dihydropyrrolo[3,4-c]pyrazole-5(4H)-sulfonamide;

Cpd 34, 3-(4-Chlorophenyl)-2-(2-methoxyphenyl)-N,N-dimethyl-2,6-dihydropyrrolo[3,4-c]pyrazole-5(4H)-carboxamide;

Cpd 35, 3-(4-Chlorophenyl)-5-[(1-methylethyl)sulfonyl]-2-[2-(trifluoromethoxy)phenyl]-2,4,5,6-tetrahydropyrrolo[3,4-c]pyrazole;

Cpd 36, 3-(4-Chlorophenyl)-2-(2-methoxyphenyl)-5-[(2,2,2-trifluoroethyl)sulfonyl]-2,4,5,6-tetrahydropyrrolo[3,4-c]pyrazole;

Cpd 37, 3-(4-Chlorophenyl)-5-(cyclohexylsulfonyl)-2-(2-methoxyphenyl)-2,4,5,6-tetrahydropyrrolo[3,4-c]pyrazole;

Cpd 38, 2-(2-{[3-(4-Chlorophenyl)-2-(2-methoxyphenyl)-2,6-dihydropyrrolo[3,4-c]pyrazol-5(4H)-yl]sulfonyl}ethyl)-1H-isoindole-1,3(2H)-dione;

Cpd 39, 5-(Benzylsulfonyl)-3-(4-chlorophenyl)-2-(2-methoxyphenyl)-2,4,5,6-tetrahydropyrrolo[3,4-c]pyrazole;

Cpd 40, 3-(4-Chlorophenyl)-5-(cyclopentylsulfonyl)-2-(2-methoxyphenyl)-2,4,5,6-tetrahydropyrrolo[3,4-c]pyrazole;

Cpd 41, 3-(4-Chlorophenyl)-2-(2-methoxyphenyl)-5-[(1-methylbutyl)sulfonyl]-2,4,5,6-tetrahydropyrrolo[3,4-c]pyrazole;

Cpd 42, 1-(2-{[3-(4-Chlorophenyl)-2-(2-methoxyphenyl)-2,6-dihydropyrrolo[3,4-c]pyrazol-5(4H)-yl]sulfonyl}ethyl)pyrrolidine-2,5-dione;

Cpd 43, 3-(4-Chlorophenyl)-2-(2-methoxyphenyl)-5-[(2-phenoxyethyl)sulfonyl]-2,4,5,6-tetrahydropyrrolo[3,4-c]pyrazole;

Cpd 44, N-(2-{[3-(4-Chlorophenyl)-2-(2-methoxyphenyl)-2,6-dihydropyrrolo[3,4-c]pyrazol-5(4H)-yl]sulfonyl}ethyl)methanesulfonamide;

Cpd 45, N-(2-{[3-(4-Chlorophenyl)-2-(2-methoxyphenyl)-2,6-dihydropyrrolo[3,4-c]pyrazol-5(4H)-yl]sulfonyl}ethyl)propane-2-sulfonamide;

Cpd 46, N'-(2-{[3-(4-Chlorophenyl)-2-(2-methoxyphenyl)-2,6-dihydropyrrolo[3,4-c]pyrazol-5(4H)-yl]sulfonyl}ethyl)-N,N-dimethylsulfamide;

Cpd 47, Methyl 3-{[3-(4-chlorophenyl)-2-[2-(trifluoromethoxy)phenyl]-2,6-dihydropyrrolo[3,4-c]pyrazol-5(4H)-yl]sulfonyl}propanoate;

Cpd 48, 3-(4-Chlorophenyl)-5-[(1,1-dioxidotetrahydrothiophen-3-yl)sulfonyl]-2-[2-(trifluoromethoxy)phenyl]-2,4,5,6-tetrahydropyrrolo[3,4-c]pyrazole;

Cpd 49, 3-(4-Chlorophenyl)-2-(2-ethoxyphenyl)-5-(methylsulfonyl)-2,4,5,6-tetrahydropyrrolo[3,4-c]pyrazole;

Cpd 50, 3-(4-Chlorophenyl)-2-(2-ethoxyphenyl)-5-[(1-methylethyl)sulfonyl]-2,4,5,6-tetrahydropyrrolo[3,4-c]pyrazole;

Cpd 51, 3-(4-Chlorophenyl)-5-(cyclopentylsulfonyl)-2-(2-ethoxyphenyl)-2,4,5,6-tetrahydropyrrolo[3,4-c]pyrazole;

Cpd 52, 3-(4-Chlorophenyl)-5-(cyclohexylsulfonyl)-2-(2-ethoxyphenyl)-2,4,5,6-tetrahydropyrrolo[3,4-c]pyrazole;

Cpd 53, 5-(Benzylsulfonyl)-3-(4-chlorophenyl)-2-(2-ethoxyphenyl)-2,4,5,6-tetrahydropyrrolo[3,4-c]pyrazole;

Cpd 54, 3-(4-Chlorophenyl)-2-(2-ethoxyphenyl)-N,N-dimethyl-2,6-dihydropyrrolo[3,4-c]pyrazole-5(4H)-sulfonamide;

Cpd 55, 5-(Azepan-1-ylsulfonyl)-3-(4-chlorophenyl)-2-(2-methoxyphenyl)-2,4,5,6-tetrahydropyrrolo[3,4-c]pyrazole;

Cpd 56, 3-(4-Chlorophenyl)-N,N-diethyl-2-(2-methoxyphenyl)-2,6-dihydropyrrolo[3,4-c]pyrazole-5(4H)-sulfonamide;

Cpd 57, 3-(4-Chlorophenyl)-2-(2-methoxyphenyl)-5-[(4-methylpiperidin-1-yl)sulfonyl]-2,4,5,6-tetrahydropyrrolo[3,4-c]pyrazole;

Cpd 58, Methyl 1-{[3-(4-chlorophenyl)-2-(2-methoxyphenyl)-2,6-dihydropyrrolo[3,4-c]pyrazol-5(4H)-yl]sulfonyl}piperidine-4-carboxylate;

Cpd 59, 3-(4-Chlorophenyl)-2-(2-methoxyphenyl)-5-(morpholin-4-ylsulfonyl)-2,4,5,6-tetrahydropyrrolo[3,4-c]pyrazole;

Cpd 60, 3-(4-Chlorophenyl)-2-(2-methoxyphenyl)-5-(pyrrolidin-1-ylsulfonyl)-2,4,5,6-tetrahydropyrrolo[3,4-c]pyrazole;

Cpd 61, 3-(4-Chlorophenyl)-5-{[(2S,6S)-2,6-dimethylmorpholin-4-yl]sulfonyl}-2-(2-methoxyphenyl)-2,4,5,6-tetrahydropyrrolo[3,4-c]pyrazole;

Cpd 62, 3-(4-Chlorophenyl)-2-(2-methoxyphenyl)-5-(piperidin-1-ylsulfonyl)-2,4,5,6-tetrahydropyrrolo[3,4-c]pyrazole;

Cpd 63, 3-(4-Chlorophenyl)-N,N-dimethyl-2-[2-(1-methylethoxy)phenyl]-2,6-dihydropyrrolo[3,4-c]pyrazole-5(4H)-sulfonamide;

Cpd 64, 2-(4-Chloro-2-methoxyphenyl)-3-(4-chlorophenyl)-5-[(1-methylethyl)sulfonyl]-2,4,5,6-tetrahydropyrrolo[3,4-c]pyrazole;

Cpd 65, 2-(4-Chloro-2-methoxyphenyl)-3-(4-chlorophenyl)-N,N-dimethyl-2,6-dihydropyrrolo[3,4-c]pyrazole-5(4H)-sulfonamide;

Cpd 66, 3-(4-Chlorophenyl)-2-(4-methoxy-2-methylphenyl)-5-(methylsulfonyl)-2,4,5,6-tetrahydropyrrolo[3,4-c]pyrazole;

Cpd 67, 3-(4-Chlorophenyl)-2-(4-methoxy-2-methylphenyl)-5-[(1-methylethyl)sulfonyl]-2,4,5,6-tetrahydropyrrolo[3,4-c]pyrazole;

Cpd 68, 3-(4-Chlorophenyl)-5-(cyclohexylsulfonyl)-2-(4-methoxy-2-methylphenyl)-2,4,5,6-tetrahydropyrrolo[3,4-c]pyrazole;

Cpd 69, 3-(4-Chlorophenyl)-2-(4-methoxy-2-methylphenyl)-N,N-dimethyl-2,6-dihydropyrrolo[3,4-c]pyrazole-5(4H)-sulfonamide;

Cpd 70, 3-(4-Chlorophenyl)-2-(4-fluoro-2-methoxyphenyl)-5-(methylsulfonyl)-2,4,5,6-tetrahydropyrrolo[3,4-c]pyrazole;

Cpd 71, 3-(4-Chlorophenyl)-2-(4-fluoro-2-methoxyphenyl)-5-[(1-methylethyl)sulfonyl]-2,4,5,6-tetrahydropyrrolo[3,4-c]pyrazole;

Cpd 72, 3-(4-Chlorophenyl)-5-(cyclohexylsulfonyl)-2-(4-fluoro-2-methoxyphenyl)-2,4,5,6-tetrahydropyrrolo[3,4-c]pyrazole;

Cpd 73, 3-(4-Chlorophenyl)-2-(4-fluoro-2-methoxyphenyl)-5-[(4-methylpiperidin-1-yl)sulfonyl]-2,4,5,6-tetrahydropyrrolo[3,4-c]pyrazole;

Cpd 74, 3-(4-Chlorophenyl)-2-(2-methoxy-4-methylphenyl)-5-(methylsulfonyl)-2,4,5,6-tetrahydropyrrolo[3,4-c]pyrazole;

Cpd 75, 3-(4-Chlorophenyl)-2-(2-methoxy-4-methylphenyl)-5-[(1-methylethyl)sulfonyl]-2,4,5,6-tetrahydropyrrolo[3,4-c]pyrazole;

Cpd 76, 3-(4-Chlorophenyl)-2-(2-methoxy-4-methylphenyl)-5-[(1-methylbutyl)sulfonyl]-2,4,5,6-tetrahydropyrrolo[3,4-c]pyrazole;

Cpd 77, 3-(4-Chlorophenyl)-2-(2-methoxy-4-methylphenyl)-5-[(4-methylpiperidin-1-yl)sulfonyl]-2,4,5,6-tetrahydropyrrolo[3,4-c]pyrazole;

Cpd 78, 3-(4-Chlorophenyl)-2-(2-fluoro-4-methoxyphenyl)-5-(methylsulfonyl)-2,4,5,6-tetrahydropyrrolo[3,4-c]pyrazole;

Cpd 79, 3-(4-Chlorophenyl)-2-(2-fluoro-4-methoxyphenyl)-5-[(1-methylethyl)sulfonyl]-2,4,5,6-tetrahydropyrrolo[3,4-c]pyrazole;

Cpd 80, 3-(4-Chlorophenyl)-2-(2-fluoro-4-methoxyphenyl)-5-[(4-methylpiperidin-1-yl)sulfonyl]-2,4,5,6-tetrahydropyrrolo[3,4-c]pyrazole;

Cpd 81, 2-(1,3-Benzodioxol-4-yl)-3-(4-chlorophenyl)-5-[(1-methylethyl)sulfonyl]-2,4,5,6-tetrahydropyrrolo[3,4-c]pyrazole;

Cpd 82, 2-(1,3-Benzodioxol-4-yl)-3-(4-chlorophenyl)-5-[(2-methylpropyl)sulfonyl]-2,4,5,6-tetrahydropyrrolo[3,4-c]pyrazole;

Cpd 83, 2-(1,3-Benzodioxol-4-yl)-3-(4-chlorophenyl)-5-[(4-methylpiperidin-1-yl)sulfonyl]-2,4,5,6-tetrahydropyrrolo[3,4-c]pyrazole;

Cpd 84, 3-(4-Chlorophenyl)-2-(2,3-dihydro-1-benzofuran-7-yl)-5-[(1-methylethyl)sulfonyl]-2,4,5,6-tetrahydropyrrolo[3,4-c]pyrazole;

Cpd 85, 3-(4-Chlorophenyl)-2-(2,3-dihydro-1-benzofuran-7-yl)-5-[(2-methylpropyl)sulfonyl]-2,4,5,6-tetrahydropyrrolo[3,4-c]pyrazole;

Cpd 86, 3-(4-Chlorophenyl)-2-(2,3-dihydro-1-benzofuran-7-yl)-5-[(4-methylpiperidin-1-yl)sulfonyl]-2,4,5,6-tetrahydropyrrolo[3,4-c]pyrazole Cpd 87, 3-(4-Chlorophenyl)-5-[(3,5-dimethylisoxazol-4-yl)sulfonyl]-2-(2-methoxyphenyl)-2,4,5,6-tetrahydropyrrolo[3,4-c]pyrazole;

Cpd 88, 2-[3-(4-Chlorophenyl)-5-[(1-methylethyl)sulfonyl]-5,6-dihydropyrrolo[3,4-c]pyrazol-2(4H)-yl]-N,N-dimethylaniline;

Cpd 89, 2-[3-(4-Chlorophenyl)-5-(ethylsulfonyl)-5,6-dihydropyrrolo[3,4-c]pyrazol-2(4H)-yl]-N,N-dimethylaniline;

Cpd 90, 3-(4-Chlorophenyl)-N,N-dimethyl-2-[2-(2,2,2-trifluoroethoxy)phenyl]-2,6-dihydropyrrolo[3,4-c]pyrazole-5(4H)-sulfonamide;

Cpd 91, 2-(2-tert-Butoxyphenyl)-3-(4-chlorophenyl)-N,N-dimethyl-2,6-dihydropyrrolo[3,4-c]pyrazole-5(4H)-sulfonamide;

Cpd 92, 3-(6-Chloropyridin-3-yl)-2-(2-methoxyphenyl)-5-[(1-methylethyl)sulfonyl]-2,4,5,6-tetrahydropyrrolo[3,4-c]pyrazole;

Cpd 93, 3-{2-(2-Methoxyphenyl)-5-[(1-methylethyl)sulfonyl]-2,4,5,6-tetrahydropyrrolo[3,4-c]pyrazol-3-yl}quinoline;

Cpd 94, 2-(2-Methoxyphenyl)-5-[(1-methylethyl)sulfonyl]-3-(6-methylpyridin-3-yl)-2,4,5,6-tetrahydropyrrolo[3,4-c]pyrazole;

Cpd 95, 3-(4-Chlorophenyl)-2-[2-(2,2-difluoroethoxy)phenyl]-N,N-dimethyl-2,6-dihydropyrrolo[3,4-c]pyrazole-5(4H)-sulfonamide;

Cpd 96, 2-(2-Methoxyphenyl)-3-[6-(1-methylethoxy)pyridin-3-yl]-5-[(1-methylethyl)sulfonyl]-2,4,5,6-tetrahydropyrrolo[3,4-c]pyrazole;

Cpd 97, 2-(2-Methoxyphenyl)-3-(6-methoxypyridin-3-yl)-5-[(1-methylethyl)sulfonyl]-2,4,5,6-tetrahydropyrrolo[3,4-c]pyrazole;

and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salts thereof. Suitable pharmaceutically acceptable salts of compounds of Formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+)-\text{enantiomer} = \frac{(\text{mass}(+)-\text{enantiomer})}{(\text{mass}(+)-\text{enantiomer}) + (\text{mass}(-)-\text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)-\text{enantiomer} = \frac{(\text{mass}(-)-\text{enantiomer})}{(\text{mass}(+)-\text{enantiomer}) + (\text{mass}(-)-\text{enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations. Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein; or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As N-Type calcium channel blockers, the compounds of Formula (I) are useful in methods for treating and/or preventing a disease, a syndrome, a condition or a disorder in a subject, including an animal, a mammal and a human in which the disease, the syndrome, the condition or the disorder is affected by the modulation of the N-Type calcium channel. Such methods comprise, consist of and/or consist essentially of administering to a subject, including an animal, a mammal, and a human in need of such treatment or prevention a therapeutically effective amount of a compound, salt or solvate of Formula (I). In particular, the compounds of Formula (I) are useful for preventing or treating pain, such as inflammatory pain or neuropathic pain, or diseases, syndromes, conditions or disorders causing such pain.

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
aq. aqueous
Bn or Bzl benzyl
Boc tert-butyloxycarbonyl
conc. concentrated
DBU 1,8-diazabicyclo[5.4.0]undec-7-ene
DCC N,N'-dicyclohexyl-carbodiimide
DCE 1,2-dichloroethane
DCM dichloromethane
DIBALH diisobutylaluminum hydride
DIPEA or DIEA diisopropyl-ethyl amine
DMF N,N-dimethylformamide
DMSO dimethylsulfoxide
EA ethyl acetate
EDCI 1-ethyl-3-(3-dimethylaminopropyl) carbodiimide
EGTA ethylene glycol tetraacetic acid
ESI electrospray ionization
EtOAc or EA ethyl acetate
EtOH ethanol
h or hr(s) hour or hours
HEK human embryonic kidney
HEPES (4-(2-hydroxyethyl)-1-piperazineethane sulfonic acid
HPLC high performance liquid chromatography
LAH lithium aluminum hydride
LDA lithium diisopropylamide
LHMDS lithium bis(trimethylsilyl)amide
mCPBA meta-chloroperoxybenzoic acid
MeOH methanol
MHz megahertz
min minute or minutes
MS mass spectrometry
Ms methanesulfonyl
NMM N-methylmorpholine
NMR nuclear magnetic resonance
PCC pyridinium chlorochromate
RP reverse-phase
RT room temperature
Rt retention time
Sec second or seconds
TBDMS t-butyldimethylsilyl
TEA or $Et_3N$ triethylamine
TFA trifluoroacetic acid
THF tetrahydrofuran
TIPS triisopropylsilyl
TLC thin layer chromatography
TMS tetramethylsilane Scheme A illustrates a route for the synthesis of compounds of Formula (I)-A and intermediate A9, wherein Q, $R^1$, $R^2$, and $R^3$ are as defined herein, and G is t-butoxycarbonyl group.

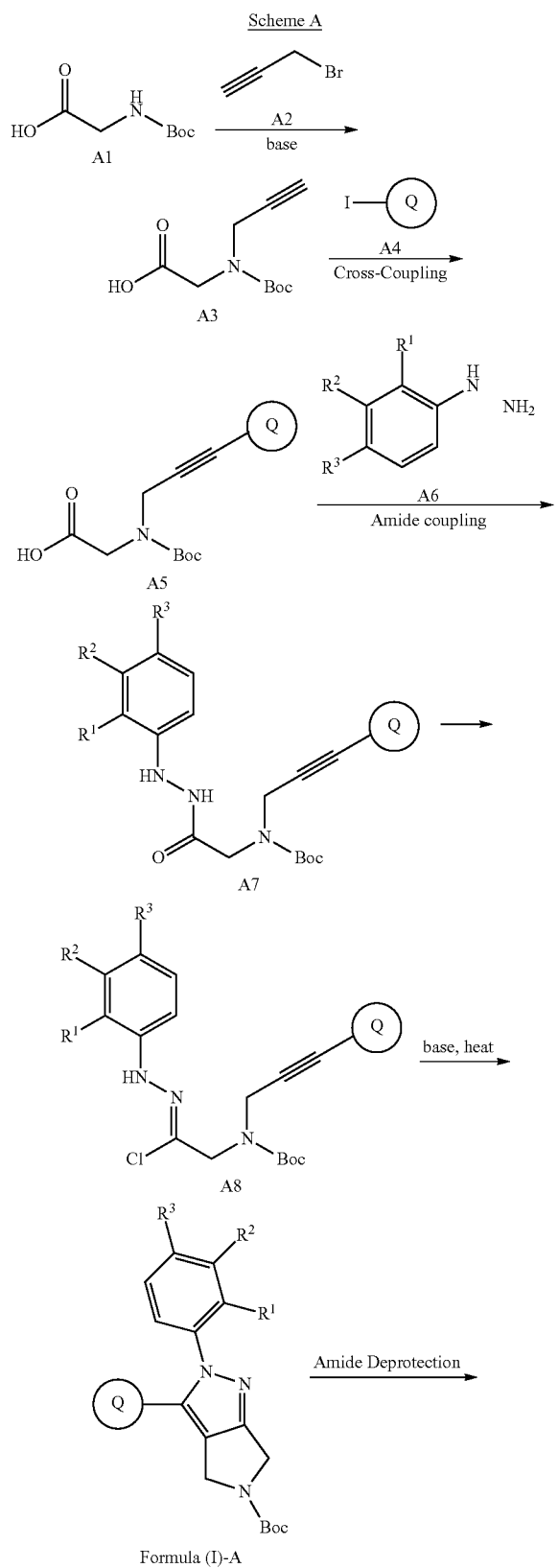

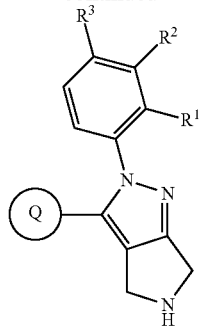

Compound A1 is either commercially available or may be prepared by methods known in the scientific literature. The compound A1 may be alkylated with propargyl bromide in the presence of a strong base, such as sodium hydride, to afford compound A3. Compound A3 may be cross-coupled with an aryl or heteroaryl iodide of formula A4 (wherein Q is as defined herein) in the presence of a palladium catalyst, appropriate ligands, appropriate coupling reagents such as copper iodide, and in the presence of a tertiary amine base such as triethylamine, to afford a compound of formula A5. The compound of formula A5 may be coupled with a substituted hydrazine of formula A6, in the presence of an appropriate amide-type coupling reagents such as EDC and HOBt, or with DCC, to afford a compound of formula A7. Treatment of a compound of formula A7 with triphenylphosphine and carbon tetrachloride, or with $POCl_3$ affords a compound of formula A8, which, upon heating to about 100° C. in the presence of a tertiary amine base such as triethylamine, affords a compound of formula (I)-A. The Boc function group of a compound of formula (I)-A may be removed by treatment with a strong acid, such as trifluoroacetic acid, or a mineral acid such as hydrochloric acid to afford an intermediate compound of formula A9.

Scheme B illustrates a route for the synthesis of compounds of Formula (I)-B, wherein Q, $R^1$, $R^2$, and $R^3$ are as defined herein, and G is a sulfonyl group, wherein $R^B$ is a substituent as defined by the present invention, including, but not limited to, $C_{1-6}$alkyl, $C_{6-10}$aryl($C_{1-4}$alkyl, $C_{6-10}$aryloxy ($C_{1-4}$alkyl, 3,5-dimethylisoxazol-4-yl, $C_{1-4}$alkoxycarbonyl ($C_{1-4}$alkyl, trifluoromethyl, $C_{3-7}$cycloalkyl, 2,2,2-trifluoroethyl, di($C_{1-4}$alkyl)amino, di($C_{1-4}$alkyl)aminosulfonylamino ($C_{1-4}$)alkyl, $C_{1-4}$alkylsulfonylamino($C_{1-4}$)alkyl, and 2,5-dione-pyrrolidin-1-yl-($C_{1-4}$)alkyl.

Scheme B

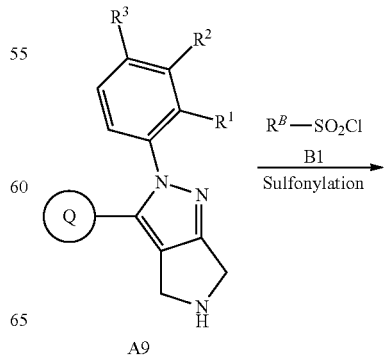

-continued

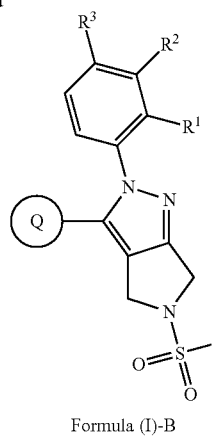

Formula (I)-B

The compound of formula A9 may be treated with an $R^B$-substituted sulfonyl chloride in the presence of an organic amine base, such as triethylamine, to afford a compound of formula (I)-B.

Scheme C illustrates a route for the synthesis of compounds of Formula (I)-C, wherein Q, $R^1$, $R^2$, and $R^3$ are as defined herein, and G is a carbonyl group, wherein $R^C$ is a substituent as defined by the present invention, including, but not limited to, methoxymethyl, trifluoromethyl, $C_{1-4}$alkoxycarbonylamino($C_{2-4}$alkyl, $C_{1-4}$alkoxycarbonylaminomethyl, $C_{1-4}$alkylsulfonylaminomethyl, $C_{1-4}$alkoxy, di($C_{1-4}$alkyl) amino, and pyridinyl.

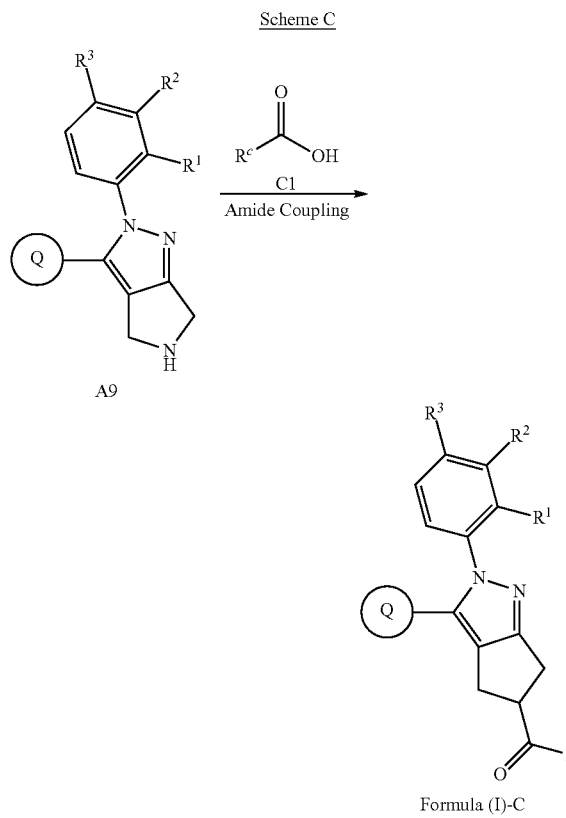

Formula (I)-C

The compound of formula A9 may be coupled with an $R^C$-substituted carboxylic acid of formula C1 in the presence of an appropriate amide-type coupling agent such as polystyrene-supported CDI, and in the presence of a coupling activating agent such as HOBt, to afford a compound of formula (I)-C.

Scheme D illustrates a route for the synthesis of compounds of Formula (I)-D, wherein Q, $R^1$, $R^2$, and $R^3$ are as defined herein, and G is a heteroaryl or aryl ring ($Ar_D$) as defined by G of the present invention.

Scheme D

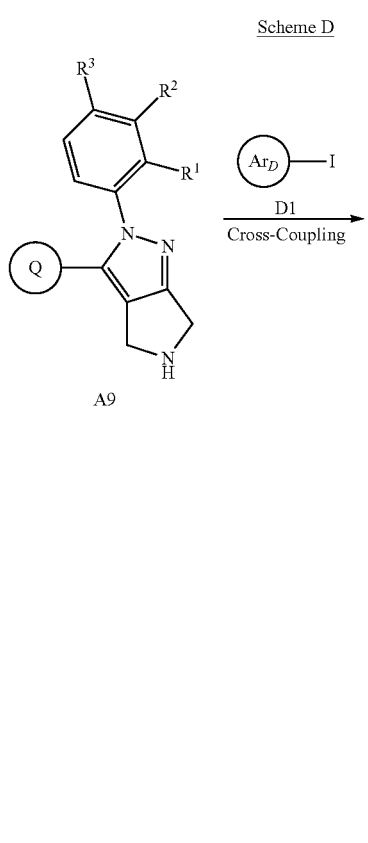

Formula (I)-D

The compound of formula A9 may be coupled with an aryl or heteroaryl ($Ar_D$) iodide of formula D1 in the presence of a transition metal catalyst such as palladium (II), appropriate ligands, and an inorganic base such as potassium or cesium carbonate, to afford a compound of formula (I)-D.

Scheme E illustrates a route for the synthesis of compounds of Formula (I)-E, wherein Q, $R^1$, $R^2$, and $R^3$, and G is as defined herein.

Scheme E

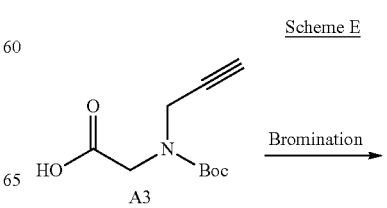

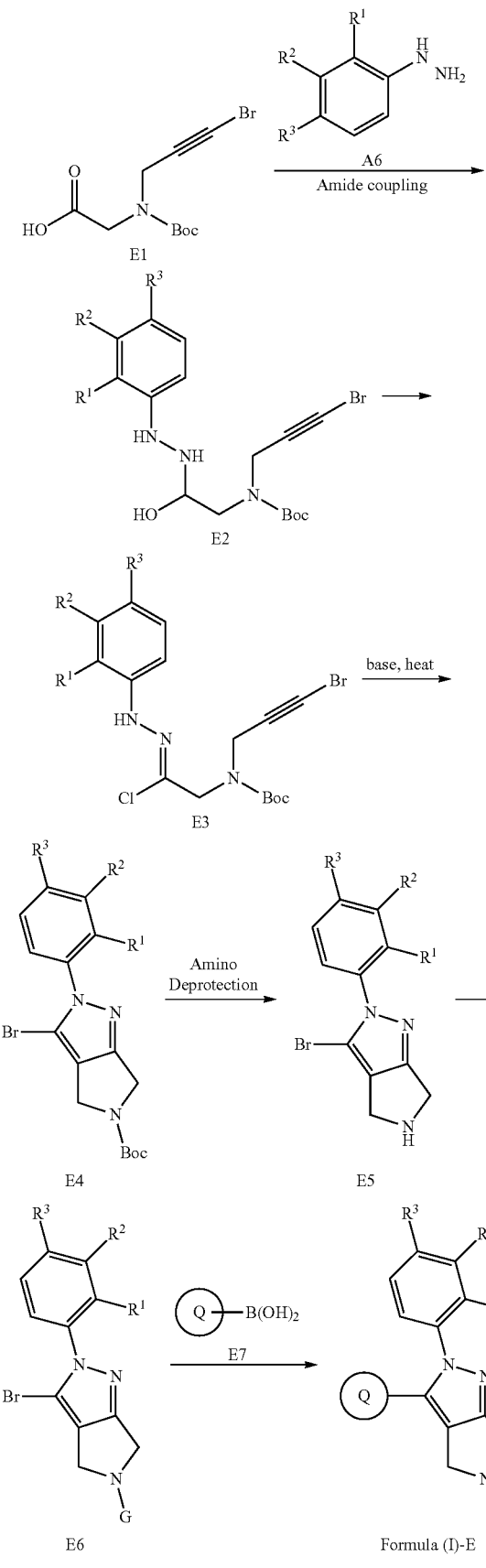

The compound A3 may be brominated in the presence of a brominating reagent such as bromine, to afford compound E1. The compound E1 may be coupled as with a compound of formula A6, using the methods described in Scheme A, to afford a compound of formula E2. A compound of formula E2 may be converted to a compound of formula E3 using the methods described herein, and, upon heating to about 100° C. in the presence of a base, the compound of formula E3 may be cyclized to a compound of formula E4. Upon amino deprotection by conventional methods known to one of skill in the art, a G-group of the present invention may be introduced by one of the methods described in the schemes hereinabove to afford a compound of formula E6. A compound of formula E6 may be cross-coupled with an aryl or heteroaryl boronic acid of formula E7, in the presence of a transition metal catalyst such as palladium (II) acetate, appropriate ligands, and an inorganic base such as sodium carbonate, to afford a compound of formula (I)-E.

SPECIFIC EXAMPLES

Example 1

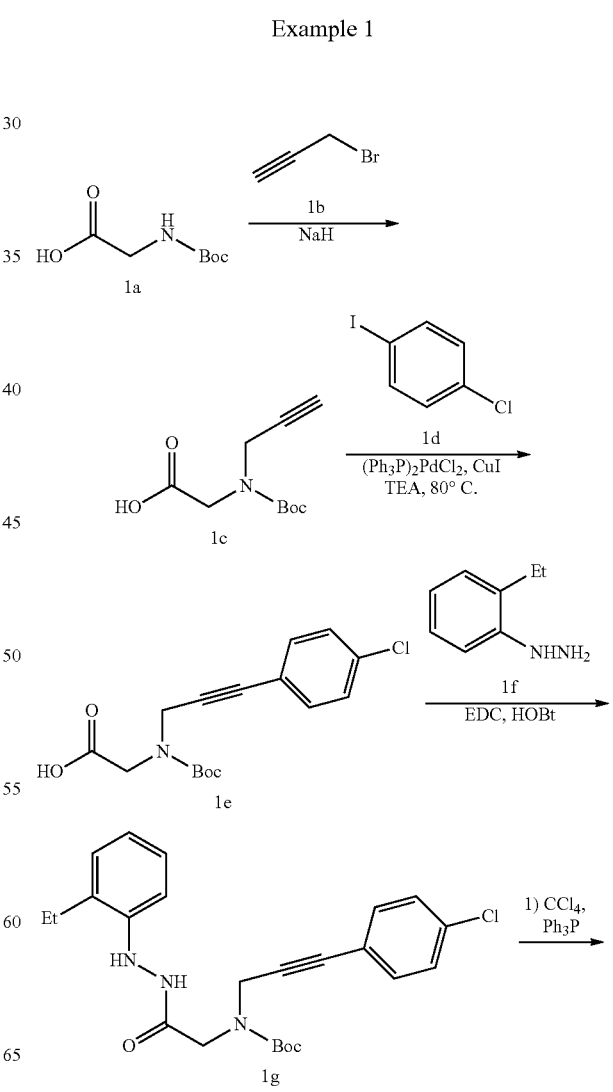

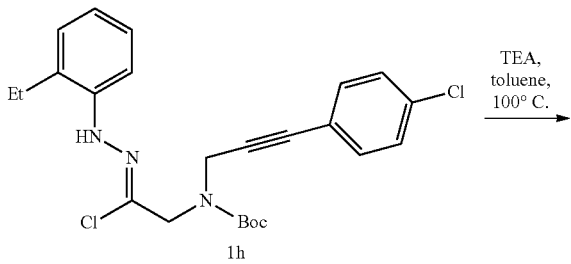

1h

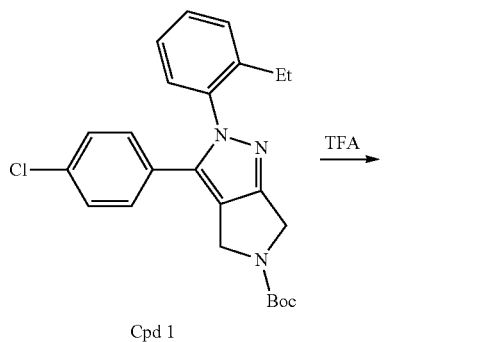

Cpd 1

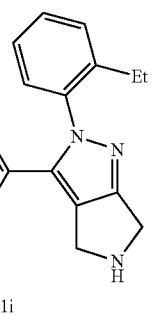

1i

A. To a solution of N-Boc-glycine (1a) (3.0 g, 17.1 mmol, 1.0 eq) in DMF (40 mL) at 0° C. under an Argon atmosphere was added sodium hydride (60% dispersion in oil, 2.12 g, 53.1 mmol, 3.5 eq) in 2 portions, 10 minutes apart. After stirring 1.5 hrs, the bubbling had slowed and propargyl bromide (1b) (80% in toluene, 3.24 mL, 29.1 mmol, 1.7 eq) was added. The grey solution was allowed to warm to rt overnight. Water was added carefully, and the solution brought to pH 3 with 1 N HCl. The aqueous phase was extracted with DCM, dried over MgSO$_4$, filtered, and concentrated. Purification by column chromatography (80 g), eluting with 30 to 50% ethyl acetate/hexanes+0.1% HOAc, afforded compound 1c (3.17 g, 87%). $^1$H NMR (CHLOROFORM-d) δ: 4.06-4.28 (m, 4H), 2.27 (t, J=2.4 Hz, 1H), 1.42-1.52 (m, 9H).

B. To a solution of compound 1c (2.83 g, 13.3 mmol, 1.0 eq) in DMF (30 mL) at rt was added triethylamine (30 mL) followed by 4-chloro-1-iodobenzene (1d) (3.49 g, 14.6 mmol, 1.1 eq), (Ph$_3$P)$_2$PdCl$_2$ (467 mg, 0.67 mmol, 0.05 eq) and copper iodide (253 mg, 1.33 mmol, 0.1 eq). The solution was placed under an Argon atmosphere and heated to 80° C. After 2 hrs, the solution was concentrated, dissolved in DCM, washed sequentially with 1 N HCl and saturated NaHCO$_3$, dried over MgSO$_4$, filtered, and concentrated. Purification by column chromatography (150 g), eluting with 20 to 40% ethyl acetate/hexanes, afforded compound 1e (2.65 g, 62%). $^1$H NMR (CHLOROFORM-d) δ: 7.30-7.36 (m, 2H), 7.27-7.30 (m, 2H), 4.39 (d, J=30.8 Hz, 2H), 4.19 (d, J=25.5 Hz, 2H), 1.42-1.52 (m, 9H C. To a solution of compound 1e (1.33 g, 4.10 mmol, 1.0 eq) in acetonitrile (30 mL) was added EDCI (1.18 g, 6.15 mmol, 1.5 eq) and hydroxybenzotriazole hydrate (831 mg, 6.15 mmol, 1.5 eq). After 15 min, 2-ethylphenylhydrazine (1f) (976 mg, 7.17 mmol, 1.75 eq) was added. After 1 hr, water and 1 N HCl were added, the aqueous phase was extracted with DCM, the combined organic phases were washed with NaHCO$_3$, dried over MgSO$_4$, filtered, and concentrated. Purification by column chromatography (115 g), eluting with 10 to 30 to 40% EA/hexanes, gave compound 1g (1.19 g, 66%). ESI-MS (m/z): Calcd. for C24H28ClN3O3: 464.2 (M+23). found: 464.0.

D. To a solution of compound 1g (1.19 g, 2.69 mmol, 1.0 eq) in acetonitrile (75 mL) was added triphenylphosphine (2.11 g, 8.06 mmol, 3.0 eq) followed by carbon tetrachloride (0.78 mL, 8.06 mmol, 3.0 eq). After 2 hrs, brine was added and the reaction mixture was extracted with EA. The combined organic phases were dried over MgSO$_4$, filtered, and concentrated. Purification by column chromatography (80 g), eluting with 0 to 10% EA/hexanes, compound 1h (718 mg, 58%). $^1$H NMR (CHLOROFORM-d) δ: 7.74 (br. s., 1H), 7.37 (d, J=7.8 Hz, 1H), 7.27-7.33 (m, 2H), 7.19-7.27 (m, 2H), 7.07-7.19 (m, 2H), 6.85-6.93 (m, 1H), 4.22-4.57 (m, 4H), 2.54 (q, J=7.6 Hz, 2H), 1.42-1.58 (m, 9H), 1.25 (t, J=7.5 Hz, 3H). ESI-MS (m/z): Calcd. for C24H27Cl2N3O2: 482.2 (M+23). found: 481.9.

E. A solution of compound 1h (718 mg, 1.56 mmol, 1.0 eq) and triethylamine (0.87 mL, 6.25 mmol, 4.0 eq) in toluene (20 mL) were heated to 100° C. overnight. The solution was cooled, water was added, and the aqueous phase was extracted with EA. The organic phases were combined, dried over MgSO$_4$, filtered, and concentrated. Purification by column chromatography (40 g), eluting with 0 to 15% EA/hexanes, gave compound 1 (600 mg, 91%). $^1$H NMR (CHLOROFORM-d) δ: 7.36-7.42 (m, 1H), 7.31-7.35 (m, 1H), 7.17-7.28 (m, 4H), 6.95-7.01 (m, 2H), 4.54-4.68 (m, 4H), 2.30-2.40 (m, 2H), 1.54 (s, 9H), 1.01 (t, J=7.6 Hz, 3H). ESI-MS (m/z): Calcd. for C24H26ClN3O2: 424.2 (M+1). found: 424.0

F. To a solution of compound 1 (600 mg, 1.42 mmol, 1.0 eq) in DCM (20 mL) was added trifluoroacetic acid (2 mL). After 2 hrs, the solution was concentrated. DCM was added, the solution was washed with NaHCO$_3$, dried over MgSO$_4$, filtered, and concentrated to give compound 1i (396 mg, 86%). $^1$H NMR (CHLOROFORM-d) δ: 7.35-7.41 (m, 1H), 7.32 (d, J=7.6 Hz, 1H), 7.16-7.26 (m, 4H), 6.95-7.01 (m, 2H), 4.22 (s, 2H), 4.14 (s, 2H), 2.38 (q, J=7.6 Hz, 2H), 0.98-1.04 (m, 3H). ESI-MS (m/z): Calcd. for C19H18ClN3: 324.1 (M+1). found: 324.2.

Following the procedure described above for Example 1 and substituting the appropriate reagents, starting materials and purification methods known to those skilled in the art, the following compounds were prepared:

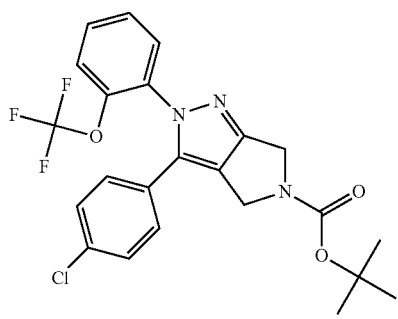

Cpd 19

Cpd 19: ¹H NMR (CHLOROFORM-d) δ: 7.55 (ddd, J=10.0, 7.8, 1.9 Hz, 1H), 7.43-7.49 (m, 1H), 7.36-7.42 (m, 1H), 7.21-7.33 (m, 3H), 6.98-7.06 (m, 2H), 4.62 (s, 2H), 4.57 (d, J=4.3 Hz, 2H), 1.53 (d, J=2.0 Hz, 9H). ESI-MS (m/z): Calcd. for C23H21ClF3N3O3: 480.1 (M+1). found: 480.1.

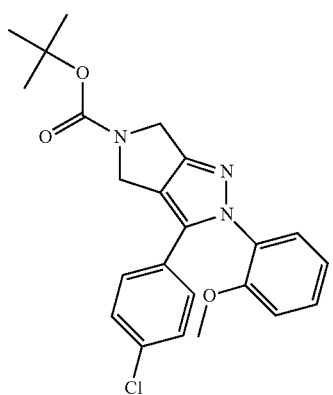

Cpd 28

Cpd 28: ¹H NMR (CHLOROFORM-d) δ: 7.34-7.43 (m, 2H), 7.23 (dd, J=8.5, 6.7 Hz, 2H), 7.01-7.09 (m, 3H), 6.88-6.94 (m, 1H), 4.62 (s, 2H), 4.56 (d, J=9.6 Hz, 2H), 3.52 (s, 3H), 1.53 (s, 9H). ESI-MS (m/z): Calcd. for C23H24ClN3O3: 426.2 (M+1). found: 426.2.

Example 2

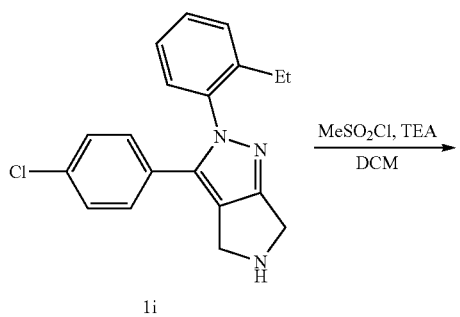

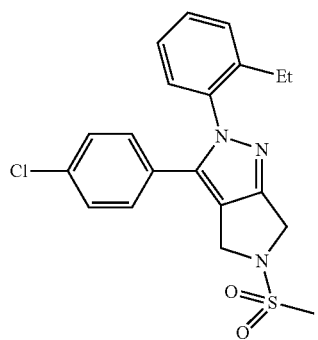

Cpd 2

To a solution of compound 1i (18.5 mg, 0.06 mmol, 1.0 eq) in DCM (1.5 mL) was added methanesulfonylchloride (6.7 μL, 0.09 mmol, 1.5 eq) and triethylamine (15.9 μL, 0.12 mmol, 2.0 eq). After 1 hr, DCM was added, and the solution was washed with saturated aqueous NaHCO₃. The organic phase was dried over MgSO₄, filtered, and concentrated. Purification by column chromatography (8 g), eluting with 20 to 40% EA/hexanes, gave compound 2 (12.8 mg, 56%). ¹H NMR (CHLOROFORM-d) δ: 7.39-7.45 (m, 1H), 7.32-7.37 (m, 1H), 7.17-7.30 (m, 4H), 6.93-6.99 (m, 2H), 4.70 (s, 2H), 4.63 (s, 2H), 2.98 (s, 3H), 2.35 (q, J=7.6 Hz, 2H), 1.02 (t, J=7.6 Hz, 3H). ESI-MS (m/z): Calcd. for C20H20ClN3O2S: 402.1 (M+1). found: 402.1.

Following the procedure described above for Example 2 and substituting the appropriate reagents, starting materials and purification methods known to those skilled in the art, the following compounds were prepared:

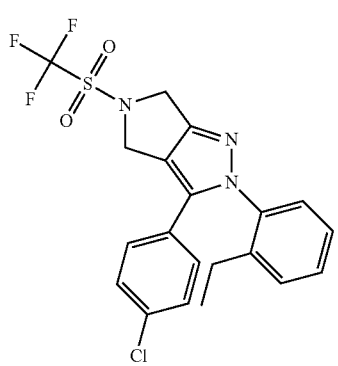

Cpd 3

Cpd 3: ¹H NMR (CHLOROFORM-d) δ: 7.39-7.46 (m, 1H), 7.35 (d, J=6.6 Hz, 1H), 7.17-7.31 (m, 4H), 6.92-6.98 (m, 2H), 4.88 (s, 2H), 4.82 (s, 2H), 2.35 (q, J=7.6 Hz, 2H), 1.03 (t, J=7.6 Hz, 3H). ESI-MS (m/z): Calcd. for C20H17ClF3N3O2S: 456.1 (M+1). found: 456.1.

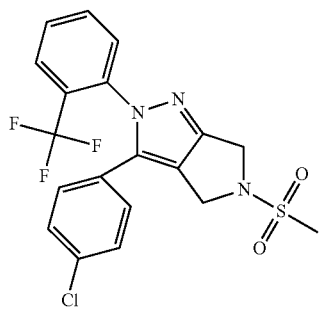

Cpd 15

Cpd 15: ¹H NMR (CHLOROFORM-d) δ: 7.84 (dd, J=5.8, 3.8 Hz, 1H), 7.58-7.65 (m, 2H), 7.29 (dd, J=5.6, 3.5 Hz, 1H), 7.21-7.26 (m, 2H), 6.93-7.00 (m, 2H), 4.68 (s, 2H), 4.64 (t, J=1.5 Hz, 2H), 2.98 (s, 3H). ESI-MS (m/z): Calcd. for C19H15ClF3N3O2S: 442.1 (M+1). found: 442.1.

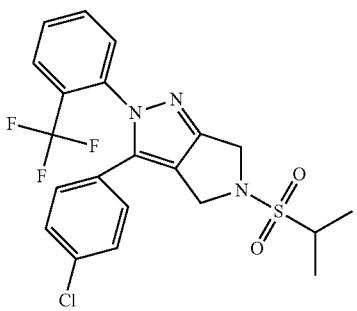

Cpd 16

Cpd 16: ¹H NMR (CHLOROFORM-d) δ: 7.83 (dd, J=5.6, 3.8 Hz, 1H), 7.57-7.64 (m, 2H), 7.29 (dd, J=5.4, 3.7 Hz, 1H), 7.20-7.25 (m, 2H), 6.93-6.99 (m, 2H), 4.75 (br. s., 2H), 4.70 (s, 2H), 3.40 (quin, J=6.8 Hz, 1H), 1.46 (d, J=6.8 Hz, 6H). ESI-MS (m/z): Calcd. for C21H19ClF3N3O2S: 470.1 (M+1). found: 470.1.

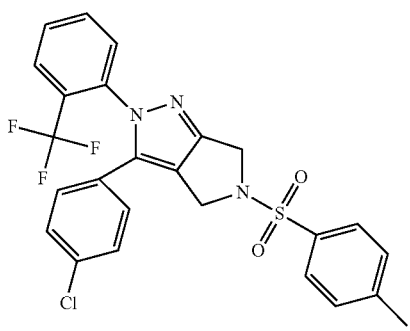

Cpd 17

Cpd 17: ¹H NMR (CHLOROFORM-d) δ: 7.75-7.85 (m, 3H), 7.53-7.63 (m, 2H), 7.36 (d, J=8.1 Hz, 2H), 7.17-7.25 (m, 3H), 6.87-6.95 (m, 2H), 4.59 (s, 2H), 4.56 (s, 2H), 2.44 (s, 3H). ESI-MS (m/z): Calcd. for C25H19ClF3N3O2S: 518.1 (M+1). found: 518.1.

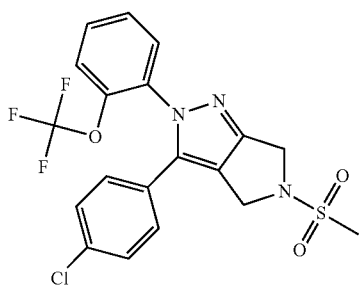

Cpd 20

Cpd 20: ¹H NMR (CHLOROFORM-d) δ: 7.54 (dd, J=7.7, 1.9 Hz, 1H), 7.48 (td, J=7.9, 1.9 Hz, 1H), 7.38-7.45 (m, 1H), 7.23-7.33 (m, 3H), 6.97-7.03 (m, 2H), 4.65 (d, J=4.8 Hz, 4H), 2.97 (s, 3H). ESI-MS (m/z): Calcd. for C19H15ClF3N3O3S: 458.1 (M+1). found: 458.1.

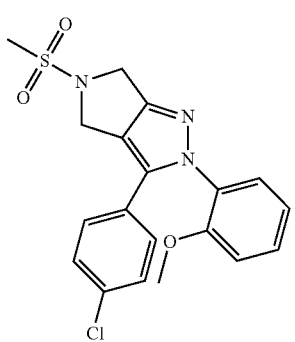

Cpd 30

Cpd 30: ¹H NMR (CHLOROFORM-d) δ: 7.36-7.44 (m, 2H), 7.21-7.26 (m, 2H), 7.00-7.09 (m, 3H), 6.92 (d, J=8.1 Hz, 1H), 4.58-4.72 (m, 4H), 3.53 (s, 3H), 2.95 (s, 3H). ESI-MS (m/z): Calcd. for C19H18ClN3O3S: 404.1 (M+1). found: 404.1.

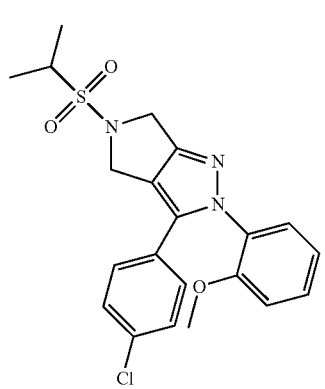

Cpd 31

Cpd 31: ¹H NMR (CHLOROFORM-d) δ: 7.35-7.44 (m, 2H), 7.19-7.25 (m, 2H), 6.99-7.09 (m, 3H), 6.88-6.95 (m, 1H), 4.63-4.79 (m, 4H), 3.54 (s, 3H), 3.38 (quin, J=6.8 Hz, 1H), 1.45 (d, J=6.8 Hz, 6H). ESI-MS (m/z): Calcd. for C21H22ClN3O3S: 432.1 (M+1). found: 432.1.

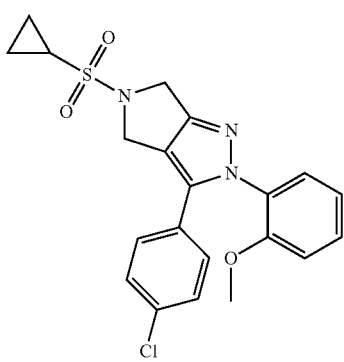

Cpd 32

Cpd 32: ¹H NMR (CHLOROFORM-d) δ: 7.36-7.43 (m, 2H), 7.20-7.26 (m, 2H), 7.00-7.09 (m, 3H), 6.89-6.95 (m, 1H), 4.64-4.77 (m, 4H), 3.54 (s, 3H), 2.42-2.51 (m, 1H), 1.26-1.32 (m, 2H), 0.99-1.06 (m, 2H). ESI-MS (m/z): Calcd. for C21H20ClN3O3S: 430.1 (M+1). found: 430.1.

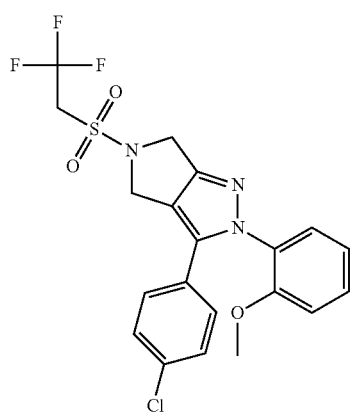

Cpd 36

Cpd 36: ¹H NMR (CHLOROFORM-d) δ: 7.37-7.44 (m, 2H), 7.21-7.26 (m, 2H), 6.99-7.09 (m, 3H), 6.89-6.95 (m, 1H), 4.62-4.81 (m, 4H), 3.88 (q, J=9.3 Hz, 2H), 3.53 (s, 3H). ESI-MS (m/z): Calcd. for C20H17ClF3N3O3S: 472.1 (M+1). found: 472.1.

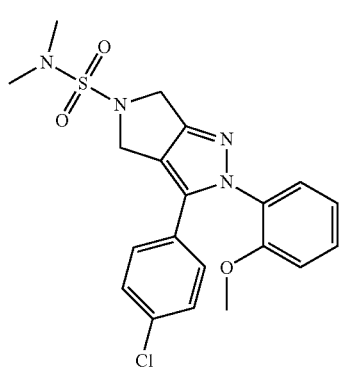

Cpd 33

Cpd 33: ¹H NMR (CHLOROFORM-d) δ: 7.36-7.43 (m, 2H), 7.20-7.25 (m, 2H), 7.00-7.08 (m, 3H), 6.89-6.94 (m, 1H), 4.63 (s, 2H), 4.59 (s, 2H), 3.53 (s, 3H), 2.90 (s, 6H). ESI-MS (m/z): Calcd. for C20H21ClN4O3S: 433.1 (M+1). found: 433.1.

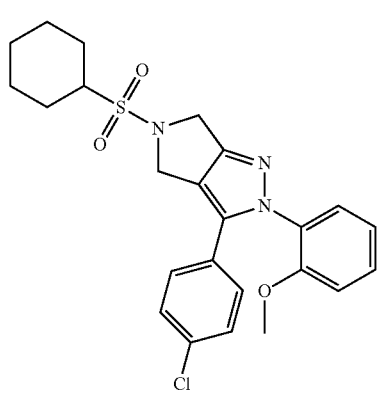

Cpd 37

Cpd 37: ¹H NMR (CHLOROFORM-d) δ: 7.35-7.44 (m, 2H), 7.19-7.25 (m, 2H), 6.99-7.08 (m, 3H), 6.89-6.95 (m, 1H), 4.61-4.79 (m, 4H), 3.53 (s, 3H), 3.04-3.16 (m, 1H), 2.17-2.27 (m, 2H), 1.91 (d, J=12.9 Hz, 2H), 1.59-1.76 (m, 3H), 1.17-1.37 (m, 3H). ESI-MS (m/z): Calcd. for C24H26ClN3O3S: 472.1 (M+1). found: 472.1.

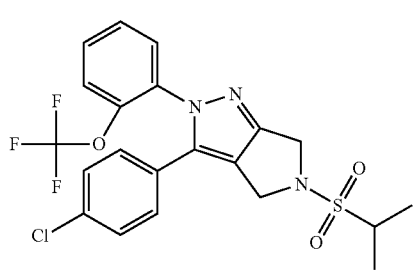

Cpd 35

Cpd 35: ¹H NMR (CHLOROFORM-d) δ: 7.55 (dd, J=7.6, 1.8 Hz, 1H), 7.48 (td, J=7.8, 1.8 Hz, 1H), 7.38-7.44 (m, 1H), 7.22-7.33 (m, 3H), 6.96-7.03 (m, 2H), 4.71 (d, J=10.6 Hz, 4H), 3.39 (quip, J=6.8 Hz, 1H), 1.46 (d, J=6.8 Hz, 6H). ESI-MS (m/z): Calcd. for C21H19ClF3N3O3S: 486.1 (M+1). found: 486.1.

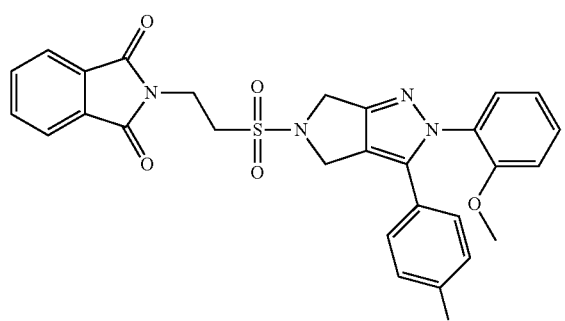

Cpd 38

Cpd 38: ¹H NMR (CHLOROFORM-d) δ: 7.82-7.89 (m, 2H), 7.68-7.76 (m, 2H), 7.35-7.44 (m, 2H), 7.20-7.26 (m,

2H), 6.98-7.09 (m, 3H), 6.91 (d, J=8.3 Hz, 1H), 4.60-4.76 (m, 4H), 4.23 (t, J=6.9 Hz, 2H), 3.47-3.57 (m, 5H). ESI-MS (m/z): Calcd. for C28H23ClN4O5S: 563.1 (M+1). found: 563.1.

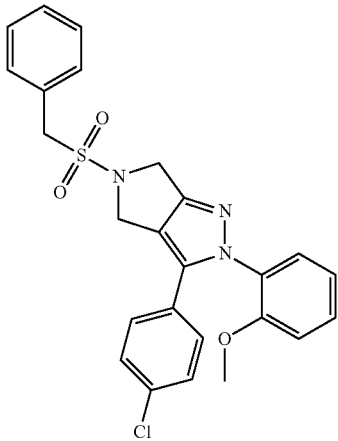

Cpd 39

Cpd 39: ¹H NMR (CHLOROFORM-d) δ: 7.30-7.44 (m, 7H), 7.17-7.23 (m, 2H), 7.02-7.08 (m, 1H), 6.89-6.95 (m, 3H), 4.47 (s, 2H), 4.37 (s, 4H), 3.54 (s, 3H). ESI-MS (m/z): Calcd. for C25H22ClN3O3S: 480.1 (M+1). found: 480.1.

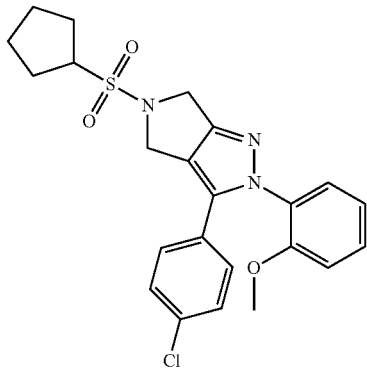

Cpd 40

Cpd 40: ¹H NMR (CHLOROFORM-d) δ: 7.36-7.43 (m, 2H), 7.20-7.25 (m, 2H), 6.99-7.08 (m, 3H), 6.89-6.95 (m, 1H), 4.65-4.77 (m, 4H), 3.59-3.70 (m, 1H), 3.54 (s, 3H), 1.98-2.20 (m, 4H), 1.78-1.91 (m, 2H), 1.59-1.73 (m, 2H). ESI-MS (m/z): Calcd. for C23H24ClN3O3S: 458.1 (M+1). found: 458.1.

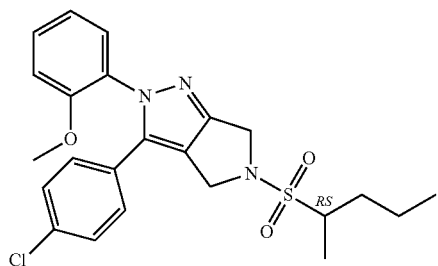

Cpd 41

Cpd 41: ¹H NMR (CHLOROFORM-d) δ: 7.36-7.44 (m, 2H), 7.20-7.25 (m, 2H), 7.00-7.08 (m, 3H), 6.92 (dd, J=8.7, 1.1 Hz, 1H), 4.64-4.78 (m, 4H), 3.54 (s, 3H), 3.21 (td, J=6.7, 3.5 Hz, 1H), 1.96-2.08 (m, 1H), 1.49-1.69 (m, 2H), 1.43 (d, J=6.8 Hz, 3H), 1.32-1.41 (m, 1H), 0.96 (t, J=7.2 Hz, 3H). ESI-MS (m/z): Calcd. for C23H26ClN3O3S: 460.1 (M+1). found: 460.1.

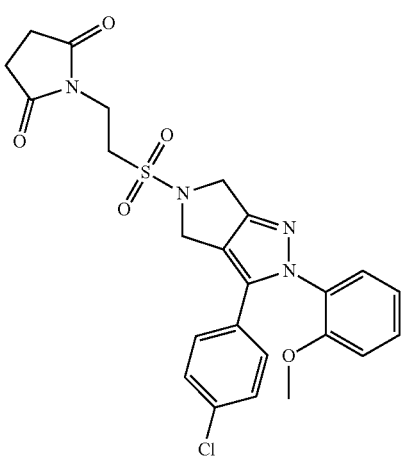

Cpd 42

Cpd 42: ¹H NMR (CHLOROFORM-d) δ: 7.37-7.44 (m, 2H), 7.21-7.26 (m, 2H), 7.01-7.08 (m, 3H), 6.89-6.94 (m, 1H), 4.60-4.75 (m, 4H), 4.04 (t, J=6.6 Hz, 2H), 3.53 (s, 3H), 3.44 (t, J=6.7 Hz, 2H), 2.73 (s, 4H). ESI-MS (m/z): Calcd. for C24H23ClN4O5S: 515.1 (M+1). found: 515.1.

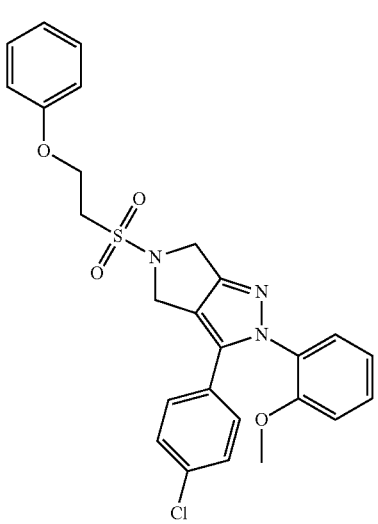

Cpd 43

Cpd 43: ¹H NMR (CHLOROFORM-d) δ: 7.37-7.45 (m, 2H), 7.15-7.24 (m, 4H), 7.03-7.10 (m, 1H), 6.88-6.97 (m, 4H), 6.71 (d, J=7.8 Hz, 2H), 4.68 (d, J=12.6 Hz, 4H), 4.44 (t, J=5.6 Hz, 2H), 3.62 (t, J=5.6 Hz, 2H), 3.56 (s, 3H). ESI-MS (m/z): Calcd. for C26H24ClN3O4S: 510.1 (M+1). found: 510.1.

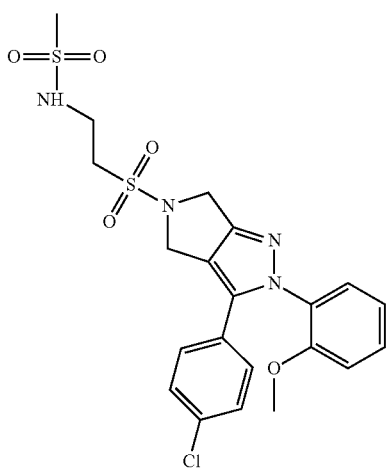

Cpd 44

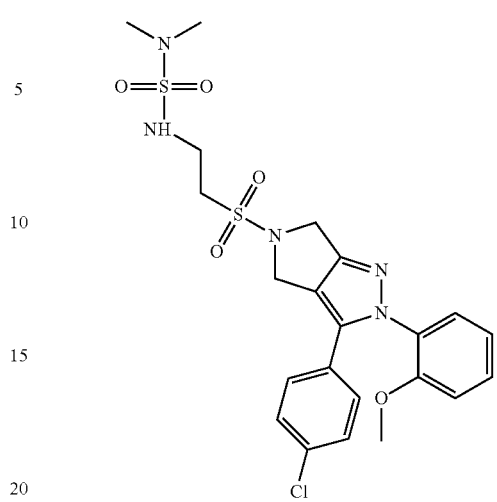

Cpd 46

Cpd 44: ¹H NMR (CHLOROFORM-d) δ: 7.37-7.45 (m, 2H), 7.24 (d, J=8.3 Hz, 2H), 7.00-7.10 (m, 3H), 6.92 (d, J=8.3 Hz, 1H), 5.19-5.28 (m, 1H), 4.61-4.75 (m, 4H), 3.65-3.74 (m, 2H), 3.54 (s, 3H), 3.34 (dd, J=6.6, 4.8 Hz, 2H), 3.01 (s, 3H). ESI-MS (m/z): Calcd. for C21H23ClN4O5S2: 511.1 (M+1). found: 511.1.

Cpd 46: ¹H NMR (CHLOROFORM-d) δ: 7.37-7.44 (m, 2H), 7.21-7.26 (m, 2H), 7.00-7.09 (m, 3H), 6.92 (d, J=7.8 Hz, 1H), 5.06 (t, J=6.4 Hz, 1H), 4.62-4.73 (m, 4H), 3.58-3.66 (m, 2H), 3.54 (s, 3H), 3.35 (dd, J=6.6, 4.8 Hz, 2H), 2.83 (s, 6H). ESI-MS (m/z): Calcd. for C22H26ClN5O5S2: 540.1 (M+1). found: 540.1.

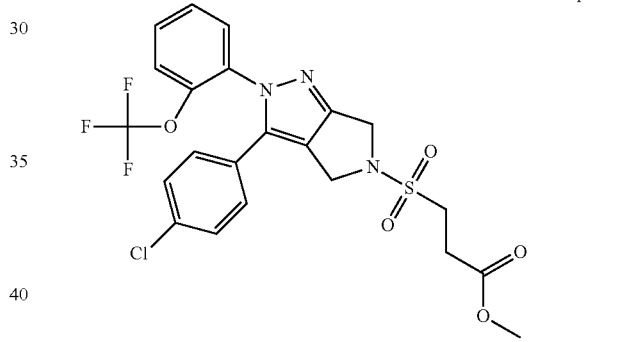

Cpd 47

Cpd 47: ¹H NMR (CHLOROFORM-d) δ: 7.54 (dd, J=7.8, 1.8 Hz, 1H), 7.48 (td, J=7.8, 1.8 Hz, 1H), 7.38-7.45 (m, 1H), 7.23-7.33 (m, 3H), 6.97-7.03 (m, 2H), 4.66 (d, J=4.5 Hz, 4H), 3.66 (s, 3H), 3.47 (t, J=7.3 Hz, 2H), 2.91 (t, J=7.3 Hz, 2H). ESI-MS (m/z): Calcd. for C22H19ClF3N3O5S: 530.1 (M+1). found: 530.1.

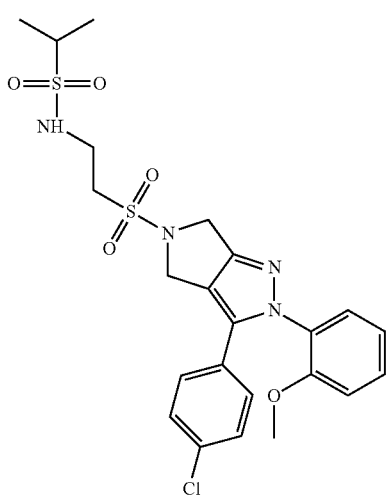

Cpd 45

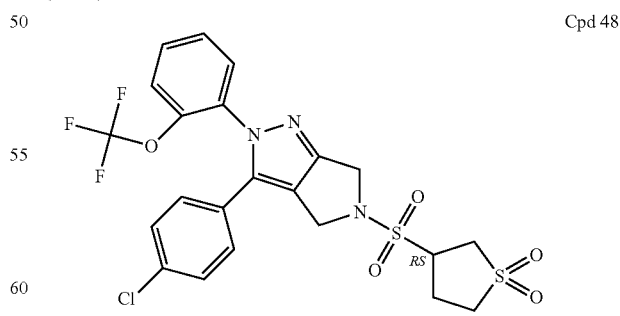

Cpd 48

Cpd 45: ¹H NMR (CHLOROFORM-d) δ: 7.37-7.45 (m, 2H), 7.21-7.26 (m, 2H), 7.00-7.10 (m, 3H), 6.92 (d, J=8.6 Hz, 1H), 5.02 (br. s., 1H), 4.68 (d, J=11.9 Hz, 4H), 3.65-3.75 (m, 2H), 3.54 (s, 3H), 3.33 (dd, J=6.6, 4.8 Hz, 2H), 3.15-3.25 (m, 1H), 1.40 (d, J=6.8 Hz, 6H). ESI-MS (m/z): Calcd. for C23H27ClN4O5S2: 539.1 (M+1). found: 539.1.

Cpd 48: ¹H NMR (CHLOROFORM-d) δ: 7.52-7.57 (m, 1H), 7.49 (td, J=7.9, 1.9 Hz, 1H), 7.42 (td, J=7.6, 1.4 Hz, 1H), 7.24-7.34 (m, 3H), 6.96-7.02 (m, 2H), 4.65-4.79 (m, 4H), 4.02-4.16 (m, 1H), 3.47 (d, J=9.1 Hz, 2H), 3.36-3.45 (m, 1H), 3.16 (dt, J=13.4, 8.0 Hz, 1H), 2.60-2.76 (m, 2H). ESI-MS (m/z): Calcd. for C22H19ClF3N3O5S2: 562.0 (M+1). found: 562.0.

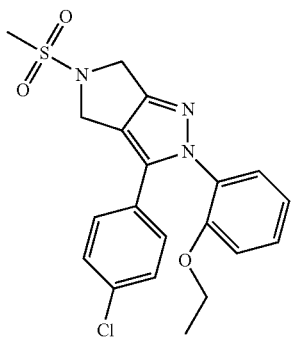

Cpd 49

Cpd 49: ¹H NMR (CHLOROFORM-d) δ: 7.47 (dd, J=7.8, 1.5 Hz, 1H), 7.34-7.41 (m, 1H), 7.23 (d, J=8.6 Hz, 2H), 7.00-7.10 (m, 3H), 6.87 (d, J=8.3 Hz, 1H), 4.63 (br. s., 4H), 3.75 (br. s., 2H), 2.96 (s, 3H), 1.01 (t, J=6.9 Hz, 3H). ESI-MS (m/z): Calcd. for C20H20ClN3O3S: 418.1 (M+1). found: 418.1.

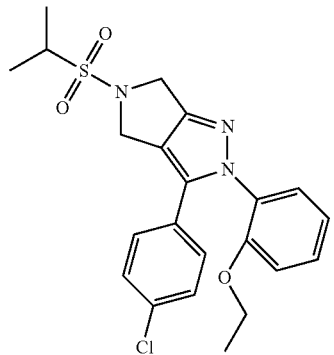

Cpd 50

Cpd 50: ¹H NMR (CHLOROFORM-d) δ: 7.47 (dd, J=7.7, 1.6 Hz, 1H), 7.34-7.40 (m, 1H), 7.19-7.25 (m, 2H), 7.00-7.09 (m, 3H), 6.84-6.89 (m, 1H), 4.69 (br. s., 4H), 3.75 (br. s., 2H), 3.39 (quin, J=6.8 Hz, 1H), 1.45 (d, J=6.8 Hz, 6H), 1.02 (t, J=7.1 Hz, 3H). ESI-MS (m/z): Calcd. for C22H24ClN3O3S: 446.1 (M+1). found: 446.1.

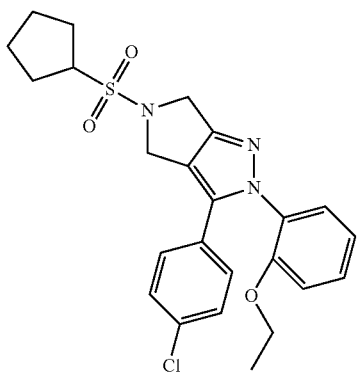

Cpd 51

Cpd 51: ¹H NMR (CHLOROFORM-d) δ: 7.47 (dd, J=7.8, 1.8 Hz, 1H), 7.37 (td, J=8.0, 1.8 Hz, 1H), 7.19-7.25 (m, 2H), 7.01-7.09 (m, 3H), 6.83-6.90 (m, 1H), 4.68 (br. s., 4H), 3.59-3.91 (m, 3H), 1.99-2.21 (m, 4H), 1.78-1.92 (m, 2H), 1.59-1.71 (m, 2H), 1.01 (t, J=6.9 Hz, 3H). ESI-MS (m/z): Calcd. for C24H26ClN3O3S: 472.1 (M+1). found: 472.1.

Cpd 52

Cpd 52: ¹H NMR (CHLOROFORM-d) δ: 7.47 (dd, J=7.7, 1.6 Hz, 1H), 7.37 (td, J=8.0, 1.8 Hz, 1H), 7.19-7.25 (m, 2H), 7.00-7.09 (m, 3H), 6.84-6.89 (m, 1H), 4.54-4.91 (m, 4H), 3.74 (br. s., 2H), 3.11 (tt, J=12.1, 3.4 Hz, 1H), 2.16-2.26 (m, 2H), 1.91 (d, J=12.9 Hz, 2H), 1.59-1.76 (m, 3H), 1.15-1.38 (m, 3H), 1.01 (t, J=6.9 Hz, 3H). ESI-MS (m/z): Calcd. for C25H28ClN3O3S: 486.2 (M+1). found: 486.2.

Cpd 53

Cpd 53: ¹H NMR (CHLOROFORM-d) δ: 7.46 (dd, J=7.7, 1.6 Hz, 1H), 7.29-7.42 (m, 6H), 7.16-7.23 (m, 2H), 7.06 (td, J=7.6, 1.1 Hz, 1H), 6.90-6.97 (m, 2H), 6.84-6.90 (m, 1H), 4.23-4.56 (m, 6H), 3.76 (br. s., 2H), 1.04 (t, J=7.1 Hz, 3H). ESI-MS (m/z): Calcd. for C26H24ClN3O3S: 494.1 (M+1). found: 494.1.

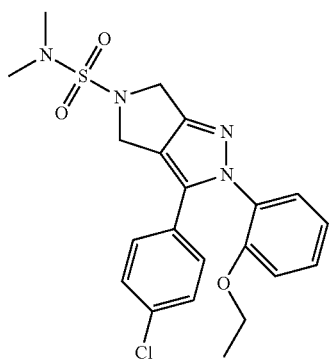

Cpd 54

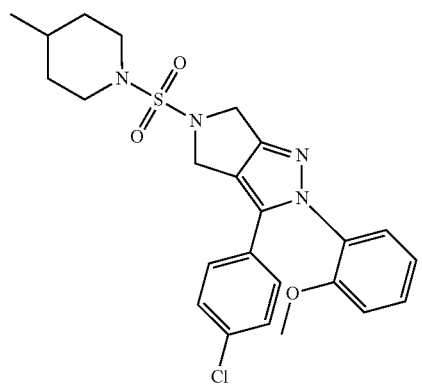

Cpd 57

Cpd 54: ¹H NMR (CHLOROFORM-d) δ: 7.47 (dd, J=7.8, 1.5 Hz, 1H), 7.34-7.40 (m, 1H), 7.19-7.25 (m, 2H), 7.01-7.09 (m, 3H), 6.84-6.89 (m, 1H), 4.59 (br. s., 4H), 3.74 (br. s., 2H), 2.90 (s, 6H), 1.02 (t, J=7.1 Hz, 3H). ESI-MS (m/z): Calcd. for C21H23ClN4O3S: 447.1 (M+1). found: 447.1.

Cpd 57: ¹H NMR (CHLOROFORM-d) δ: 7.35-7.43 (m, 2H), 7.20-7.25 (m, 2H), 6.99-7.08 (m, 3H), 6.89-6.94 (m, 1H), 4.52-4.68 (m, 4H), 3.70-3.80 (m, 2H), 3.53 (s, 3H), 2.78-2.90 (m, 2H), 1.68-1.77 (m, 2H), 1.43-1.57 (m, 1H), 1.20-1.34 (m, 2H), 0.97 (d, J=6.6 Hz, 3H). ESI-MS (m/z): Calcd. for C24H27ClN4O3S: 487.2 (M+1). found: 487.2.

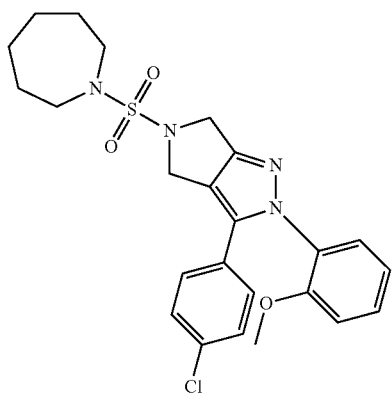

Cpd 55

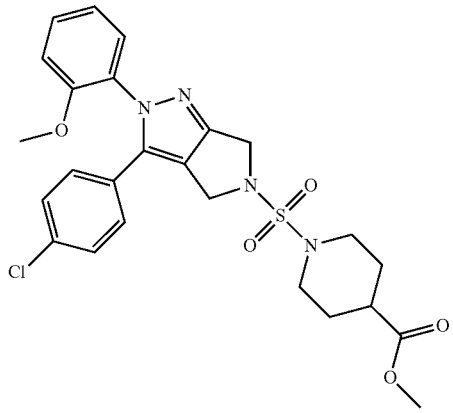

Cpd 58

Cpd 55: ¹H NMR (CHLOROFORM-d) δ: 7.36-7.43 (m, 2H), 7.20-7.25 (m, 2H), 7.00-7.07 (m, 3H), 6.88-6.94 (m, 1H), 4.48-4.65 (m, 4H), 3.53 (s, 3H), 3.40-3.47 (m, 4H), 1.72-1.83 (m, 4H), 1.62-1.70 (m, 4H). ESI-MS (m/z): Calcd. for C24H27ClN4O3S: 487.2 (M+1). found: 487.2.

Cpd 58: ¹H NMR (CHLOROFORM-d) δ: 7.36-7.43 (m, 2H), 7.20-7.25 (m, 2H), 7.00-7.08 (m, 3H), 6.92 (dd, J=8.7, 1.1 Hz, 1H), 4.54-4.68 (m, 4H), 3.67-3.77 (m, 5H), 3.53 (s, 3H), 2.92-3.03 (m, 2H), 2.41-2.51 (m, 1H), 1.97-2.06 (m, 2H), 1.75-1.88 (m, 2H). ESI-MS (m/z): Calcd. for C25H27ClN4O5S: 531.1 (M+1). found: 531.1.

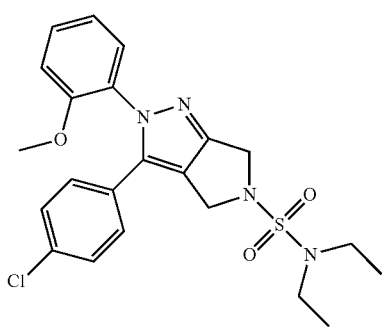

Cpd 56

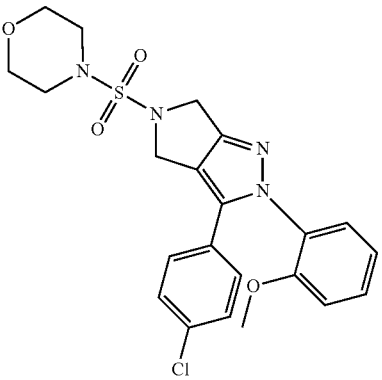

Cpd 59

Cpd 56: ¹H NMR (CHLOROFORM-d) δ: 7.35-7.43 (m, 2H), 7.19-7.25 (m, 2H), 7.00-7.07 (m, 3H), 6.91 (dd, J=8.7, 1.1 Hz, 1H), 4.49-4.65 (m, 4H), 3.53 (s, 3H), 3.35 (q, J=7.2 Hz, 4H), 1.23 (t, J=7.2 Hz, 6H). ESI-MS (m/z): Calcd. for C22H25ClN4O3S: 461.1 (M+1). found: 461.1.

Cpd 59: ¹H NMR (CHLOROFORM-d) δ: 7.36-7.44 (m, 2H), 7.20-7.26 (m, 2H), 6.99-7.08 (m, 3H), 6.92 (d, J=7.8 Hz, 1H), 4.57-4.72 (m, 4H), 3.73-3.80 (m, 4H), 3.53 (s, 3H), 3.27-3.35 (m, 4H). ESI-MS (m/z): Calcd. for C22H23ClN4O4S: 475.1 (M+1). found: 475.1.

Cpd 60

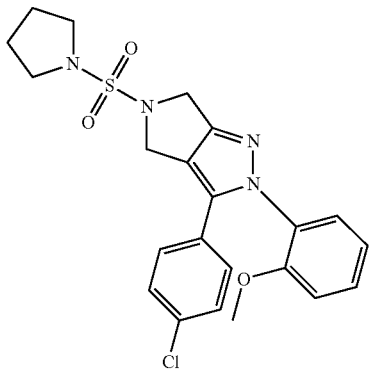

Cpd 60: ¹H NMR (CHLOROFORM-d) δ: 7.36-7.43 (m, 2H), 7.20-7.25 (m, 2H), 7.00-7.08 (m, 3H), 6.92 (dd, J=8.7, 1.1 Hz, 1H), 4.52-4.70 (m, 4H), 3.53 (s, 3H), 3.36-3.43 (m, 4H), 1.91-1.99 (m, 4H). ESI-MS (m/z): Calcd. for C22H23ClN4O3S: 459.1 (M+1). found: 459.1.

Cpd 61

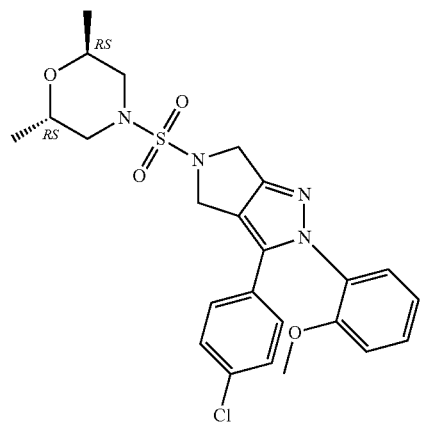

Cpd 61: ¹H NMR (CHLOROFORM-d) δ: 7.36-7.44 (m, 2H), 7.20-7.26 (m, 2H), 6.99-7.08 (m, 3H), 6.92 (d, J=7.8 Hz, 1H), 4.53-4.70 (m, 4H), 3.70 (ddd, J=10.4, 6.3, 2.3 Hz, 2H), 3.50-3.58 (m, 5H), 2.60 (dd, J=12.1, 10.6 Hz, 2H), 1.21 (d, J=6.3 Hz, 6H). ESI-MS (m/z): Calcd. for C24H27ClN4O4S: 503.2 (M+1). found: 503.2.

Cpd 62

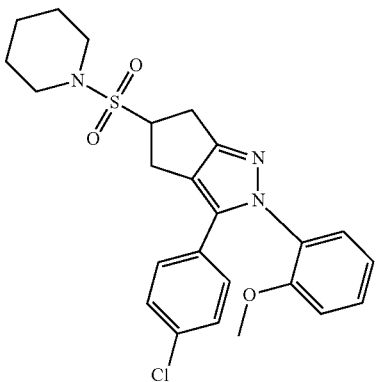

Cpd 62: ¹H NMR (CHLOROFORM-d) δ: 7.36-7.43 (m, 2H), 7.20-7.25 (m, 2H), 7.00-7.08 (m, 3H), 6.92 (dd, J=8.7, 1.1 Hz, 1H), 4.53-4.69 (m, 4H), 3.53 (s, 3H), 3.24-3.33 (m, 4H), 1.52-1.71 (m, 6H). ESI-MS (m/z): Calcd. for C23H25ClN4O3S: 473.1 (M+1). found: 473.1.

Cpd 63

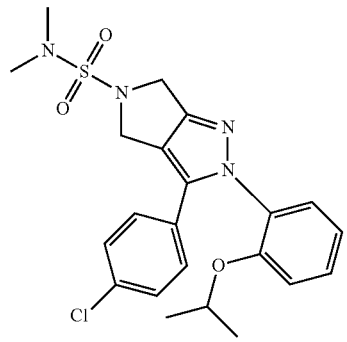

Cpd 63: ¹H NMR (CHLOROFORM-d) δ: 7.51 (dd, J=7.8, 1.8 Hz, 1H), 7.35 (td, J=8.0, 1.8 Hz, 1H), 7.19-7.25 (m, 2H), 7.01-7.08 (m, 3H), 6.84 (d, J=7.8 Hz, 1H), 4.59 (br. s., 4H), 4.28 (dt, J=12.1, 6.1 Hz, 1H), 2.91 (s, 6H), 0.67-1.17 (m, 6H). ESI-MS (m/z): Calcd. for C22H25ClN4O3S: 461.1 (M+1). found: 461.1.

Cpd 87

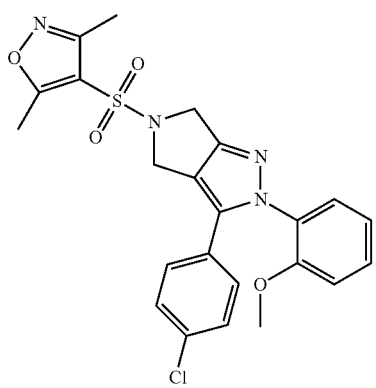

Cpd 87: ¹H NMR (CHLOROFORM-d) δ: 7.34-7.43 (m, 2H), 7.20-7.26 (m, 2H), 6.97-7.07 (m, 3H), 6.87-6.93 (m,

1H), 4.54-4.66 (m, 4H), 3.52 (s, 3H), 2.72 (s, 3H), 2.48 (s, 3H). ESI-MS (m/z): Calcd. for C23H21ClN4O4S: 485.1 (M+1). found: 485.1.

6.98-7.04 (m, 2H), 6.93 (d, J=7.8 Hz, 1H), 4.54-4.69 (m, 4H), 4.05 (q, J=8.2 Hz, 2H), 2.91 (s, 6H). ESI-MS (m/z): Calcd. for C21H20ClF3N4O3S: 501.1 (M+1). found: 501.1.

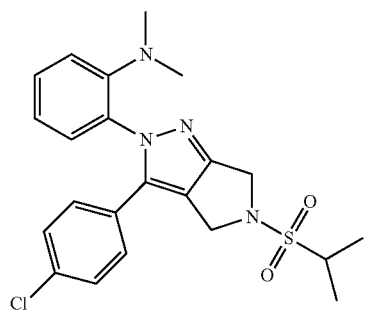

Cpd 88

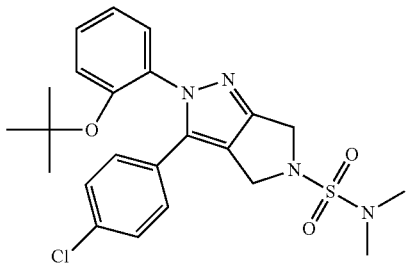

Cpd 91

Cpd 88: ¹H NMR (CHLOROFORM-d) δ: 7.36-7.43 (m, 1H), 7.31 (td, J=7.8, 1.6 Hz, 1H), 7.16-7.22 (m, 2H), 7.02 (td, J=7.6, 1.3 Hz, 1H), 6.93-6.99 (m, 2H), 6.84 (dd, J=8.2, 1.1 Hz, 1H), 4.72-4.92 (m, 2H), 4.62 (d, J=11.9 Hz, 2H), 3.39 (quin, J=6.8 Hz, 1H), 2.22 (s, 6H), 1.45 (d, J=6.8 Hz, 6H). ESI-MS (m/z): Calcd. for C22H25ClN4O2S: 445.1 (M+1). found: 445.1.

Cpd 91: ¹H NMR (CHLOROFORM-d) δ: 7.58 (dd, J=7.8, 1.8 Hz, 1H), 7.33 (td, J=7.8, 1.8 Hz, 1H), 7.16-7.24 (m, 3H), 6.97-7.03 (m, 3H), 4.59 (br. s., 4H), 2.90 (s, 6H), 0.97-1.04 (m, 9H). ESI-MS (m/z): Calcd. for C23H27ClN4O3S: 475.2 (M+1). found: 475.2.

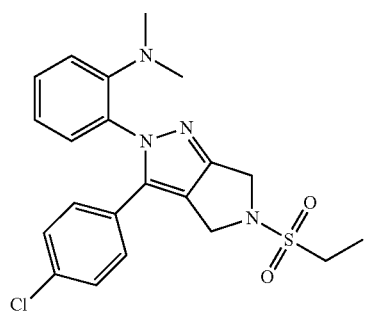

Cpd 89

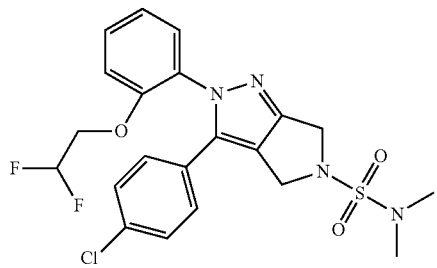

Cpd 95

Cpd 89: ¹H NMR (CHLOROFORM-d) δ: 7.40 (dd, J=7.7, 1.6 Hz, 1H), 7.28-7.34 (m, 1H), 7.17-7.22 (m, 2H), 6.99-7.06 (m, 1H), 6.94-6.99 (m, 1H), 6.84 (dd, J=8.2, 1.1 Hz, 1H), 4.68-4.86 (m, 2H), 4.52-4.65 (m, 2H), 3.15 (q, J=7.4 Hz, 2H), 2.22 (s, 6H), 1.45 (t, J=7.5 Hz, 3H). ESI-MS (m/z): Calcd. for C21H23ClN4O2S: 431.1 (M+1). found: 431.1.

Cpd 95: ¹H NMR (CHLOROFORM-d) δ: 7.49 (dd, J=7.7, 1.6 Hz, 1H), 7.38-7.44 (m, 1H), 7.20-7.25 (m, 2H), 7.16 (td, J=7.6, 1.1 Hz, 1H), 7.00-7.05 (m, 2H), 6.91 (d, J=8.3 Hz, 1H), 5.50-5.81 (m, 1H), 4.55-4.68 (m, 4H), 3.89 (br. s., 2H), 2.91 (s, 6H). ESI-MS (m/z): Calcd. for C21H21ClF2N4O3S: 483.1 (M+1). found: 483.1.

Example 3

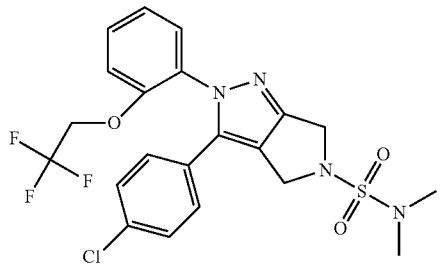

Cpd 90

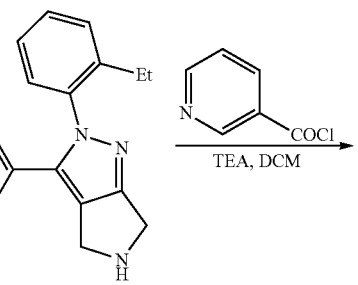

Cpd 90: ¹H NMR (CHLOROFORM-d) δ: 7.52 (dd, J=7.7, 1.6 Hz, 1H), 7.43 (td, J=8.0, 1.8 Hz, 1H), 7.17-7.25 (m, 3H),

1i

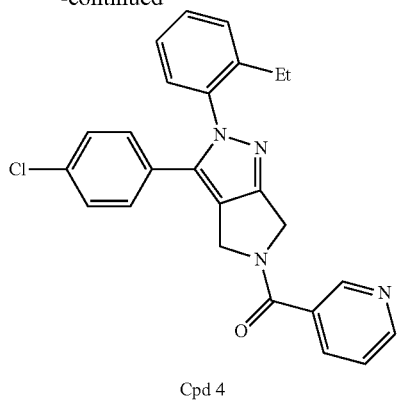

Cpd 4

To a solution of compound 1i (18.5 mg, 0.06 mmol, 1.0 eq) in DCM (1.5 mL) was added nicotinoyl chloride-HCl (15.2 mg, 0.09 mmol, 1.5 eq) and triethylamine (23.8 µL, 0.18 mmol, 3.0 eq). After 1 hr, DCM was added, the solution was washed with saturated aqueous NaHCO₃, dried over MgSO₄, filtered, and concentrated. Purification by column chromatography (8 g), eluting with 1 to 3% MeOH/DCM, gave compound 4 (12.2 mg, 50%). ¹H NMR (CHLOROFORM-d) δ: 8.89 (d, J=2.3 Hz, 1H), 8.74 (dd, J=4.9, 1.6 Hz, 1H), 7.89-7.97 (m, 1H), 7.31-7.48 (m, 3H), 7.13-7.30 (m, 4H), 6.97-7.06 (m, 1H), 6.85-6.94 (m, 1H), 4.99 (d, J=24.0 Hz, 2H), 4.73 (d, J=10.6 Hz, 2H), 2.29-2.41 (m, 2H), 1.02 (td, J=7.6, 3.0 Hz, 3H). ESI-MS (m/z): Calcd. for C25H21ClN4O: 429.1 (M+1). found: 429.1.

Example 4

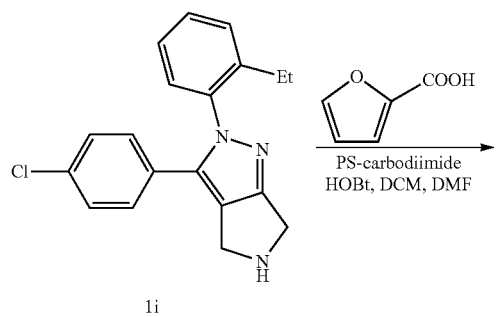

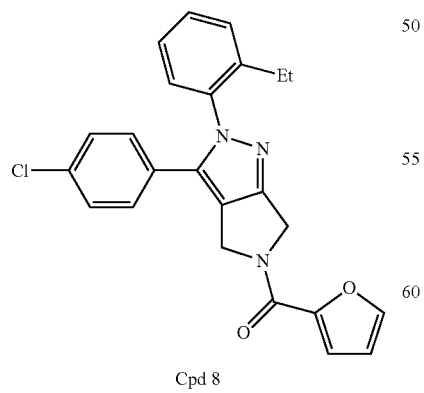

Cpd 8

To a solution of 2-furoic acid (7 mg, 0.06 mmol, 1.5 eq) and HOBt (9 mg, 0.07 mmol, 1.7 eq) in DMF (0.33 mL) was added polystyrene supported (PS)-carbodiimide (64 mg, 1.25 mmol/g, 0.08 mmol, 2 eq). After 10 minutes, compound 1i (13 mg, 0.04 mmol, 1.0 eq) in DCM (1 mL) was added. After 1.5 hr, macroporous (MP)-carbonate resin (65 mg) was added. After 1.5 hrs, the resins were collected by filtration, washed with DCM, and the filtrate was concentrated. Purification by column chromatography (8 g), eluting with 25 to 45% EA/hexanes, gave compound 8 (12.5 mg, 75%). ¹H NMR (CHLOROFORM-d) δ: 7.57-7.64 (m, 1H), 7.38-7.46 (m, 1H), 7.31-7.38 (m, 1H), 7.19-7.31 (m, 5H), 6.98-7.06 (m, 2H), 6.53-6.59 (m, 1H), 5.19 (d, J=20.5 Hz, 2H), 4.89-5.02 (m, 2H), 2.38 (q, J=7.6 Hz, 2H), 0.98-1.08 (m, 3H). ESI-MS (m/z): Calcd. for C24H20ClN3O2: 418.1 (M+1). found: 418.1.

Following the procedure described above for Example 4 and substituting the appropriate reagents, starting materials and purification methods known to those skilled in the art, the following compounds were prepared:

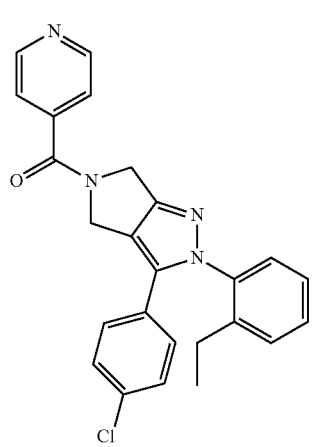

Cpd 5

Cpd 5: ¹H NMR (CHLOROFORM-d) δ: 8.72-8.83 (m, 2H), 7.37-7.50 (m, 3H), 7.31-7.37 (m, 1H), 7.14-7.30 (m, 4H), 6.97-7.04 (m, 1H), 6.86-6.92 (m, 1H), 5.00 (s, 1H), 4.94 (s, 1H), 4.65 (d, J=4.0 Hz, 2H), 2.29-2.41 (m, 2H), 1.02 (td, J=7.6, 2.8 Hz, 3H). ESI-MS (m/z): Calcd. for C25H21ClN4O: 429.1 (M+1). found: 429.1.

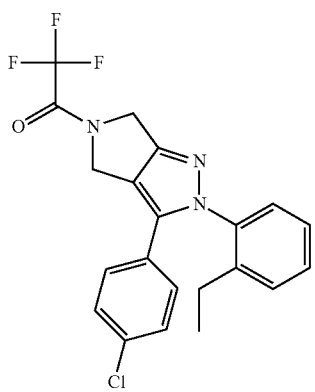

Cpd 6

Cpd 6: ¹H NMR (CHLOROFORM-d) δ: 7.39-7.46 (m, 1H), 7.32-7.38 (m, 1H), 7.18-7.30 (m, 5H), 6.95-7.01 (m, 2H), 4.98 (d, J=19.2 Hz, 2H), 4.87 (d, J=23.0 Hz, 2H), 2.35 (q,

J=7.6 Hz, 2H), 1.03 (td, J=7.6, 1.0 Hz, 3H). ESI-MS (m/z): Calcd. for C21H17ClF3N3O: 420.1 (M+1). found: 420.1.

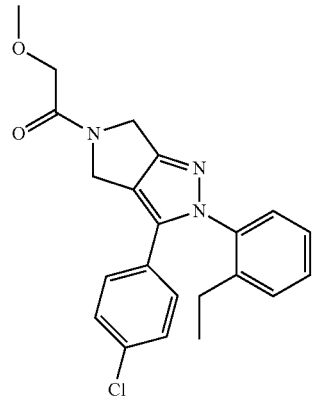
Cpd 10

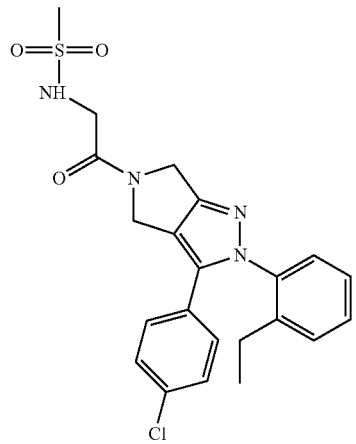
Cpd 12

Cpd 12: ¹H NMR (CHLOROFORM-d) δ: 7.39-7.46 (m, 1H), 7.32-7.38 (m, 1H), 7.18-7.31 (m, 4H), 6.94-7.02 (m, 2H), 5.50 (q, J=4.5 Hz, 1H), 4.66-4.86 (m, 4H), 4.07 (t, J=5.4 Hz, 2H), 3.05 (d, J=2.5 Hz, 3H), 2.35 (q, J=7.6 Hz, 2H), 1.02 (t, J=7.6 Hz, 3H). ESI-MS (m/z): Calcd. for C22H23ClN4O3S: 459.1 (M+1). found: 459.1.

Cpd 10: ¹H NMR (CHLOROFORM-d) δ: 7.37-7.45 (m, 1H), 7.31-7.37 (m, 1H), 7.18-7.30 (m, 4H), 6.95-7.02 (m, 2H), 4.83 (d, J=8.1 Hz, 2H), 4.75 (d, J=14.1 Hz, 2H), 4.17-4.22 (m, 2H), 3.49-3.55 (m, 3H), 2.35 (q, J=7.4 Hz, 2H), 1.02 (td, J=7.6, 1.3 Hz, 3H). ESI-MS (m/z): Calcd. for C22H22ClN3O2: 396.1 (M+1). found: 396.1.

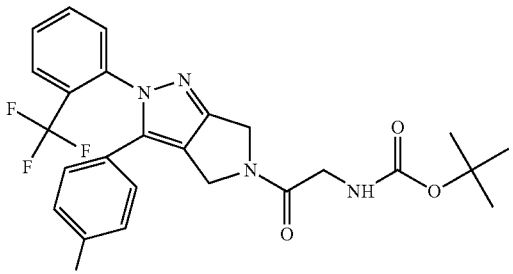
Cpd 18

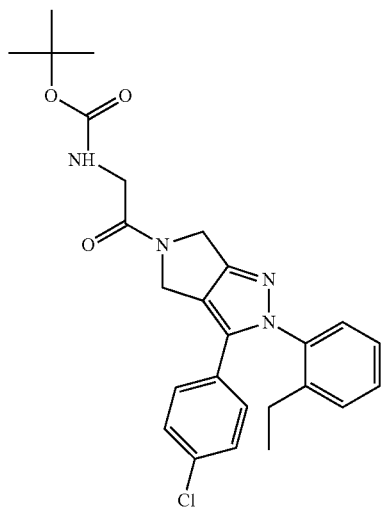
Cpd 11

Cpd 18: ¹H NMR (CHLOROFORM-d) δ: 7.79-7.87 (m, 1H), 7.61 (td, J=4.7, 1.3 Hz, 2H), 7.28-7.34 (m, 1H), 7.21-7.25 (m, 2H), 6.93-7.02 (m, 2H), 5.53 (br. s., 1H), 4.66-4.83 (m, 4H), 3.99-4.10 (m, 2H), 1.47 (s, 9H). ESI-MS (m/z): Calcd. for C25H24ClF3N4O3: 521.2 (M+1). found: 521.2.

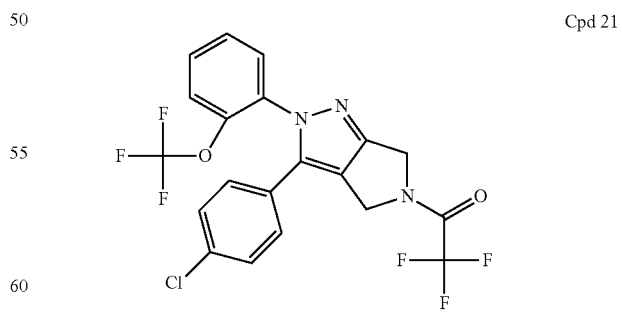
Cpd 21

Cpd 11: ¹H NMR (CHLOROFORM-d) δ: 7.38-7.46 (m, 1H), 7.32-7.37 (m, 1H), 7.24-7.30 (m, 2H), 7.19-7.24 (m, 2H), 6.93-7.01 (m, 2H), 5.53 (br. s., 1H), 4.66-4.84 (m, 4H), 4.05 (d, J=4.5 Hz, 2H), 2.35 (q, J=7.7 Hz, 2H), 1.47 (s, 9H), 1.01 (t, J=7.6 Hz, 3H). ESI-MS (m/z): Calcd. for C26H29ClN4O3: 481.2 (M+1). found: 481.2.

Cpd 21: ¹H NMR (CHLOROFORM-d) δ: 7.52-7.59 (m, 1H), 7.46-7.52 (m, 1H), 7.39-7.45 (m, 1H), 7.23-7.34 (m, 3H), 6.98-7.05 (m, 2H), 4.97 (d, J=3.8 Hz, 2H), 4.85 (d, J=5.6 Hz, 2H). ESI-MS (m/z): Calcd. for C20H12ClF6N3O2: 476.1 (M+1). found: 476.1.

Cpd 22

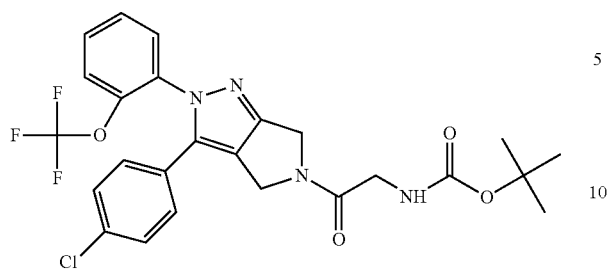

Cpd 22: ¹H NMR (CHLOROFORM-d) δ: 7.52-7.59 (m, 1H), 7.45-7.51 (m, 1H), 7.38-7.45 (m, 1H), 7.23-7.33 (m, 3H), 6.97-7.04 (m, 2H), 5.52 (br. s., 1H), 4.66-4.79 (m, 4H), 4.04 (t, J=4.8 Hz, 2H), 1.47 (s, 9H). ESI-MS (m/z): Calcd. for C25H24ClF3N4O4: 537.2 (M+1). found: 537.2.

Cpd 29

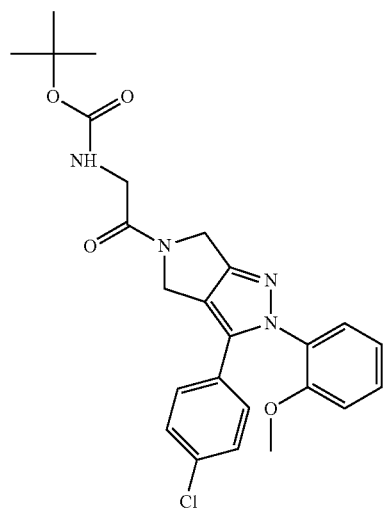

Cpd 29: ¹H NMR (CHLOROFORM-d) δ: 7.36-7.44 (m, 2H), 7.20-7.28 (m, 2H), 7.00-7.09 (m, 3H), 6.92 (dd, J=8.1, 5.3 Hz, 1H), 5.53 (br. s., 1H), 4.65-4.81 (m, 4H), 4.00-4.07 (m, 2H), 3.53 (d, J=3.0 Hz, 3H), 1.47 (s, 9H). ESI-MS (m/z): Calcd. for C25H27ClN4O4: 483.2 (M+1). found: 483.2.

Cpd 34

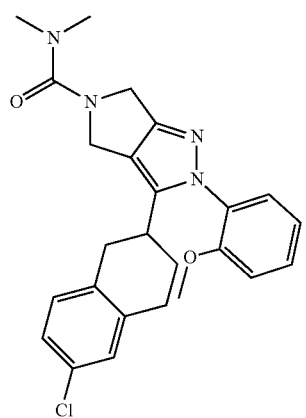

Cpd 34: ¹H NMR (CHLOROFORM-d) δ: 7.35-7.42 (m, 2H), 7.19-7.25 (m, 2H), 7.00-7.09 (m, 3H), 6.91 (d, J=7.6 Hz, 1H), 4.74 (s, 2H), 4.67 (s, 2H), 3.53 (s, 3H), 2.93 (s, 6H). ESI-MS (m/z): Calcd. for C21H21ClN4O2: 397.1 (M+1). found: 397.1.

Example 5

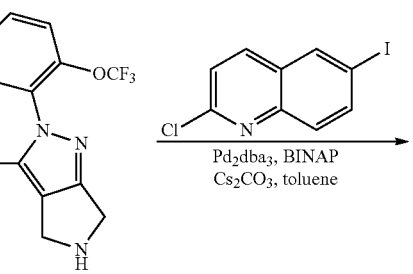

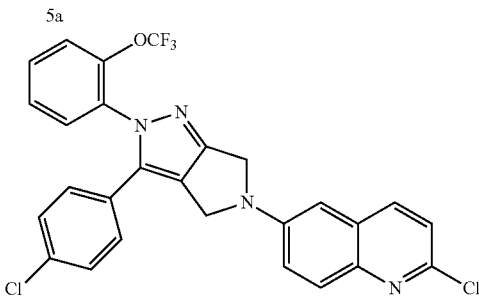

Cpd 27

A. Compound 5a was prepared according to the procedures described for the synthesis of compound 1i in Example 1, substituting 2-trifluoromethoxyphenylhydrazine for 2-ethylphenylhydrazine (1f) in Step C.

B. To a solution of compound 5a (18 mg, 0.06 mmol, 1.0 eq) in toluene (1 mL) was added 2-chloro-6-iodoquinoline (29 mg, 0.12 mmol, 2 eq), Pd₂dba₃ (5.5 mg, 0.006 mmol, 0.1 eq), BINAP (11 mg, 0.018 mmol, 0.3 eq) and cesium carbonate (78 mg, 0.24 mmol, 4 eq), and the mixture was heated to 100° C. for 3 days. Water was added, and the reaction mixture was extracted with DCM. The combined organic phases were dried over MgSO₄, filtered, and concentrated. Purification by column chromatography (8 g), eluting with 15 to 30% EA/hexanes, gave compound 27 (9.0 mg, 28%). ¹H NMR (CHLOROFORM-d) δ: 7.95 (d, J=8.8 Hz, 2H), 7.60 (dd, J=7.8, 1.8 Hz, 1H), 7.45 (dq, J=15.1, 7.7 Hz, 1H), 7.46 (dq, J=15.3, 7.7 Hz, 1H), 7.27-7.35 (m, 5H), 7.06-7.14 (m, 2H), 6.78 (d, J=2.8 Hz, 1H), 4.70 (d, J=4.3 Hz, 4H). ESI-MS (m/z): Calcd. for C27H17Cl2F3N4O: 541.1 (M+1). found: 541.1.

Example 6

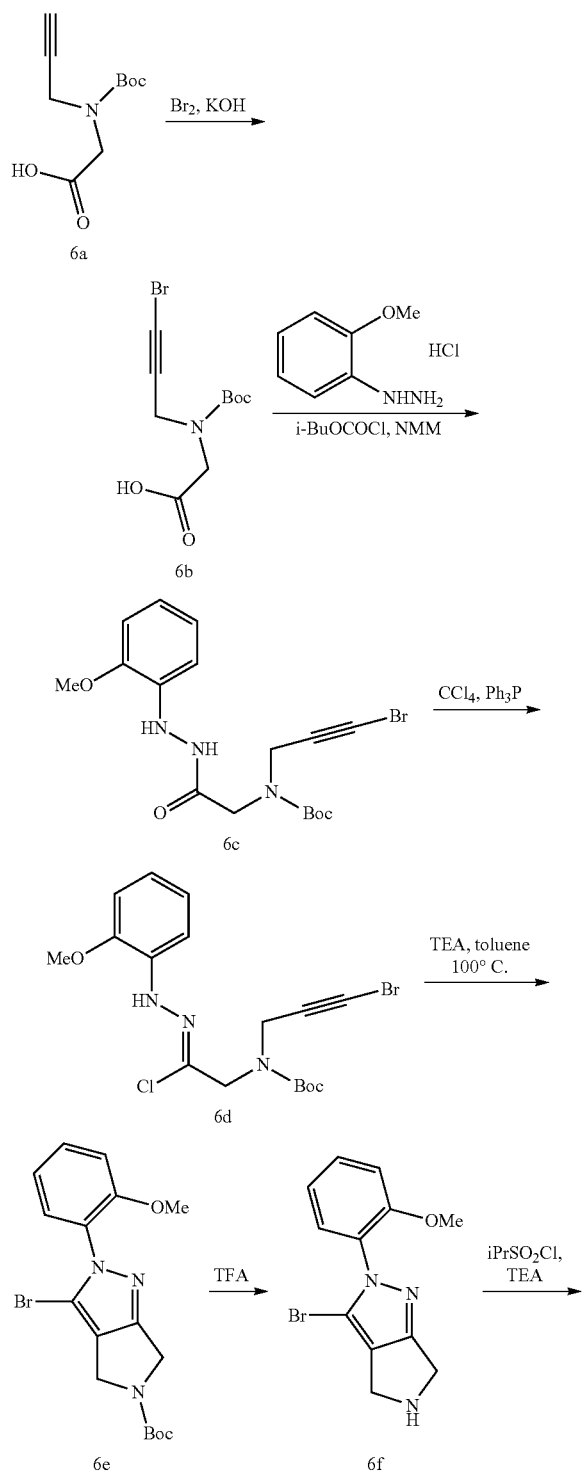

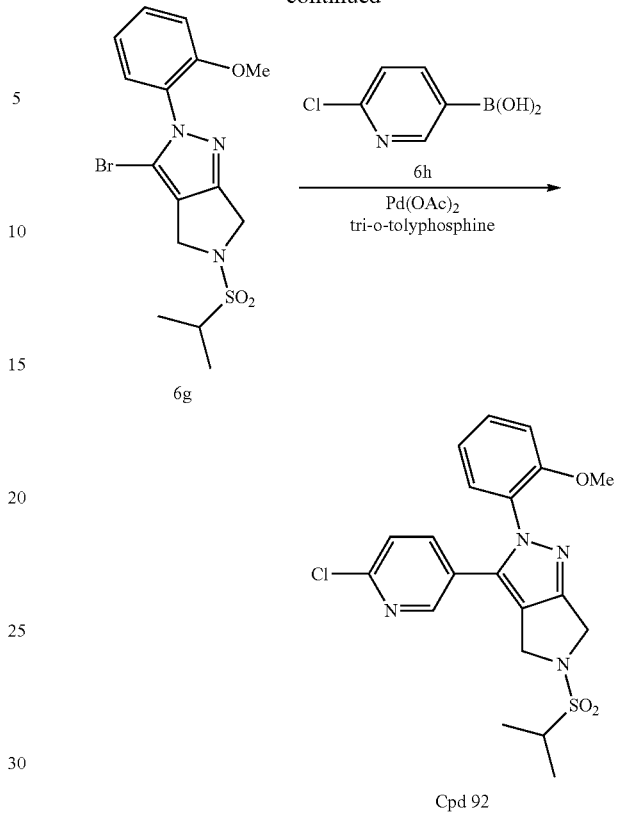

A. To a solution of KOH (3.27 g, 58.3 mmol, 7 eq) in H$_2$O (50 mL) at 0° C. was added bromine (1.33 g, 8.32 mmol, 1 eq). After 15 min, compound 6a (1.77 g, 8.32 mmol, 1 eq) in methanol (15 mL) was added dropwise over 2 min, and the reaction mixture was stirred for 1 hr at 0° C. The solution was made acidic with concentrated HCl, then extracted with EA. The combined organic phases were dried over MgSO$_4$, filtered, and concentrated. Purification by column chromatography (160 g), eluting with 25 to 50% EA/hexanes+0.1% HOAc, gave compound 6b (1207 mg, 47%). $^1$H NMR (CHLOROFORM-d) δ: 4.00-4.32 (m, 4H), 1.35-1.52 (m, 9H).

B. To a solution of compound 6b (1189 mg, 4.07 mmol, 1 eq) in THF (20 mL) at rt under an Argon atmosphere was added N-methylmorpholine (0.47 mL, 4.27 mmol, 1.05 eq) followed by isobutylchloroformate (0.56 mL, 4.27 mmol, 1.05 eq). After 30 min, a solution of 2-methoxyphenylhydrazine-HCl (746 mg, 4.27 mmol, 1.05 eq) and N-methylmorpholine (0.47 mL, 4.27 mmol, 1.05 eq) in THF (20 mL) (pre-stirred for 20 min) was added and the solution was stirred for 60 min. Saturated aqueous NaHCO$_3$ and brine were sequentially added, and the aqueous mixture was extracted with EA. The combined organic phases were dried over MgSO$_4$, filtered, and concentrated. Purification by column chromatography (40 g), eluting with 25 to 50% EA/hexanes, gave compound 6c (1.29 g, 77%). ESI-MS (m/z): Calcd. for C17H22BrN3O4: 412.1 (M+1). found: 412.1.

C. To a solution of compound 6c (1.29 g, 3.14 mmol, 1 eq) in acetonitrile (20 mL) at rt was added carbon tetrachloride (0.91 mL, 9.41 mmol, 3 eq) followed by triphenylphosphine (2.47 g, 9.41 mmol, 3 eq). After 2 hrs, brine was added and the aqueous solution was extracted with EA. The combined organic phases were dried over MgSO₄, filtered, and concentrated. Purification by column chromatography (40 g), eluting with 3 to 8% EA/hexanes, gave compound 6d (604 mg, 45%). ¹H NMR (CHLOROFORM-d) δ: 8.17 (br. s., 1H), 7.34 (d, J=7.8 Hz, 1H), 6.81-6.98 (m, 3H), 4.33-4.51 (m, 2H), 4.02-4.28 (m, 2H), 3.90 (s, 3H), 1.39-1.60 (m, 9H).

D. A solution of compound 6d (604 mg, 1.4 mmol, 1 eq) and triethylamine (0.78 mL, 5.6 mmol, 4 eq) in toluene (12 mL) was heated to 110° C. for 3 hrs. Water was added to the reaction mixture, and the aqueous phase was extracted with DCM. The combined organics were dried over MgSO₄, filtered, and concentrated. Purification by column chromatography, eluting with 15 to 30% EA/hexanes, gave compound 6e (411 mg, 74%). ¹H NMR (CHLOROFORM-d) δ: 7.43-7.50 (m, 1H), 7.33 (d, J=7.8 Hz, 1H), 7.02-7.10 (m, 2H), 4.59 (s, 1H), 4.53 (s, 1H), 4.47 (s, 1H), 4.44 (s, 1H), 3.83 (s, 3H), 1.52 (d, J=1.8 Hz, 9H). ESI-MS (m/z): Calcd. for C17H20BrN3O3: 394.1 (M+1). found: 394.0.

E. A solution of compound 6e (411 mg, 1.04 mmol, 1 eq) in trifluoroacetic acid (1 mL) and DCM (5 mL) was stirred 3 hrs and concentrated. The residue was dissolved in DCM and washed with saturated aqueous NaHCO₃. The organic phase was dried over MgSO₄, filtered, and concentrated to give compound 6f (290 mg, 95%). ¹H NMR (CHLOROFORM-d) δ: 7.45 (td, J=7.9, 1.6 Hz, 1H), 7.34 (dd, J=8.1, 1.8 Hz, 1H), 7.01-7.09 (m, 2H), 4.11 (s, 2H), 4.04 (s, 2H), 3.83 (s, 3H), 2.97 (br. s., 1H). ESI-MS (m/z): Calcd. for Cl2H12BrN3O: 294.0 (M+1). found: 294.0.

F. To compound 6f (290 mg, 0.99 mmol, 1 eq) in DCM (5 mL) at rt was added diisopropylethylamine (0.52 mL, 2.96 mmol, 3 eq) followed by isopropylsulfonyl chloride (0.22 mL, 1.97 mmol, 2 eq) for approximately 18 hr. Saturated aqueous NaHCO₃ was added, and the mixture was extracted with DCM. The combined organic phases were dried over MgSO₄, filtered, and concentrated. Purification by column chromatography (24 g), eluting with 20 to 40% EA/hexanes, gave compound 6g (281 mg, 71%). ¹H NMR (CHLOROFORM-d) δ: 7.48 (td, J=8.0, 1.8 Hz, 1H), 7.30-7.36 (m, 1H), 7.02-7.10 (m, 2H), 4.67 (s, 2H), 4.58 (d, J=1.5 Hz, 2H), 3.84 (s, 3H), 3.37 (quin, J=6.8 Hz, 1H), 1.44 (d, J=7.1 Hz, 6H). ESI-MS (m/z): Calcd. for C15H18BrN3O3S: 400.0 (M+1). found: 400.0.

G. To a solution of compound 6g (16 mg, 0.04 mmol, 1 eq) in dimethoxyethane (1 mL) and 2 M sodium carbonate (0.25 mL) in a vial was added 2-chloro-5-pyridineboronic acid (19 mg, 0.12 mmol, 3 eq), palladium acetate (1 mg, 0.004 mmol, 0.1 eq) and tri-o-tolylphosphine (1.2 mg, 0.004 mmol, 0.1 eq). The mixture was heated to 80° C. for 15 minutes. The mixture was cooled to rt, water was added, and the aqueous phase was extracted with DCM. The combined organic phases were dried over MgSO₄, filtered, and concentrated. Purification by column chromatography (8 g), eluting with 20 to 40 to 50% EA/hexanes, gave compound 92 (6.5 mg, 36%). ¹H NMR (CHLOROFORM-d) δ: 8.11 (d, J=2.3 Hz, 1H), 7.31-7.39 (m, 2H), 7.27 (dd, J=8.3, 2.5 Hz, 1H), 7.16 (d, J=8.3 Hz, 1H), 6.96-7.04 (m, 1H), 6.86 (d, J=7.8 Hz, 1H), 4.65 (d, J=14.9 Hz, 4H), 3.50 (s, 3H), 3.32 (quin, J=6.8 Hz, 1H), 1.38 (d, J=6.8 Hz, 6H). ESI-MS (m/z): Calcd. for C20H21ClN4O3S: 433.1 (M+1. found: 433.1.

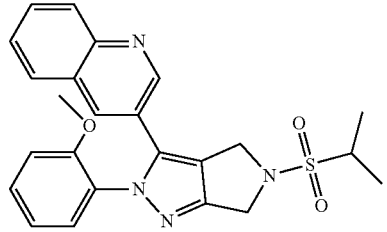

Cpd 93

Cpd 93: ¹H NMR (CHLOROFORM-d) δ: 8.67 (d, J=2.3 Hz, 1H), 8.04 (d, J=8.3 Hz, 1H), 7.86 (d, J=2.0 Hz, 1H), 7.65-7.77 (m, 2H), 7.51-7.59 (m, 1H), 7.46 (dd, J=7.8, 1.5 Hz, 1H), 7.37-7.44 (m, 1H), 7.06 (td, J=7.6, 1.1 Hz, 1H), 6.91 (d, J=8.3 Hz, 1H), 4.84 (s, 2H), 4.75 (s, 2H), 3.50 (s, 3H), 3.41 (quin, J=6.8 Hz, 1H), 1.47 (d, J=7.1 Hz, 6H). ESI-MS (m/z): Calcd. for C24H24N4O3S: 449.2 (M+1). found: 449.2.

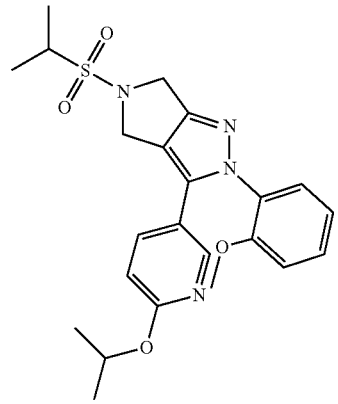

Cpd 96

Cpd 96: ¹H NMR (CHLOROFORM-d) δ: 7.96 (d, J=2.5 Hz, 1H), 7.34-7.44 (m, 2H), 7.22 (dd, J=8.6, 2.5 Hz, 1H), 7.04 (t, J=7.7 Hz, 1H), 6.94 (d, J=8.3 Hz, 1H), 6.54 (d, J=8.6 Hz, 1H), 5.24 (quin, J=6.2 Hz, 1H), 4.71 (d, J=14.1 Hz, 4H), 3.60 (s, 3H), 3.38 (quin, J=6.9 Hz, 1H), 1.45 (d, J=6.8 Hz, 6H), 1.31 (d, J=6.3 Hz, 6H). ESI-MS (m/z): Calcd. for C23H28N4O4S: 457.2 (M+1). found: 457.2.

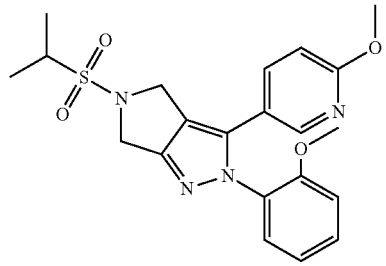

Cpd 97

Cpd 97: ¹H NMR (CHLOROFORM-d) δ: 7.98 (d, J=2.5 Hz, 1H), 7.33-7.45 (m, 2H), 7.21-7.27 (m, 1H), 7.04 (t, J=7.7 Hz, 1H), 6.94 (d, J=8.1 Hz, 1H), 6.62 (d, J=8.6 Hz, 1H), 4.71 (d, J=12.4 Hz, 4H), 3.90 (s, 3H), 3.60 (s, 3H), 3.38 (quin, J=6.9 Hz, 1H), 1.45 (d, J=6.6 Hz, 6H). ESI-MS (m/z): Calcd. for C21H24N4O4S: 429.2 (M+1). found: 429.2.

Example 7

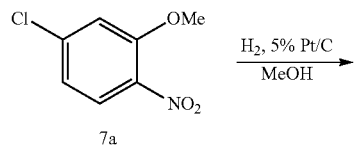

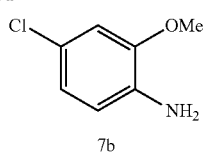

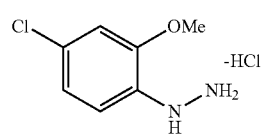

A. A suspension of 5-chloro-2-nitroanisole (7a) (2.67 g, 14.2 mmol) and 5% Pt/C (200 mg) in methanol (60 mL) was placed under a hydrogen gas atmosphere and stirred 3 days. The suspension was filtered through diatomaceous earth and concentrated. Purification by column chromatography (40 g), eluting with 15 to 30% EA/hexanes, gave compound 7b (1.69 g, 76%). $^1$H NMR (CHLOROFORM-d) δ: 6.70-6.83 (m, 2H), 6.58-6.64 (m, 1H), 3.84 (s, 3H), 3.76 (br. s., 2H). ESI-MS (m/z): Calcd. for C7H8ClNO: 158.0 (M+1). found: 158.0.

B. To a suspension of compound 7b (1.69 g, 10.7 mmol, 1 eq) in concentrated HCl (25 mL) and acetic acid (10 mL) at 0° C. was added a solution of sodium nitrite (740 mg, 10.7 mmol, 1 eq) in water (10 mL) dropwise. The suspension was warmed to 60° C. for 1.5 hrs. The solution was cooled to 0° C. and a solution of SnCl$_2$ (5.32 g, 23.6 mmol, 2.2 eq) in concentrated HCl (25 mL) was added. After 30 minutes, a precipatate was collected by filtration to give compound 7c (2.06 g, 93%). $^1$H NMR (DMSO-d$_6$) δ: 9.94 (br. s., 2H), 7.72 (br. s., 1H), 7.07 (s, 1H), 7.00 (s, 2H), 3.85 (s, 3H).

Following the procedure described above for Example 7 and substituting the appropriate reagents, starting materials and purification methods known to those skilled in the art, the following intermediates to compounds of the present invention were prepared:

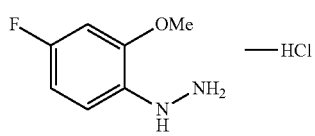

Cpd 7d: $^1$H NMR (free base, CHLOROFORM-d) δ: 6.89 (dd, J=8.7, 5.7 Hz, 1H), 6.60-6.69 (m, 1H), 6.52-6.60 (m, 1H), 3.0-5.0 (brd. s, 3H), 3.82 (s, 3H).

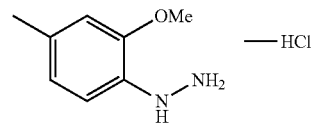

Cpd 7e: $^1$H NMR (DMSO-d$_6$) δ: 9.38 (br. s., 2H), 7.36 (br. s., 1H), 6.88 (d, J=7.8 Hz, 1H), 6.80-6.84 (m, 1H), 6.69-6.75 (m, 1H), 3.81 (s, 3H), 2.26 (s, 3H).

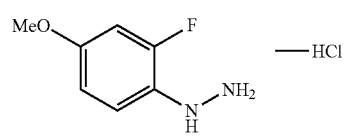

Cpd 7f: $^1$H NMR (DMSO-d$_6$) δ: 9.96 (br. s., 2H), 7.82 (br. s., 1H), 7.16 (t, J=9.3 Hz, 1H), 6.92 (dd, J=13.1, 2.8 Hz, 1H), 6.79 (dt, J=8.8, 1.4 Hz, 1H), 3.73 (s, 3H).

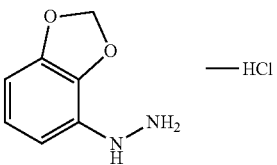

Cpd 7g: $^1$H NMR (free base, CHLOROFORM-d) δ: 6.78 (t, J=8.0 Hz, 1H), 6.56 (d, J=8.1 Hz, 1H), 6.40 (d, J=7.8 Hz, 1H), 5.89 (s, 2H).

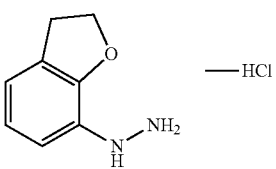

Cpd 7h: $^1$H NMR (DMSO-d$_6$) δ: 9.97 (br. s., 2H), 7.75 (br. s., 1H), 6.90 (d, J=7.1 Hz, 1H), 6.85 (d, J=8.1 Hz, 1H), 6.77-6.82 (m, 1H), 4.58 (t, J=8.7 Hz, 2H), 3.19 (t, J=8.8 Hz, 2H).

Using the intermediates prepared by Example 7 and the procedures described in Examples 1 and 2, the following compounds of the present invention were prepared:

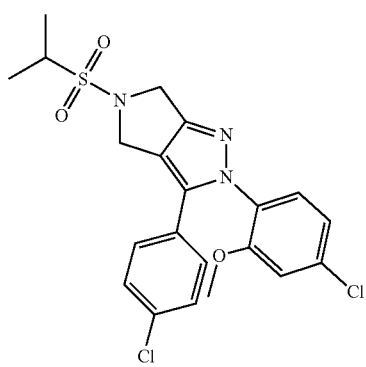

Cpd 64

Cpd 64: ¹H NMR (CHLOROFORM-d) δ: 7.34 (d, J=8.3 Hz, 1H), 7.22-7.29 (m, 2H), 6.99-7.07 (m, 3H), 6.90 (d, J=2.0 Hz, 1H), 4.70 (d, J=12.9 Hz, 4H), 3.53 (s, 3H), 3.38 (quin, J=6.8 Hz, 1H), 1.45 (d, J=7.1 Hz, 6H). ESI-MS (m/z): Calcd. for C21H21Cl2N3O3S: 466.1 (M+1). found: 466.1.

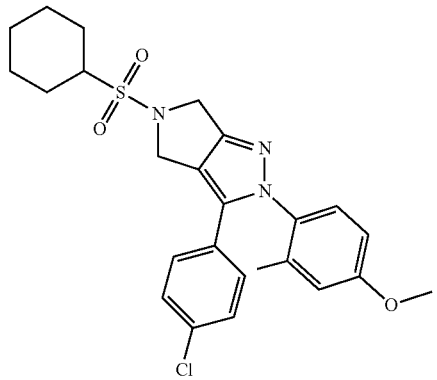

Cpd 68

Cpd 68: ¹H NMR (CHLOROFORM-d) δ: 7.20-7.25 (m, 2H), 7.14-7.20 (m, 1H), 6.94-7.00 (m, 2H), 6.75-6.80 (m, 2H), 4.74 (s, 2H), 4.67 (s, 2H), 3.83 (s, 3H), 3.05-3.17 (m, 1H), 2.17-2.28 (m, 2H), 1.96 (s, 3H), 1.91 (d, J=13.1 Hz, 2H), 1.60-1.77 (m, 3H), 1.19-1.38 (m, 4H). ESI-MS (m/z): Calcd. for C25H28ClN3O3S: 486.2 (M+1). found: 486.2.

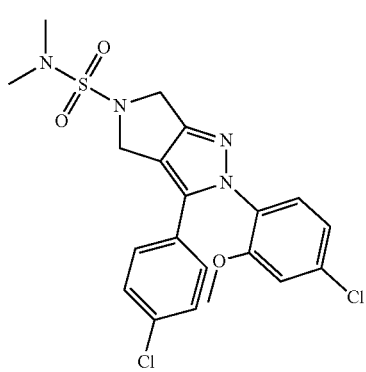

Cpd 65

Cpd 65: ¹H NMR (CHLOROFORM-d) δ: 7.34 (d, J=8.3 Hz, 1H), 7.24-7.26 (m, 2H), 7.00-7.07 (m, 3H), 6.90 (d, J=2.0 Hz, 1H), 4.58 (s, 4H), 3.53 (s, 3H), 2.90 (s, 6H). ESI-MS (m/z): Calcd. for C20H20Cl2N4O3S: 467.1 (M+1). found: 467.1.

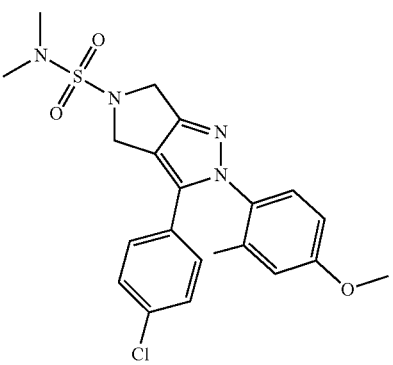

Cpd 69

Cpd 69: ¹H NMR (CHLOROFORM-d) δ: 7.20-7.26 (m, 2H), 7.14-7.19 (m, 1H), 6.94-7.01 (m, 2H), 6.74-6.80 (m, 2H), 4.66 (s, 2H), 4.58 (s, 2H), 3.83 (s, 3H), 2.91 (s, 6H), 1.96 (s, 3H). ESI-MS (m/z): Calcd. for C21H23ClN4O3S: 447.1 (M+1). found: 447.1.

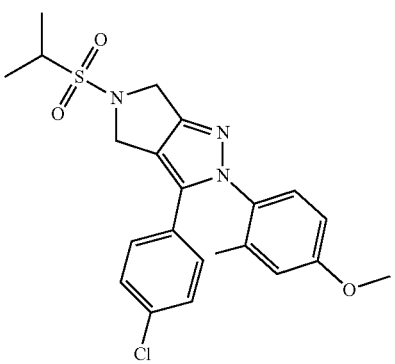

Cpd 67

Cpd 67: ¹H NMR (CHLOROFORM-d) δ: 7.20-7.26 (m, 2H), 7.14-7.19 (m, 1H), 6.94-7.02 (m, 2H), 6.74-6.81 (m, 2H), 4.75 (s, 2H), 4.68 (s, 2H), 3.83 (s, 3H), 3.40 (quin, J=6.8 Hz, 1H), 1.96 (s, 3H), 1.46 (d, J=6.8 Hz, 6H). ESI-MS (m/z): Calcd. for C22H24ClN3O3S: 446.1 (M+1). found: 446.1.

Cpd 70

Cpd 70: ¹H NMR (CHLOROFORM-d) δ: 7.36 (dd, J=8.6, 6.1 Hz, 1H), 7.23-7.29 (m, 2H), 7.00-7.06 (m, 2H), 6.76 (td, J=8.2, 2.5 Hz, 1H), 6.65 (dd, J=10.2, 2.7 Hz, 1H), 4.56-4.72 (m, 4H), 3.55 (s, 3H), 2.96 (s, 3H). ESI-MS (m/z): Calcd. for C19H17ClFN3O3S: 422.1 (M+1). found: 422.1.

Cpd 71

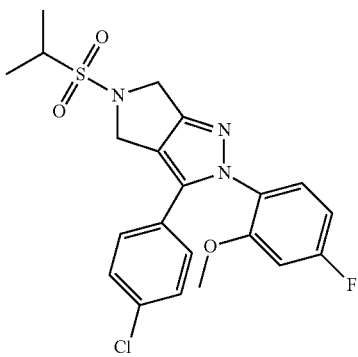

Cpd 71: ¹H NMR (CHLOROFORM-d) δ: 7.36 (dd, J=8.8, 6.1 Hz, 1H), 7.22-7.29 (m, 2H), 6.98-7.06 (m, 2H), 6.75 (td, J=8.2, 2.8 Hz, 1H), 6.65 (dd, J=10.2, 2.7 Hz, 1H), 4.61-4.80 (m, 4H), 3.55 (s, 3H), 3.38 (quin, J=6.9 Hz, 1H), 1.45 (d, J=6.8 Hz, 6H). ESI-MS (m/z): Calcd. for C21H21ClFN3O3S: 450.1 (M+1). found: 450.1.

Cpd 72

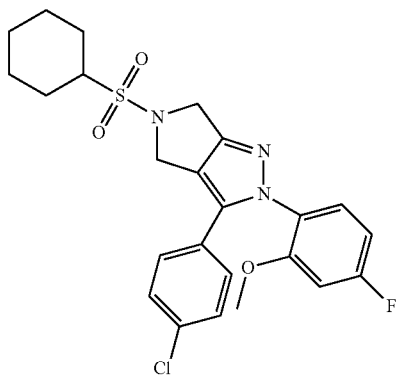

Cpd 72: ¹H NMR (CHLOROFORM-d) δ: 7.36 (dd, J=8.6, 6.1 Hz, 1H), 7.21-7.29 (m, 2H), 7.02 (d, J=8.3 Hz, 2H), 6.75 (td, J=8.2, 2.5 Hz, 1H), 6.65 (dd, J=10.4, 2.5 Hz, 1H), 4.59-4.80 (m, 4H), 3.55 (s, 3H), 3.04-3.16 (m, 1H), 2.22 (d, J=11.6 Hz, 2H), 1.91 (d, J=12.9 Hz, 2H), 1.60-1.77 (m, 3H), 1.15-1.37 (m, 3H). ESI-MS (m/z): Calcd. for C24H25ClFN3O3S: 490.1 (M+1). found: 490.1.

Cpd 73

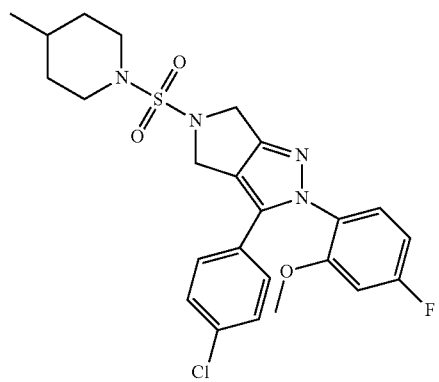

Cpd 73: ¹H NMR (CHLOROFORM-d) δ: 7.36 (dd, J=8.6, 6.1 Hz, 1H), 7.22-7.28 (m, 2H), 7.03 (d, J=8.6 Hz, 2H), 6.71-6.78 (m, 1H), 6.64 (dd, J=10.1, 2.5 Hz, 1H), 4.50-4.69 (m, 4H), 3.75 (d, J=12.1 Hz, 2H), 3.55 (s, 3H), 2.78-2.90 (m, 2H), 1.67-1.77 (m, 2H), 1.42-1.55 (m, 1H), 1.27 (qd, J=12.3, 4.0 Hz, 2H), 0.97 (d, J=6.3 Hz, 3H). ESI-MS (m/z): Calcd. for C24H26ClFN4O3S: 505.1 (M+1). found: 505.1.

Cpd 74

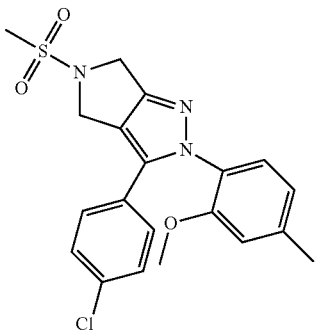

Cpd 74: ¹H NMR (CHLOROFORM-d) δ: 7.21-7.26 (m, 3H), 7.01-7.07 (m, 2H), 6.84 (d, J=8.1 Hz, 1H), 6.72 (s, 1H), 4.55-4.71 (m, 4H), 3.52 (s, 3H), 2.95 (s, 3H), 2.40 (s, 3H). ESI-MS (m/z): Calcd. for C20H20ClN3O3S: 418.1 (M+1). found: 418.1.

Cpd 75

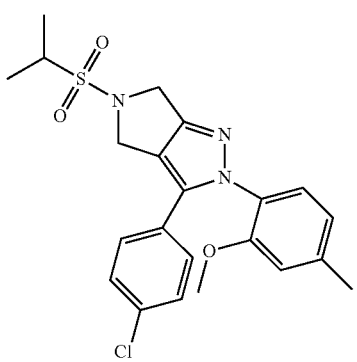

Cpd 75: ¹H NMR (CHLOROFORM-d) δ: 7.24 (dd, J=8.2, 5.9 Hz, 3H), 7.03 (d, J=8.3 Hz, 2H), 6.84 (d, J=8.1 Hz, 1H), 6.72 (s, 1H), 4.61-4.80 (m, 4H), 3.52 (s, 3H), 3.38 (dt, J=13.7, 6.9 Hz, 1H), 2.40 (s, 3H), 1.44 (d, J=6.8 Hz, 6H). ESI-MS (m/z): Calcd. for C22H24ClN3O3S: 446.1 (M+1). found: 446.1.

Cpd 76

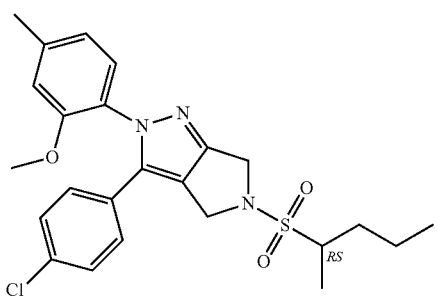

Cpd 76: ¹H NMR (CHLOROFORM-d) δ: 7.20-7.26 (m, 3H), 7.01-7.07 (m, 2H), 6.84 (d, J=8.1 Hz, 1H), 6.72 (s, 1H), 4.63-4.77 (m, 4H), 3.52 (s, 3H), 3.16-3.26 (m, 1H), 2.40 (s, 3H), 1.96-2.07 (m, 1H), 1.49-1.68 (m, 2H), 1.42 (d, J=6.8 Hz, 3H), 1.31-1.40 (m, 1H), 0.93-1.00 (m, 3H). ESI-MS (m/z): Calcd. for C24H28ClN3O3S: 474.2 (M+1). found: 474.2.

Cpd 77

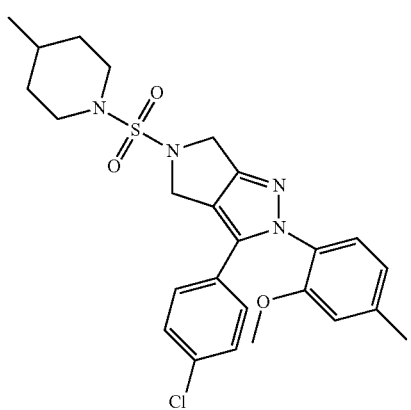

Cpd 77: ¹H NMR (CHLOROFORM-d) δ: 7.20-7.26 (m, 3H), 7.00-7.07 (m, 2H), 6.83 (d, J=7.8 Hz, 1H), 6.71 (s, 1H), 4.51-4.68 (m, 4H), 3.75 (d, J=12.4 Hz, 2H), 3.52 (s, 3H), 2.78-2.90 (m, 2H), 2.40 (s, 3H), 1.68-1.76 (m, 2H), 1.49 (ddd, J=14.3, 7.2, 3.5 Hz, 1H), 1.20-1.34 (m, 2H), 0.97 (d, J=6.3 Hz, 3H). ESI-MS (m/z): Calcd. for C25H29ClN4O3S: 501.2 (M+1). found: 501.2.

Cpd 78

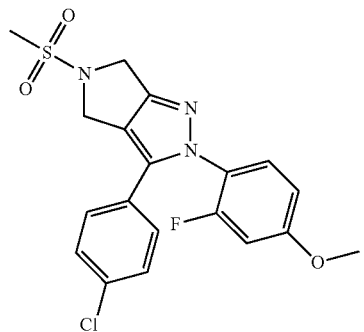

Cpd 78: ¹H NMR (CHLOROFORM-d) δ: 7.34 (t, J=8.7 Hz, 1H), 7.26-7.31 (m, 2H), 7.02-7.09 (m, 2H), 6.77 (ddd, J=8.8, 2.7, 1.1 Hz, 1H), 6.66 (dd, J=11.6, 2.8 Hz, 1H), 4.63 (d, J=4.8 Hz, 4H), 3.84 (s, 3H), 2.96 (s, 3H). ESI-MS (m/z): Calcd. for C19H17ClFN3O3S: 422.1 (M+1). found: 422.1.

Cpd 79

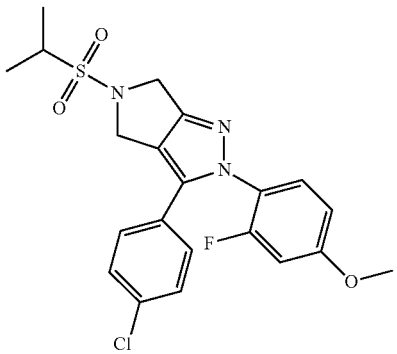

Cpd 79: ¹H NMR (CHLOROFORM-d) δ: 7.34 (t, J=8.6 Hz, 1H), 7.24-7.30 (m, 2H), 7.02-7.09 (m, 2H), 6.76 (ddd, J=8.8, 2.7, 1.1 Hz, 1H), 6.65 (dd, J=11.6, 2.5 Hz, 1H), 4.70 (dd, J=10.4, 1.5 Hz, 4H), 3.84 (s, 3H), 3.38 (quin, J=6.8 Hz, 1H), 1.45 (d, J=7.1 Hz, 6H). ESI-MS (m/z): Calcd. for C21H21ClFN3O3S: 450.1 (M+1). found: 450.1.

Cpd 80

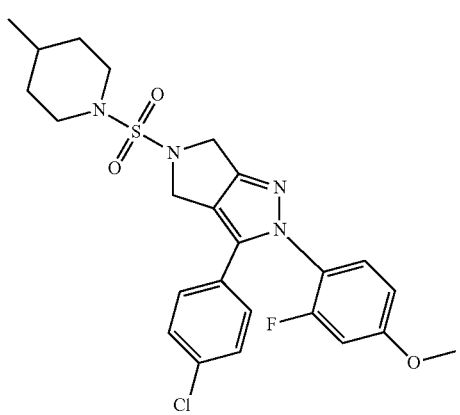

Cpd 80: ¹H NMR (CHLOROFORM-d) δ: 7.34 (t, J=8.7 Hz, 1H), 7.24-7.30 (m, 2H), 7.02-7.09 (m, 2H), 6.76 (ddd, J=8.8, 2.7, 1.1 Hz, 1H), 6.65 (dd, J=11.6, 2.8 Hz, 1H), 4.59 (dd, J=9.9, 1.5 Hz, 4H), 3.83 (s, 3H), 3.75 (d, J=12.1 Hz, 2H), 2.78-2.91 (m, 2H), 1.67-1.78 (m, 2H), 1.42-1.55 (m, 1H), 1.20-1.34 (m, 2H), 0.97 (d, J=6.6 Hz, 3H). ESI-MS (m/z): Calcd. for C24H26ClFN4O3S: 505.1 (M+1). found: 505.1.

Cpd 81

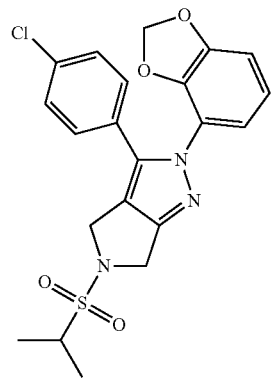

Cpd 81: ¹H NMR (CHLOROFORM-d) δ: 7.27-7.33 (m, 2H), 7.07-7.15 (m, 2H), 6.82-6.90 (m, 2H), 6.78-6.82 (m, 1H), 5.83 (s, 2H), 4.70 (d, J=3.5 Hz, 4H), 3.37 (quin, J=6.8 Hz, 1H), 1.44 (d, J=6.8 Hz, 6H). ESI-MS (m/z): Calcd. for C21H20ClN3O4S: 446.1 (M+1). found: 446.1.

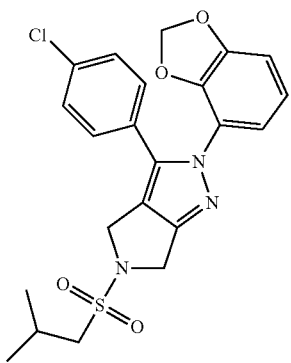

Cpd 82

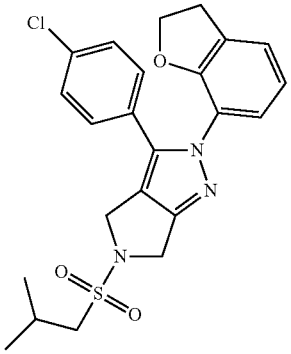

Cpd 85

Cpd 82: ¹H NMR (CHLOROFORM-d) δ: 7.20-7.25 (m, 2H), 7.01-7.07 (m, 2H), 6.75-6.82 (m, 2H), 6.73 (dd, J=6.3, 3.3 Hz, 1H), 5.75 (s, 2H), 4.57 (d, J=1.8 Hz, 4H), 2.87 (d, J=6.6 Hz, 2H), 2.28 (dt, J=13.3, 6.8 Hz, 1H), 1.07 (d, J=6.8 Hz, 6H). ESI-MS (m/z): Calcd. for C22H22ClN3O4S: 460.1 (M+1). found: 460.1.

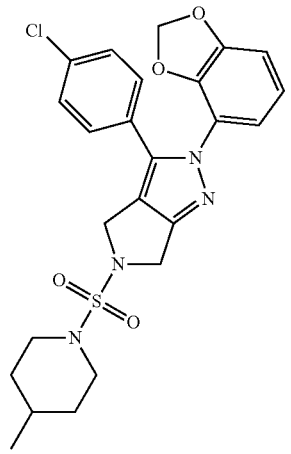

Cpd 83

Cpd 85: ¹H NMR (CHLOROFORM-d) δ: 7.20-7.29 (m, 3H), 7.03-7.12 (m, 3H), 6.84-6.90 (m, 1H), 4.64 (d, J=4.8 Hz, 4H), 4.44 (t, J=8.7 Hz, 2H), 3.23 (t, J=8.7 Hz, 2H), 2.94 (d, J=6.3 Hz, 2H), 2.35 (dt, J=13.3, 6.6 Hz, 1H), 1.14 (d, J=6.8 Hz, 6H). ESI-MS (m/z): Calcd. for C23H24ClN3O3S: 458.1 (M+1). found: 458.1.

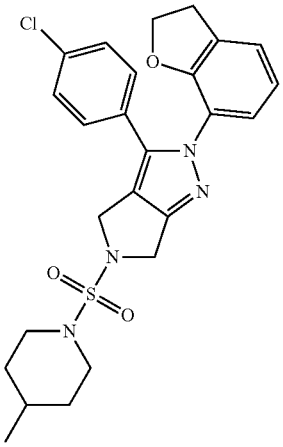

Cpd 86

Cpd 83: ¹H NMR (CHLOROFORM-d) δ: 7.27-7.32 (m, 2H), 7.08-7.15 (m, 2H), 6.83-6.89 (m, 2H), 6.77-6.83 (m, 1H), 5.82 (s, 2H), 4.59 (d, J=2.8 Hz, 4H), 3.74 (d, J=12.1 Hz, 2H), 2.84 (td, J=12.2, 2.4 Hz, 2H), 1.65-1.77 (m, 2H), 1.42-1.57 (m, 1H), 1.19-1.33 (m, 2H), 0.96 (d, J=6.6 Hz, 3H). ESI-MS (m/z): Calcd. for C24H25ClN4O4S: 501.1 (M+1). found: 501.1.

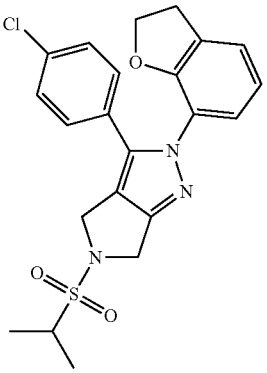

Cpd 84

Cpd 86: ¹H NMR (CHLOROFORM-d) δ: 7.19-7.29 (m, 3H), 7.02-7.13 (m, 3H), 6.83-6.91 (m, 1H), 4.59 (d, J=6.1 Hz, 4H), 4.44 (t, J=8.7 Hz, 2H), 3.74 (d, J=12.4 Hz, 2H), 3.23 (t, J=8.7 Hz, 2H), 2.83 (td, J=12.2, 2.4 Hz, 2H), 1.67-1.75 (m, 2H), 1.41-1.57 (m, 1H), 1.19-1.33 (m, 2H), 0.96 (d, J=6.3 Hz, 3H). ESI-MS (m/z): Calcd. for C25H27ClN4O3S: 499.2 (M+1). found: 499.2.

The compounds of Table 1, exemplified hereinbelow, were prepared according to the schemes and specific examples described herein.

Cpd 84: ¹H NMR (CHLOROFORM-d) δ: 7.19-7.33 (m, 3H), 7.02-7.16 (m, 3H), 6.84-6.94 (m, 1H), 4.70 (d, J=9.1 Hz, 4H), 4.44 (t, J=8.7 Hz, 2H), 3.31-3.46 (m, 1H), 3.23 (t, J=8.6 Hz, 2H), 1.44 (d, J=6.8 Hz, 6H). ESI-MS (m/z): Calcd. for C22H22ClN3O3S: 444.1 (M+1). found: 444.1.

TABLE 1

Compounds of Formula (I)

Formula (I)

| Cpd No. | R¹ | R² | R³ | Q | G |
|---|---|---|---|---|---|
| 1 | ethyl | H | H | 4-chlorophenyl | t-butyloxycarbonyl |
| 2 | ethyl | H | H | 4-chlorophenyl | methanesulfonyl |
| 3 | ethyl | H | H | 4-chlorophenyl | trifluoromethylsulfonyl |
| 4 | ethyl | H | H | 4-chlorophenyl | pyridin-3-ylcarbonyl |
| 5 | ethyl | H | H | 4-chlorophenyl | pyridin-4-ylcarbonyl |
| 6 | ethyl | H | H | 4-chlorophenyl | trifluoromethylcarbonyl |
| 7 | ethyl | H | H | 4-chlorophenyl | pyridin-2-ylcarbonyl |
| 8 | ethyl | H | H | 4-chlorophenyl | furan-2-ylcarbonyl |
| 9 | ethyl | H | H | 4-chlorophenyl | 5-methyl-isoxazol-3-ylcarbonyl |
| 10 | ethyl | H | H | 4-chlorophenyl | methoxymethylcarbonyl |
| 11 | ethyl | H | H | 4-chlorophenyl | t-butyloxycarbonylaminomethylcarbonyl |
| 12 | ethyl | H | H | 4-chlorophenyl | methanesulfonylaminomethylcarbonyl |
| 13 | ethyl | H | H | 4-chlorophenyl | trifluoromethylsulfonylaminomethylcarbonyl |
| 14 | trifluoromethyl | H | H | 4-chlorophenyl | t-butyloxycarbonyl |
| 15 | trifluoromethyl | H | H | 4-chlorophenyl | methanesulfonyl |
| 16 | trifluoromethyl | H | H | 4-chlorophenyl | isopropylsulfonyl |
| 17 | trifluoromethyl | H | H | 4-chlorophenyl | 4-methylphenylsulfonyl |
| 18 | trifluoromethyl | H | H | 4-chlorophenyl | t-butyloxycarbonylaminomethylcarbonyl |
| 19 | trifluoromethoxy | H | H | 4-chlorophenyl | t-butoxycarbonyl |
| 20 | trifluoromethoxy | H | H | 4-chlorophenyl | methanesulfonyl |
| 21 | trifluoromethoxy | H | H | 4-chlorophenyl | trifluoromethylcarbonyl |
| 22 | trifluoromethoxy | H | H | 4-chlorophenyl | t-butyloxycarbonylaminomethylcarbonyl |
| 23 | trifluoromethoxy | H | H | 4-chlorophenyl | 3-cyanophenyl |
| 24 | trifluoromethoxy | H | H | 4-chlorophenyl | 4-methoxycarbonylphenyl |
| 25 | trifluoromethoxy | H | H | 4-chlorophenyl | 4-cyanophenyl |
| 26 | trifluoromethoxy | H | H | 4-chlorophenyl | 4-(2-(morpholin-4-yl)ethylaminosulfonyl)phenyl |
| 27 | trifluoromethoxy | H | H | 4-chlorophenyl | 2-chloroquinolin-6-yl |
| 28 | methoxy | H | H | 4-chlorophenyl | t-butoxycarbonyl |
| 29 | methoxy | H | H | 4-chlorophenyl | t-butoxycarbonylaminomethylcarbonyl |
| 30 | methoxy | H | H | 4-chlorophenyl | methanesulfonyl |
| 31 | methoxy | H | H | 4-chlorophenyl | isopropylsulfonyl |
| 32 | methoxy | H | H | 4-chlorophenyl | cyclopropylsulfonyl |
| 33 | methoxy | H | H | 4-chlorophenyl | dimethylaminosulfonyl |
| 34 | methoxy | H | H | 4-chlorophenyl | dimethylaminocarbonyl |
| 35 | trifluoromethoxy | H | H | 4-chlorophenyl | isopropylsulfonyl |
| 36 | methoxy | H | H | 4-chlorophenyl | 2,2,2-trifluoroethylsulfonyl |
| 37 | methoxy | H | H | 4-chlorophenyl | cyclohexylsulfonyl |
| 38 | methoxy | H | H | 4-chlorophenyl | 2-(1H-1,3-dioxo-isoindol-2-yl)ethylsulfonyl |
| 39 | methoxy | H | H | 4-chlorophenyl | phenylmethylsulfonyl |
| 40 | methoxy | H | H | 4-chlorophenyl | cyclopentylsulfonyl |
| 41 | methoxy | H | H | 4-chlorophenyl | 1(R,S)-methyl-butyl)sulfonyl |
| 42 | methoxy | H | H | 4-chlorophenyl | 2-(2,5-dioxo-pyrrolidin-1-yl)ethylsulfonyl |
| 43 | methoxy | H | H | 4-chlorophenyl | 2-(phenyloxy)ethylsulfonyl |
| 44 | methoxy | H | H | 4-chlorophenyl | 2-(methanesulfonylamino)ethylsulfonyl |
| 45 | methoxy | H | H | 4-chlorophenyl | 2-(isopropylsulfonylamino)ethylsulfonyl |
| 46 | methoxy | H | H | 4-chlorophenyl | 2-(dimethylaminosulfonylamino)ethylsulfonyl |
| 47 | trifluoromethoxy | H | H | 4-chlorophenyl | 2-(methoxycarbonyl)ethylsulfonyl |
| 48 | trifluoromethoxy | H | H | 4-chlorophenyl | 1,1-dioxido-tetrahydrothiophen-3(R,S)-yl)sulfonyl |
| 49 | ethoxy | H | H | 4-chlorophenyl | methanesulfonyl |
| 50 | ethoxy | H | H | 4-chlorophenyl | isopropylsulfonyl |
| 51 | ethoxy | H | H | 4-chlorophenyl | cyclopentylsulfonyl |
| 52 | ethoxy | H | H | 4-chlorophenyl | cyclohexylsulfonyl |

TABLE 1-continued

Compounds of Formula (I)

Formula (I)

| Cpd No. | R¹ | R² | R³ | Q | G |
|---|---|---|---|---|---|
| 53 | ethoxy | H | H | 4-chlorophenyl | phenylmethyl-sulfonyl |
| 54 | ethoxy | H | H | 4-chlorophenyl | dimethylamino-sulfonyl |
| 55 | methoxy | H | H | 4-chlorophenyl | azepan-1-yl-sulfonyl |
| 56 | methoxy | H | H | 4-chlorophenyl | diethylamino-sulfonyl |
| 57 | methoxy | H | H | 4-chlorophenyl | 4-methyl-piperidin-1-yl-sulfonyl |
| 58 | methoxy | H | H | 4-chlorophenyl | 4-(methoxy-carbonyl)piperidin-1-yl-sulfonyl |
| 59 | methoxy | H | H | 4-chlorophenyl | morpholin-4-yl-sulfonyl |
| 60 | methoxy | H | H | 4-chlorophenyl | pyrrolidin-1-yl-sulfonyl |
| 61 | methoxy | H | H | 4-chlorophenyl | (2S,6S)-2,6-dimethyl-morpholin-4-yl-sulfonyl |
| 62 | methoxy | H | H | 4-chlorophenyl | piperidin-1-yl-sulfonyl |
| 63 | isopropyloxy | H | H | 4-chlorophenyl | dimethylamino-sulfonyl |
| 64 | methoxy | H | chloro | 4-chlorophenyl | isopropyl-sulfonyl |
| 65 | methoxy | H | chloro | 4-chlorophenyl | dimethylamino-sulfonyl |
| 66 | methyl | H | methoxy | 4-chlorophenyl | methanesulfonyl |
| 67 | methyl | H | methoxy | 4-chlorophenyl | isopropyl-sulfonyl |
| 68 | methyl | H | methoxy | 4-chlorophenyl | cyclohexyl-sulfonyl |
| 69 | methyl | H | methoxy | 4-chlorophenyl | dimethylamino-sulfonyl |
| 70 | methoxy | H | fluoro | 4-chlorophenyl | methanesulfonyl |
| 71 | methoxy | H | fluoro | 4-chlorophenyl | isopropyl-sulfonyl |
| 72 | methoxy | H | fluoro | 4-chlorophenyl | cyclohexyl-sulfonyl |
| 73 | methoxy | H | fluoro | 4-chlorophenyl | 4-methyl-piperidin-1-yl-sulfonyl |
| 74 | methoxy | H | methyl | 4-chlorophenyl | methanesulfonyl |
| 75 | methoxy | H | methyl | 4-chlorophenyl | isopropyl-sulfonyl |
| 76 | methoxy | H | methyl | 4-chlorophenyl | 1(R,S)-methylbutyl)sulfonyl |
| 77 | methoxy | H | methyl | 4-chlorophenyl | 4-methyl-piperidin-1-yl-sulfonyl |
| 78 | fluoro | H | methoxy | 4-chlorophenyl | methanesulfonyl |
| 79 | fluoro | H | methoxy | 4-chlorophenyl | isopropyl-sulfonyl |
| 80 | fluoro | H | methoxy | 4-chlorophenyl | 4-methyl-piperidin-1-ylsulfonyl |
| 81 | R² taken with R¹ and the phenyl ring to which R¹ and R² are both attached to form 1,3-benzodioxol-4-yl | | H | 4-chlorophenyl | isopropyl-sulfonyl |
| 82 | R² taken with R¹ and the phenyl ring to which R¹ and R² are both attached to form 1,3-benzodioxol-4-yl | | H | 4-chlorophenyl | (2-methyl)propylsulfonyl |
| 83 | R² taken with R¹ and the phenyl ring to which R¹ and R² are both attached to form 1,3-benzodioxol-4-yl | | H | 4-chlorophenyl | 4-methyl-piperidin-1-yl-sulfonyl |
| 84 | R² taken with R¹ and the phenyl ring to which R¹ and R² are both attached to form 2,3-dihydro-benzofuran-7-yl | | H | 4-chlorophenyl | isopropyl-sulfonyl |
| 85 | R² taken with R¹ and the phenyl ring to which R¹ and R² are both attached to form 2,3-dihydro-benzofuran-7-yl | | H | 4-chlorophenyl | (2-methyl)propyl-sulfonyl |
| 86 | R² taken with R¹ and the phenyl ring to which R¹ and R² are both attached to form 2,3-dihydro-benzofuran-7-yl | | H | 4-chlorophenyl | 4-methyl-piperidin-1-yl-sulfonyl |
| 87 | methoxy | H | H | 4-chlorophenyl | (3,5-dimethyl-isoxazol-4-yl)sulfonyl |
| 88 | dimethylamino | H | H | 4-chlorophenyl | isopropyl-sulfonyl |
| 89 | dimethylamino | H | H | 4-chlorophenyl | ethylsulfonyl |
| 90 | 2,2,2-trifluoroethoxy | H | H | 4-chlorophenyl | dimethylamino-sulfonyl |
| 91 | t-butoxy | H | H | 4-chlorophenyl | dimethylamino-sulfonyl |
| 92 | methoxy | H | H | 6-chloro-pyridin-3-yl | isopropyl-sulfonyl |
| 93 | methoxy | H | H | quinolin-3-yl | isopropyl-sulfonyl |
| 94 | methoxy | H | H | 6-methyl-pyridin-3-yl | isopropyl-sulfonyl |
| 95 | 2,2-difluoroethoxy | H | H | 4-chlorophenyl | dimethylamino-sulfonyl |
| 96 | methoxy | H | H | 6-(isopropyl-oxy)pyridin-3-yl | isopropyl-sulfonyl |

TABLE 1-continued

Compounds of Formula (I)

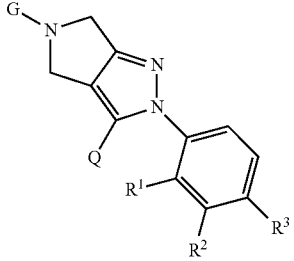

Formula (I)

| Cpd No. | R¹ | R² | R³ | Q | G |
|---|---|---|---|---|---|
| 97 | methoxy | H | H | 6-methoxy-pyridin-3-yl | isopropyl-sulfonyl |

BIOLOGICAL EXAMPLES

In Vitro Assays

Example 1

Functional Assay Antagonism of N-Type Calcium Channel

A stable cell line (HEK parent) co-expressing the $\alpha_{1B}$ (Cav2.2), $\beta_3$ and $\alpha_2\delta$ subunits of the N-type calcium channel subunits was used. These cells were routinely grown as monolayers in low glucose-containing Dulbecco's Modified Eagle Medium supplemented with 10% FBS, 2 mM L-glutamine, 100 I.U./mL penicillin, 100 µg/mL streptomycin, 400 µg/mL G418 and 200 µg/mL Zeocin (split ratio=1:5). Cells were maintained in 5% $CO_2$ at 37° C. Compounds of Formula (I) were prepared as 10 mM stocks in DMSO from neat compound, if available. Otherwise, the 5 or 10 mM DMSO stock solutions provided in-house were used.

Calcium mobilization responses to KCl depolarization were evaluated by measuring the intensity of calcium-mediated fluorescent signal in the presence of BD Calcium Assay Dye (BD Biosciences, Franklin Lakes, N.J., U.S.A.), utilizing a Functional Drug Screening System (FDSS) by Hamamatsu Corporation (Bridgewater, N.J. U.S.A.).

Twenty-four hr prior to assay, cells were seeded in clear-base poly-D-lysine-coated 384-well plates (BD Biosciences) at a density of 5,000 cells per well in culture medium and grown overnight in 5% $CO_2$ at 37° C. On the day of assay, growth media were removed, and cells were loaded with BD calcium assay dye (BD Biosciences) for 35 min at 37° C. under 5% $CO_2$ and then for 25 min at room temp. Utilizing the FDSS, cells were exposed to representative compounds of Formula (I) at varying concentrations, and intracellular calcium was measured for 5 min prior to the addition of 50 mM KCl for an additional 3 min of measurement.

Calculations and Formulas $IC_{50}$ values for representative compounds of Formula (I) were determined from six-point concentration-response experiments and represent the concentration of said compound required to inhibit 50% of the maximal response. Maximal fluorescence intensity (FI) achieved upon addition of 50 mM KCl was exported from the FDSS software and further analyzed using GraphPad Prism 3.02 (Graph Pad Software Inc., San Diego, Calif., U.S.A.). Data were normalized to the maximum average counts from quadruplicate wells for each condition in the presence of 50 mM KCl and to the minimum average counts in the presence of buffer. Theoretical curves were generated using nonlinear regression curve-fitting analysis of either sigmoidal concentration-response or sigmoidal concentration-response (variable slope), and the $IC_{50}$ values with the best-fit curve determined by GraphPad Prism were reported. Resultant data are shown in Table 2.

TABLE 2

| Compound No | FDSS $IC_{50}$ (µM) | % Inhibition (%) at 0.33 µM | % Inhibition (%) at 1 µM |
|---|---|---|---|
| 1 | 0.180 | | |
| 2 | 0.085 | | |
| 3 | 0.150 | | |
| 4 | 0.200 | | |
| 5 | 0.200 | | |
| 6 | 0.180 | | |
| 7 | | | 58 |
| 8 | 0.600 | | |
| 9 | | | 63 |
| 10 | 0.280 | | |
| 11 | 0.100 | | |
| 12 | 0.520 | | |
| 13 | | | 59 |
| 14 | | | 60 |
| 15 | 0.280 | | |
| 16 | 0.160 | | |
| 17 | 0.300 | | |
| 18 | 0.480 | | |
| 19 | 0.300 | | |
| 20 | 0.040 | | |
| 21 | 0.300 | | |
| 22 | 0.240 | | |
| 23 | | | 52 |
| 24 | | | 64 |
| 25 | | | 57 |
| 26 | | | 57 |
| 27 | 0.093 | | |
| 28 | 0.073 | | |
| 29 | 0.180 | | |
| 30 | 0.021 | | |
| 31 | 0.010 | 94 | |
| 32 | 0.021 | | |
| 33 | 0.009 | | |
| 34 | 0.170 | | |
| 35 | 0.027 | | |
| 36 | 0.015 | | |
| 37 | 0.016 | | |
| 38 | 0.053 | | |
| 39 | 0.027 | | |
| 40 | 0.012 | | |
| 41 | 0.019 | 90 | |
| 42 | 0.048 | | |
| 43 | 0.100 | | |
| 44 | 0.009 | | |
| 45 | 0.013 | | |
| 46 | 0.005 | | |
| 47 | 0.031 | | |
| 48 | 0.077 | | |
| 49 | 0.002 | | |
| 50 | 0.003 | | |
| 51 | 0.005 | | |
| 52 | 0.002 | | |
| 53 | 0.007 | | |
| 54 | 0.002 | | |
| 55 | 0.007 | | |
| 56 | 0.003 | | |
| 57 | 0.008 | 95 | |
| 58 | 0.005 | | |
| 59 | 0.002 | | |
| 60 | 0.002 | | |
| 61 | 0.005 | | |
| 62 | 0.004 | | |

TABLE 2-continued

| Compound No | FDSS IC$_{50}$ (µM) | % Inhibition (%) at 0.33 µM | % Inhibition (%) at 1 µM |
|---|---|---|---|
| 63 | 0.003 | | |
| 64 | 0.033 | 86 | |
| 65 | 0.150 | 74 | |
| 66 | | 35 | |
| 67 | 0.190 | 61 | |
| 68 | 0.130 | 71 | |
| 69 | 0.130 | 69 | |
| 70 | 0.075 | 74 | |
| 71 | 0.021 | 91 | |
| 72 | 0.095 | 82 | |
| 73 | 0.024 | 93 | |
| 74 | 0.047 | 82 | |
| 75 | 0.032 | 93 | |
| 76 | 0.021 | 90 | |
| 77 | 0.056 | 82 | |
| 78 | 0.200 | 62 | |
| 79 | 0.180 | 61 | |
| 80 | 0.140 | 62 | |
| 81 | 0.020 | 89 | |
| 82 | 0.028 | 87 | |
| 83 | 0.020 | 92 | |
| 84 | 0.010 | 94 | |
| 85 | 0.014 | 94 | |
| 86 | 0.007 | 96 | |
| 87 | 0.017 | 89 | |
| 88 | 0.005 | 96 | |
| 89 | 0.028 | 90 | |
| 90 | 0.085 | 80 | |
| 91 | 0.063 | 87 | |
| 92 | 0.016 | 86 | |
| 93 | 0.100 | | |
| 94 | | 46 | |
| 95 | 0.050 | 79 | |
| 96 | 0.130 | 79 | |
| 97 | 0.043 | 67 | |

Example 2

Automated Electrophysiology Assay

Cells were grown in T175 flasks to 50%-90% confluence. At the time of use, cells were enzymatically treated with Detachin (Genlantis, San Diego, Calif. USA), centrifuged, rinsed, and resuspended in 293 SFM II media (Life Technologies, Grand Island, N.Y. U.S.A.) supplemented with 25 mM HEPES (Sigma-Aldrich, St. Louis, Mo. U.S.A.) to a concentration of 2-3×10$^6$ cells/mL. Cells were added to the automated cell preparation station on the QPatch-HT (Sophion Biosciences, North Brunswick, N.J. U.S.A.), and following a 10- to 30-min recovery period with gentle stirring, the assay protocol was initiated. During the automated cell preparation, cells were collected, centrifuged and resuspended in an extracellular (EC) solution containing 132 mM NaCl, 1.8 mM CaCl$_2$, 5.4 mM KCl, 0.8 mM MgCl$_2$, 10 mM glucose, and 10 mM HEPES (pH=7.4), adjusted with sucrose to approximately 315 mOsm. The QPlate was primed with an intracellular solution containing 135 mM CsCl, 10 mM EGTA, 4 MgATP, 0.3 NaGTP, and 20 mM HEPES (pH=7.2), adjusted to approximately 290 mOsm with deionized water and the EC solution. Cells were added to the prepared QPlate wells by robotic pipettes of the QPatch-HT.

For cells determined to be in stable whole-cell patch clamp, the EC solution was replaced with a barium (Ba)/triethylammonium (TEA) solution containing 140 mM TEA-Cl, 10 mM BaCl$_2$, 0.8 mM MgCl$_2$, 10 mM glucose and 10 mM HEPES (pH=7.4). High (40 mM) BaCl$_2$ concentrations were made with adjustments to TEA-Cl (90 mM) to maintain the osmolarity. From a resting potential of −80 mV, a train of depolarizing pulses (15 pulses at 5 Hz, +20 mV) was delivered to the cell once every 30 sec for eight trains (4 min total), and the resulting currents were measured during a control period (no compound). This protocol was repeated for each subsequent addition of control buffer with or without compound (three periods total, each with four trains). The current generated in the 1$^{st}$ and 15$^{th}$ pulses of the last train of each period in the presence of each drug concentration was normalized to the current generated during the control period at the respective pulses (representing low- and high-frequency stimulation, respectively). Data from both the second and third drug application periods were analyzed for each cell. A final addition of Ba/TEA solution containing 60-100 µM CdCl$_2$ was made to block all N-type current and to "zero" the currents for each cell. All buffer/compound additions were made using a "spitting" feature of the QPatch-HT, which added three repetitions of 5 µL solution at the beginning of each recording period.

To examine closed-state inactivation, cells were subjected to a channel-activating 50-msec depolarizing step pulse from −80 to +10 mV, followed by a 5-sec nonactivating step to voltages ranging from −130 to −60 mV in 10 mV increments and then a 50-ms step from −80 to +10 mV to assess the remaining current. Currents from the activating voltage pulse were normalized to the peak value of the test pulse following the −130 mV step and fit to a Boltzman equation to obtain the V$_{1/2}$. Roscovitine (Sigma-Aldrich) was prepared as a 100 mM stock in dimethyl sulfoxide and diluted to the indicated working concentrations. Tetrandrine (Sigma-Aldrich) was prepared as a 4 mM stock in acidic water (pH=2.0) and then diluted to working concentrations in the external solution. ω-Conotoxin MVIIA (Sigma-Aldrich) was prepared as a 0.3 mg/mL stock solution in water, with 0.1% bovine serum albumin V (Life Technologies). Compounds of Formula (I) were diluted first into dimethyl sulfoxide and then into 10% pluronic F-127 in water (Life Technologies), sonicated for 1 min and diluted into EC buffer. Vehicle controls were run in parallel in all experiments.

Unless otherwise indicated, statistics for comparing among electrophysiological results utilized a one-way analysis of variance with Fisher's least squares determination test for pair-wise comparison. Resultant data are shown in Tables 3 and 4, below.

TABLE 3

QPatch at Low Frequency

| | % Inhibition at Various Concentrations (µM) | | | | |
|---|---|---|---|---|---|
| Cpd No. | 0.03 | 0.05 | 0.1 | 0.25 | 1 |
| 2 | | | | | −9 |
| 5 | | | | 0 | 11 |
| 6 | | | | | 16 |
| 11 | | | | 14 | 37 |
| 20 | | | | | 5 |
| 22 | | | | | 13 |
| 27 | | | | | −1 |
| 28 | | | | | 25 |
| 30 | | | | | 28 |
| 31 | | | 11 | | |
| 32 | −6 | 10 | | 57 | 74 |
| 33 | | | | | 74 |
| 35 | | | | 22 | |
| 36 | | | | 42 | |
| 37 | | | | 61 | |
| 40 | | | | 57 | |
| 41 | | | 7 | | 80 |
| 44 | | | −2 | | |
| 45 | | | 26 | | |

TABLE 3-continued

QPatch at Low Frequency

| Cpd No. | % Inhibition at Various Concentrations (μM) | | | | |
|---|---|---|---|---|---|
| | 0.03 | 0.05 | 0.1 | 0.25 | 1 |
| 46 | | | −8 | | |
| 47 | | | 8 | | |
| 49 | | | 18 | | |
| 50 | | | 42 | | |
| 51 | | | 37 | | |
| 52 | | | 40 | | |
| 54 | | | 36 | | |
| 55 | | | 25 | | |
| 56 | | | 28 | | |
| 57 | | | | | 69 |
| 58 | | | 53 | | |
| 59 | | | 28 | | |
| 60 | | | 29 | | |
| 61 | | | 53 | | |
| 62 | | | 20 | | |
| 64 | | | 12 | | |
| 65 | | | −8 | | |
| 71 | | | −30 | | |
| 73 | | | −34 | | |
| 76 | | | | −3 | |
| 81 | | | −19 | | |
| 82 | | | 4 | | |
| 83 | | | 12 | | |
| 84 | | | −3 | | |
| 85 | | | 13 | | |
| 86 | | | 20 | | |
| 87 | | | 31 | | |
| 88 | | | 26 | | |
| 89 | | | 10 | | |
| 92 | | | 14 | | |
| 95 | | | −4 | | |
| 97 | | | | | 40 |

TABLE 4

QPatch at High Frequency

| Cpd No. | % Inhibition at Various Concentrations (μM) | | | | |
|---|---|---|---|---|---|
| | 0.03 | 0.05 | 0.1 | 0.25 | 1 |
| 2 | | | | | 22 |
| 5 | | | 12 | | 37 |
| 6 | | | | | 23 |
| 11 | | | 31 | | 68 |
| 20 | | | | | 30 |
| 22 | | | | | 28 |
| 28 | | | | | 52 |
| 30 | | | | | 49 |
| 31 | | | 47 | | |
| 32 | −5 | 23 | | 64 | 83 |
| 33 | | | | | 78 |
| 35 | | | | 42 | |
| 36 | | | | 58 | |
| 37 | | | | 73 | |
| 40 | | | | 69 | |
| 41 | | | 40 | | 91 |
| 44 | | | −5 | | |
| 45 | | | 26 | | |
| 46 | | | −6 | | |
| 47 | | | 36 | | |
| 49 | | | 22 | | |
| 50 | | | 50 | | |
| 51 | | | 47 | | |
| 52 | | | 50 | | |
| 54 | | | 46 | | |
| 55 | | | 54 | | |
| 56 | | | 36 | | |
| 57 | | | | | 82 |
| 58 | | | 52 | | |
| 59 | | | 51 | | |

TABLE 4-continued

QPatch at High Frequency

| Cpd No. | % Inhibition at Various Concentrations (μM) | | | | |
|---|---|---|---|---|---|
| | 0.03 | 0.05 | 0.1 | 0.25 | 1 |
| 60 | | | 44 | | |
| 61 | | | 50 | | |
| 62 | | | 45 | | |
| 64 | | | 24 | | |
| 65 | | | 1 | | |
| 71 | | | 1 | | |
| 73 | | | −28 | | |
| 76 | | | | | 30 |
| 82 | | | 15 | | |
| 83 | | | 27 | | |
| 84 | | | 7 | | |
| 85 | | | 37 | | |
| 86 | | | 33 | | |
| 87 | | | 49 | | |
| 88 | | | 47 | | |
| 89 | | | 34 | | |
| 92 | | | 10 | | |
| 95 | | | 23 | | |
| 97 | | | | | 60 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula (I)

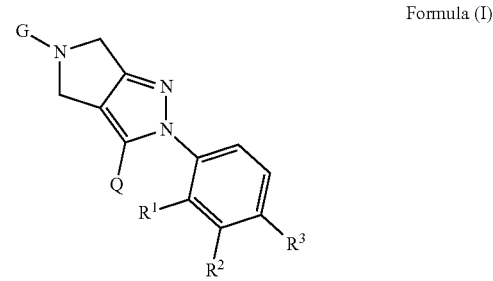

Formula (I)

wherein $R^1$ is selected from the group consisting of $C_{1-4}$alkyl, $C_{1-4}$alkoxy, 2,2-difluoroethoxy, di($C_{1-4}$alkyl)amino, trifluoromethoxy, fluoro, and trifluoromethyl;

$R^2$ is hydrogen; or, $R^2$ may be taken with $R^1$ and the phenyl ring to which $R^1$ and $R^2$ are both attached to form 2,3-dihydrobenzofuran-7-yl or 1,3-benzodioxol-4-yl;

$R^3$ is hydrogen, methyl, methoxy, chloro, or fluoro;

Q is selected from the group consisting of Q1, Q2, and Q3;

Q1
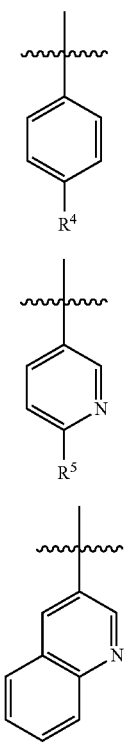

Q2

Q3 wherein
R⁴ is selected from the group consisting of hydrogen, $C_{1-4}$alkyl, $C_{1-4}$alkoxy, cyano, fluoro, and chloro;
R⁵ is independently selected from the group consisting of hydrogen, $C_{1-4}$alkyl, $C_{1-4}$alkoxy, cyano, chloro, and di($C_{1-4}$alkyl)amino;
G is selected from the group consisting of 4-methylphenyl, 3-cyanophenyl, 4-cyanophenyl, 4-methoxycarbonylphenyl, 2-chloro-quinolin-6-yl, morpholin-4-ylsulfonyl, morpholin-4-yl($C_{1-4}$alkyl)aminosulfonyl, 2,6-dimethylmorpholin-4-ylsulfonyl, $C_{6-10}$aryl($C_{1-4}$alkylsulfonyl, $C_{6-10}$aryloxy($C_{1-4}$)alkylsulfonyl, 3,5-dimethylisoxazol-4-yl-sulfonyl, $C_{1-4}$alkoxycarbonyl($C_{1-4}$)alkyl-sulfonyl, trifluoromethylsulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkyl-sulfonyl, $C_{1-4}$alkylsulfonylamino($C_{1-4}$alkyl-sulfonyl, 2,5-dione-pyrrolidin-1-yl-($C_{1-4}$alkylsulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R⁶)-piperidin-1-ylsulfonyl wherein R⁶ is $C_{1-4}$alkoxycarbonyl or $C_{1-4}$alkyl; azepan-1-ylsulfonyl, methoxymethylcarbonyl, trifluoromethylcarbonyl, $C_{1-4}$alkoxycarbonylamino ($C_{2-4}$)alkyl-carbonyl, $C_{1-4}$alkoxycarbonylaminomethylcarbonyl, trifluoromethylsulfonylaminomethylcarbonyl, trifluoromethoxycarbonyl, $C_{1-4}$alkylsulfonylaminomethyl-carbonyl, $C_{1-4}$alkoxycarbonyl, di($C_{1-4}$alkyl)aminocarbonyl, $C_{1-4}$alkoxycarbonyl, pyridinylcarbonyl, furanylcarbonyl, and 5-methylisoxazol-3-ylcarbonyl;
or an enantiomer, diastereomer, or pharmaceutically acceptable salt thereof.

2. The compound of claim 1 wherein R¹ is selected from the group consisting of $C_{1-4}$alkyl, $C_{1-4}$alkoxy, 2,2-difluoroethoxy, di($C_{1-4}$alkyl)amino, and trifluoromethoxy.

3. The compound of claim 2 wherein R¹ is selected from the group consisting of ethyl, methoxy, ethoxy, isopropyloxy, difluoroethoxy, dimethylamino, and trifluoromethoxy.

4. The compound of claim 1 wherein R³ is hydrogen, methyl, chloro, or fluoro.

5. The compound of claim 1 wherein Q is selected from the group consisting of Q1, Q2, and Q3;

Q1
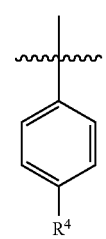

Q2
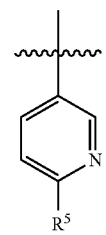

Q3
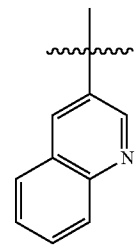

wherein
R⁴ is chloro;
R⁵ is independently selected from the group consisting of $C_{1-4}$alkyl, $C_{1-4}$alkoxy, and chloro.

6. The compound of claim 5 wherein Q is selected from the group consisting of Q1, Q2, and Q3;

Q1
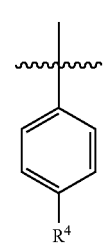

-continued

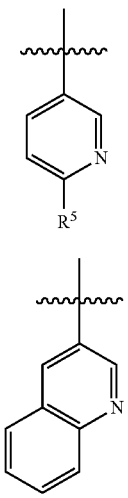

wherein
R[4] is chloro;
R[5] is independently selected from the group consisting of $C_{1-4}$alkoxy and chloro.

7. The compound of claim 1 wherein G is selected from the group consisting of 4-methylphenyl, 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, trifluoromethylsulfonyl, $C_{1-4}$alkoxycarbonyl($C_{1-4}$alkyl-sulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$alkyl-sulfonyl, $C_{1-4}$alkylsulfonylamino($C_{1-4}$alkylsulfonyl, 2,5-dione-pyrrolidin-1-yl-($C_{1-4}$)alkyl-sulfonyl, (2H)-1,3-dione-1H-isoindol-1-yl-($C_{1-4}$)alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R[6])-piperidin-1-ylsulfonyl wherein R[6] is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, $C_{1-4}$alkylsulfonylaminomethyl-carbonyl, $C_{1-4}$alkoxycarbonyl, di($C_{1-4}$alkyl)aminocarbonyl, $C_{1-4}$alkoxycarbonyl, pyridinylcarbonyl, and furanylcarbonyl.

8. The compound of claim 7 wherein G is selected from the group consisting of methylphenyl, 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, 4-$C_{1-4}$alkoxycarbonyl($C_{1-4}$)alkyl-sulfonyl, trifluoromethylsulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$)alkyl-sulfonyl, $C_{1-4}$alkylsulfonylamino($C_{1-4}$)alkylsulfonyl, 2,5-dione-pyrrolidin-1-yl-($C_{1-4}$)alkyl-sulfonyl, (2H)-1,3-dione-1H-isoindol-1-yl-($C_{1-4}$)alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R[6])-piperidin-1-ylsulfonyl wherein R[6] is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, $C_{1-4}$alkoxycarbonyl, di($C_{1-4}$alkyl)aminocarbonyl, $C_{1-4}$alkoxycarbonyl, and pyridinylcarbonyl.

9. The compound of claim 8 wherein G is selected from the group consisting of 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, $C_{1-4}$alkoxycarbonyl($C_{1-4}$)alkylsulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$)alkyl-sulfonyl, $C_{1-4}$alkylsulfonylamino($C_{1-4}$)alkylsulfonyl, 2,5-dione-pyrrolidin-1-yl-($C_{1-4}$)alkyl-sulfonyl, (2H)-1,3-dione-1H-isoindol-1-yl-($C_{1-4}$)alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R[6])-piperidin-1-ylsulfonyl wherein R[6] is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, $C_{1-4}$alkoxycarbonylamino($C_{2-4}$)alkyl-carbonyl, and $C_{1-4}$alkoxycarbonyl.

10. The compound of Formula (I) as in claim 1

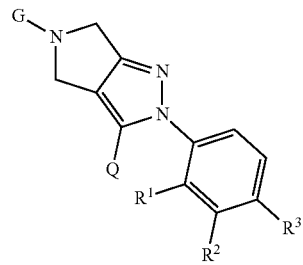

Formula (I)

wherein
R[1] is selected from the group consisting of $C_{1-4}$alkyl, $C_{1-4}$alkoxy, 2,2-difluoroethoxy, di($C_{1-4}$alkyl)amino, trifluoromethoxy, fluoro, and trifluoromethyl;

R[2] is hydrogen; or, R[2] may be taken with R[1] and the phenyl ring to which R[1] and R[2] are both attached to form 2,3-dihydrobenzofuran-7-yl or 1,3-benzodioxol-4-yl;

R[3] is hydrogen, methyl, methoxy, chloro, or fluoro;

Q is selected from the group consisting of Q1, Q2, and Q3;

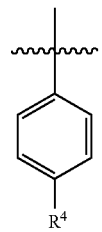

Q1

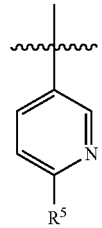

Q2

-continued

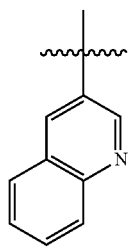

Q3 wherein
R⁴ is selected from the group consisting of chloro;
R⁵ is independently selected from the group consisting of $C_{1-4}$alkoxy and chloro;
G is selected from the group consisting of 4-methylphenyl, 2-chloroquinolin-6-yl, $C_{6-10}$ aryl($C_{1-4}$)alkylsulfonyl, $C_{6-10}$aryloxy($C_{1-4}$)alkylsulfonyl, 3,5-dimethylisoxazol-4-yl-sulfonyl, trifluoromethylsulfonyl, $C_{1-4}$alkoxycarbonyl($C_{1-4}$)alkyl-sulfonyl, $C_{3-7}$cycloalkylsulfonyl, 2,2,2-trifluoroethylsulfonyl, di($C_{1-4}$-alkyl)aminosulfonyl, di($C_{1-4}$alkyl)aminosulfonylamino($C_{1-4}$alkyl-sulfonyl, $C_{1-4}$alkylsulfonylamino($C_{1-4}$)alkyl-sulfonyl, 2,5-dione-pyrrolidin-1-yl-($C_{1-4}$)alkylsulfonyl, (2H)-1,3-dione-1H-isoindol-1-yl-($C_{1-4}$)alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R⁶)-piperidin-1-ylsulfonyl wherein R⁶ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, $C_{1-4}$alkylsulfonylaminomethyl-carbonyl, $C_{1-4}$alkoxycarbonyl, di($C_{1-4}$alkyl)aminocarbonyl, $C_{1-4}$alkoxycarbonyl, pyridinylcarbonyl, and furanylcarbonyl;
or an enantiomer, diastereomer, or pharmaceutically acceptable salt thereof.

11. The compound of Formula (I) as in claim 1

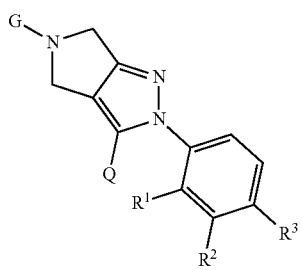

Formula (I)

wherein
R¹ is selected from the group consisting of $C_{1-4}$alkyl, $C_{1-4}$alkoxy, 2,2-difluoroethoxy, di($C_{1-4}$alkyl)amino, trifluoromethoxy, fluoro, and trifluoromethyl;
R² is hydrogen; or, R² may be taken with R¹ and the phenyl ring to which R¹ and R² are both attached to form 2,3-dihydrobenzofuran-7-yl or 1,3-benzodioxol-4-yl;
R³ is hydrogen, methyl, methoxy, chloro, or fluoro;

Q is selected from the group consisting of Q1, Q2, and Q3;

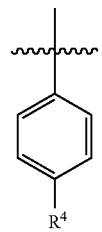

Q1

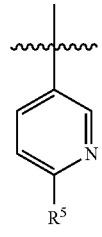

Q2

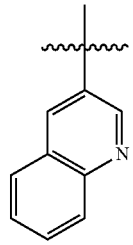

Q3 wherein
R⁴ is chloro;
R⁵ is independently selected from the group consisting of $C_{1-4}$alkoxy and chloro;
G is selected from the group consisting of methylphenyl, 2-chloro-quinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, 4-$C_{1-4}$alkoxycarbonyl($C_{1-4}$) alkyl-sulfonyl, trifluoromethylsulfonyl, $C_{3-7}$cycloalkylsulfonyl, 2,2,2-trifluoroethylsulfonyl, di($C_{1-4}$-alkyl)aminosulfonyl, di($C_{1-4}$alkyl)aminosulfonylamino($C_{1-4}$alkyl-sulfonyl, $C_{1-4}$alkylsulfonylamino($C_{1-4}$alkyl-sulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R⁶)-piperidin-1-ylsulfonyl wherein R⁶ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, methoxymethylcarbonyl, trifluoromethylcarbonyl, $C_{1-4}$alkoxycarbonylamino($C_{2-4}$)alkyl-carbonyl, $C_{1-4}$alkoxycarbonylaminomethyl-carbonyl, $C_{1-4}$alkoxycarbonyl, di($C_{1-4}$alkyl)aminocarbonyl, $C_{1-4}$alkoxycarbonyl, and pyridinylcarbonyl;
or an enantiomer, diastereomer, or pharmaceutically acceptable salt thereof.

12. The compound of Formula (I) as in claim 1

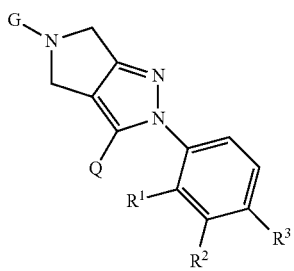
Formula (I)

wherein
- $R^1$ is selected from the group consisting of ethyl, methoxy, ethoxy, isopropyloxy, difluoroethoxy, dimethylamino, and trifluoromethoxy;
- $R^2$ is hydrogen; or, $R^2$ may be taken with $R^1$ and the phenyl ring to which $R^1$ and $R^2$ are both attached to form 2,3-dihydrobenzofuran-7-yl or 1,3-benzodioxol-4-yl;
- $R^3$ is hydrogen, methyl, chloro, or fluoro;
- Q is selected from the group consisting of Q1, Q2, and Q3;

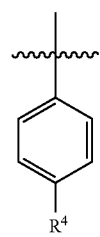
Q1

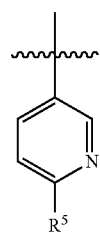
Q2

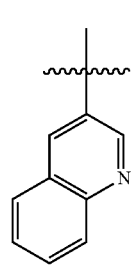
Q3 wherein
- $R^4$ is chloro;
- $R^5$ is independently selected from the group consisting of $C_{1-4}$alkoxy and chloro;
- G is selected from the group consisting of 2-chloroquinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, $C_{1-4}$alkoxycarbonyl($C_{1-4}$alkyl-sulfonyl, $C_{3-7}$cycloalkylsulfonyl, 2,2,2-trifluoroethylsulfonyl, di($C_{1-4}$alkyl)aminosulfonyl, di($C_{1-4}$alkyl)aminosulfonylamino($C_{1-4}$)alkyl-sulfonyl, $C_{1-4}$alkylsulfonylamino($C_{1-4}$)alkylsulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-($R^6$)-piperidin-1-ylsulfonyl wherein $R^6$ is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, $C_{1-4}$alkoxycarbonylamino($C_{2-4}$)alkyl-carbonyl, and $C_{1-4}$alkoxycarbonyl;

or an enantiomer, diastereomer, or pharmaceutically acceptable salt thereof.

13. The compound of Formula (I) as in claim 1

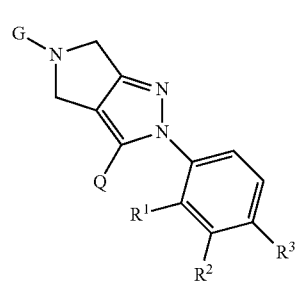
Formula (I)

wherein
- $R^1$ is selected from the group consisting of ethyl, methoxy, ethoxy, isopropyloxy, difluoroethoxy, dimethylamino, and trifluoromethoxy;
- $R^2$ is hydrogen;
- $R^3$ is hydrogen, methyl, chloro, or fluoro;
- Q is selected from the group consisting of Q1, Q2, and Q3;

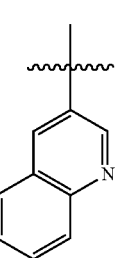
Q1

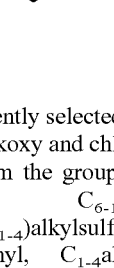
Q2

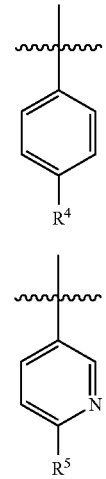

-continued

Q3

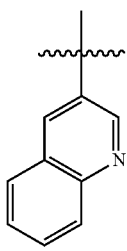

wherein
R[4] is chloro;
R[5] is independently selected from the group consisting of $C_{1-4}$alkoxy and chloro;
G is selected from the group consisting of 2-chloroquinolin-6-yl, $C_{6-10}$aryl($C_{1-4}$)alkylsulfonyl, $C_{6-10}$aryloxy($C_{1-4}$)alkylsulfonyl, 3,5-dimethylisoxazol-4-yl-sulfonyl, $C_{1-4}$alkoxycarbonyl($C_{1-4}$)alkylsulfonyl, $C_{3-7}$cycloalkylsulfonyl, 2,2,2-trifluoroethylsulfonyl, di($C_{1-4}$alkyl)aminosulfonyl, di($C_{1-4}$alkyl) aminosulfonylamino($C_{1-4}$alkyl-sulfonyl, $C_{1-4}$alkylsulfonylamino($C_{1-4}$alkyl-sulfonyl, 2,5-dione-pyrrolidin-1-yl-($C_{1-4}$alkyl-sulfonyl, (2H)-1,3-dione-1H-isoindol-1-yl-($C_{1-4}$alkyl-sulfonyl, 1,1-dioxidotetrahydrothiophen-3-yl)sulfonyl, $C_{1-6}$alkylsulfonyl, di($C_{1-4}$alkyl)aminosulfonyl, pyrrolidin-1-ylsulfonyl, piperidin-1-ylsulfonyl, 4-(R[6])-piperidin-1-ylsulfonyl wherein R[6] is $C_{1-4}$alkoxycarbonyl or $C_{1-4}$alkyl; azepan-1-ylsulfonyl, morpholin-4-ylsulfonyl, 2,6-dimethylmorpholin-4-ylsulfonyl, $C_{1-4}$alkoxycarbonylamino($C_{2-4}$)alkyl-carbonyl, and $C_{1-4}$alkoxycarbonyl;
or an enantiomer, diastereomer, or pharmaceutically acceptable salt thereof.

14. The compound of Formula (I) as in claim 1

Formula (I)

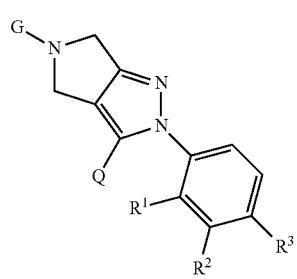

selected from the group consisting of
tert-Butyl 3-(4-chlorophenyl)-2-(2-ethylphenyl)-2,6-dihydropyrrolo[3,4-c]pyrazole-5(4H)-carboxylate;
3-(4-Chlorophenyl)-2-(2-ethylphenyl)-5-(methylsulfonyl)-2,4,5,6-tetrahydropyrrolo[3,4-c]pyrazole;
3-(4-Chlorophenyl)-2-(2-ethylphenyl)-5-[(trifluoromethyl)sulfonyl]-2,4,5,6-tetrahydropyrrolo[3,4-c]pyrazole;
3-(4-Chlorophenyl)-2-(2-ethylphenyl)-5-(pyridin-3-ylcarbonyl)-2,4,5,6-tetrahydropyrrolo[3,4-c]pyrazole;
3-(4-Chlorophenyl)-2-(2-ethylphenyl)-5-(pyridin-4-ylcarbonyl)-2,4,5,6-tetrahydropyrrolo[3,4-c]pyrazole;
3-(4-Chlorophenyl)-2-(2-ethylphenyl)-5-(trifluoroacetyl)-2,4,5,6-tetrahydropyrrolo[3,4-c]pyrazole;
3-(4-Chlorophenyl)-2-(2-ethylphenyl)-5-(pyridin-2-ylcarbonyl)-2,4,5,6-tetrahydropyrrolo[3,4-c]pyrazole;
3-(4-Chlorophenyl)-2-(2-ethylphenyl)-5-(furan-2-ylcarbonyl)-2,4,5,6-tetrahydropyrrolo[3,4-c]pyrazole;
3-(4-Chlorophenyl)-2-(2-ethylphenyl)-5-[(5-methylisoxazol-3-yl)carbonyl]-2,4,5,6-tetrahydropyrrolo[3,4-c]pyrazole;
3-(4-Chlorophenyl)-2-(2-ethylphenyl)-5-(methoxyacetyl)-2,4,5,6-tetrahydropyrrolo[3,4-c]pyrazole;
tert-Butyl{2-[3-(4-chlorophenyl)-2-(2-ethylphenyl)-2,6-dihydropyrrolo[3,4-c]pyrazol-5(4H)-yl]-2-oxoethyl}carbamate;
N-{2-[3-(4-Chlorophenyl)-2-(2-ethylphenyl)-2,6-dihydropyrrolo[3,4-c]pyrazol-5(4H)-yl]-2-oxoethyl}methanesulfonamide;
N-{2-[3-(4-Chlorophenyl)-2-(2-ethylphenyl)-2,6-dihydropyrrolo[3,4-c]pyrazol-5(4H)-yl]-2-oxoethyl}-1,1,1-trifluoromethanesulfonamide;
tert-Butyl 3-(4-chlorophenyl)-2-[2-(trifluoromethyl)phenyl]-2,6-dihydropyrrolo[3,4-c]pyrazole-5(4H)-carboxylate;
3-(4-Chlorophenyl)-5-(methylsulfonyl)-2-[2-(trifluoromethyl)phenyl]-2,4,5,6-tetrahydropyrrolo[3,4-c]pyrazole;
3-(4-Chlorophenyl)-5-[(1-methylethyl)sulfonyl]-2-[2-(trifluoromethyl)phenyl]-2,4,5,6-tetrahydropyrrolo[3,4-c]pyrazole;
3-(4-Chlorophenyl)-5-[(4-methylphenyl)sulfonyl]-2-[2-(trifluoromethyl)phenyl]-2,4,5,6-tetrahydropyrrolo[3,4-c]pyrazole;
tert-Butyl{2-[3-(4-chlorophenyl)-2-[2-(trifluoromethyl)phenyl]-2,6-dihydropyrrolo[3,4-c]pyrazol-5(4H)-yl]-2-oxoethyl}carbamate;
tert-Butyl 3-(4-chlorophenyl)-2-[2-(trifluoromethoxy)phenyl]-2,6-dihydropyrrolo[3,4-c]pyrazole-5(4H)-carboxylate;
3-(4-Chlorophenyl)-5-(methylsulfonyl)-2-[2-(trifluoromethoxy)phenyl]-2,4,5,6-tetrahydropyrrolo[3,4-c]pyrazole;
3-(4-Chlorophenyl)-5-(trifluoroacetyl)-2-[2-(trifluoromethoxy)phenyl]-2,4,5,6-tetrahydropyrrolo[3,4-c]pyrazole;
tert-Butyl{2-[3-(4-chlorophenyl)-2-[2-(trifluoromethoxy)phenyl]-2,6-dihydropyrrolo[3,4-c]pyrazol-5 (4H)-yl]-2-oxoethyl}carbamate;
3-[3-(4-Chlorophenyl)-2-[2-(trifluoromethoxy)phenyl]-2,6-dihydropyrrolo[3,4-c]pyrazol-5(4H)-yl]benzonitrile;
Methyl 4-[3-(4-chlorophenyl)-2-[2-(trifluoromethoxy)phenyl]-2,6-dihydropyrrolo[3,4-c]pyrazol-5(4H)-yl]benzoate;
4-[3-(4-Chlorophenyl)-2-[2-(trifluoromethoxy)phenyl]-2,6-dihydropyrrolo[3,4-c]pyrazol-5(4H)-yl]benzonitrile;
4-[3-(4-Chlorophenyl)-2-[2-(trifluoromethoxy)phenyl]-2,6-dihydropyrrolo[3,4-c]pyrazol-5(4H)-yl]-N-(2-morpholin-4-ylethyl)benzenesulfonamide;
2-Chloro-6-[3-(4-chlorophenyl)-2-[2-(trifluoromethoxy)phenyl]-2,6-dihydropyrrolo[3,4-c]pyrazol-5(4H)-yl]quinoline;
tert-Butyl 3-(4-chlorophenyl)-2-(2-methoxyphenyl)-2,6-dihydropyrrolo[3,4-c]pyrazole-5(4H)-carboxylate;
tert-Butyl{2-[3-(4-chlorophenyl)-2-(2-methoxyphenyl)-2,6-dihydropyrrolo[3,4-c]pyrazol-5 (4H)-yl]-2-oxo ethyl}carbamate;
3-(4-Chlorophenyl)-2-(2-methoxyphenyl)-5-(methylsulfonyl)-2,4,5,6-tetrahydropyrrolo[3,4-c]pyrazole;

3-(4-Chlorophenyl)-2-(2-methoxyphenyl)-5-[(1-methylethyl)sulfonyl]-2,4,5,6-tetrahydropyrrolo[3,4-c]pyrazole;
3-(4-Chlorophenyl)-5-(cyclopropylsulfonyl)-2-(2-methoxyphenyl)-2,4,5,6-tetrahydropyrrolo[3,4-c]pyrazole;
3-(4-Chlorophenyl)-2-(2-methoxyphenyl)-N,N-dimethyl-2,6-dihydropyrrolo[3,4-c]pyrazole-5(4H)-sulfonamide;
3-(4-Chlorophenyl)-2-(2-methoxyphenyl)-N,N-dimethyl-2,6-dihydropyrrolo[3,4-c]pyrazole-5(4H)-carboxamide;
3-(4-Chlorophenyl)-5-[(1-methylethyl)sulfonyl]-2-[2-(trifluoromethoxy)phenyl]-2,4,5,6-tetrahydropyrrolo[3,4-c]pyrazole;
3-(4-Chlorophenyl)-2-(2-methoxyphenyl)-5-[(2,2,2-trifluoroethyl)sulfonyl]-2,4,5,6-tetrahydropyrrolo[3,4-c]pyrazole;
3-(4-Chlorophenyl)-5-(cyclohexylsulfonyl)-2-(2-methoxyphenyl)-2,4,5,6-tetrahydropyrrolo[3,4-c]pyrazole;
2-(2-{[3-(4-Chlorophenyl)-2-(2-methoxyphenyl)-2,6-dihydropyrrolo[3,4-c]pyrazol-5(4H)-yl]sulfonyl}ethyl)-1H-isoindole-1,3(2H)-dione;
5-(Benzylsulfonyl)-3-(4-chlorophenyl)-2-(2-methoxyphenyl)-2,4,5,6-tetrahydropyrrolo[3,4-c]pyrazole;
3-(4-Chlorophenyl)-5-(cyclopentylsulfonyl)-2-(2-methoxyphenyl)-2,4,5,6-tetrahydropyrrolo[3,4-c]pyrazole;
3-(4-Chlorophenyl)-2-(2-methoxyphenyl)-5-[(1-methylbutyl)sulfonyl]-2,4,5,6-tetrahydropyrrolo[3,4-c]pyrazole;
1-(2-{[3-(4-Chlorophenyl)-2-(2-methoxyphenyl)-2,6-dihydropyrrolo[3,4-c]pyrazol-5(4H)-yl]sulfonyl}ethyl)pyrrolidine-2,5-dione;
3-(4-Chlorophenyl)-2-(2-methoxyphenyl)-5-[(2-phenoxyethyl)sulfonyl]-2,4,5,6-tetrahydropyrrolo[3,4-c]pyrazole;
N-(2-{[3-(4-Chlorophenyl)-2-(2-methoxyphenyl)-2,6-dihydropyrrolo[3,4-c]pyrazol-5(4H)-yl]sulfonyl}ethyl)methanesulfonamide;
N-(2-{[3-(4-Chlorophenyl)-2-(2-methoxyphenyl)-2,6-dihydropyrrolo[3,4-c]pyrazol-5(4H)-yl]sulfonyl}ethyl)propane-2-sulfonamide;
N'-(2-{[3-(4-Chlorophenyl)-2-(2-methoxyphenyl)-2,6-dihydropyrrolo[3,4-c]pyrazol-5(4H)-yl]sulfonyl}ethyl)-N,N-dimethylsulfamide;
Methyl 3-{[3-(4-chlorophenyl)-2-[2-(trifluoromethoxy)phenyl]-2,6-dihydropyrrolo[3,4-c]pyrazol-5(4H)-yl]sulfonyl}propanoate;
3-(4-Chlorophenyl)-5-[(1,1-dioxidotetrahydrothiophen-3-yl)sulfonyl]-2-[2-(trifluoromethoxy)phenyl]-2,4,5,6-tetrahydropyrrolo[3,4-c]pyrazole;
3-(4-Chlorophenyl)-2-(2-ethoxyphenyl)-5-(methylsulfonyl)-2,4,5,6-tetrahydropyrrolo[3,4-c]pyrazole;
3-(4-Chlorophenyl)-2-(2-ethoxyphenyl)-5-[(1-methylethyl)sulfonyl]-2,4,5,6-tetrahydropyrrolo[3,4-c]pyrazole;
3-(4-Chlorophenyl)-5-(cyclopentylsulfonyl)-2-(2-ethoxyphenyl)-2,4,5,6-tetrahydropyrrolo[3,4-c]pyrazole;
3-(4-Chlorophenyl)-5-(cyclohexylsulfonyl)-2-(2-ethoxyphenyl)-2,4,5,6-tetrahydropyrrolo[3,4-c]pyrazole;
5-(Benzylsulfonyl)-3-(4-chlorophenyl)-2-(2-ethoxyphenyl)-2,4,5,6-tetrahydropyrrolo[3,4-c]pyrazole;
3-(4-Chlorophenyl)-2-(2-ethoxyphenyl)-N,N-dimethyl-2,6-dihydropyrrolo[3,4-c]pyrazole-5(4H)-sulfonamide;
5-(Azepan-1-ylsulfonyl)-3-(4-chlorophenyl)-2-(2-methoxyphenyl)-2,4,5,6-tetrahydropyrrolo[3,4-c]pyrazole;
3-(4-Chlorophenyl)-N,N-diethyl-2-(2-methoxyphenyl)-2,6-dihydropyrrolo[3,4-c]pyrazole-5(4H)-sulfonamide;
3-(4-Chlorophenyl)-2-(2-methoxyphenyl)-5-[(4-methylpiperidin-1-yl)sulfonyl]-2,4,5,6-tetrahydropyrrolo[3,4-c]pyrazole;
Methyl 1-{[3-(4-chlorophenyl)-2-(2-methoxyphenyl)-2,6-dihydropyrrolo[3,4-c]pyrazol-5(4H)-yl]sulfonyl}piperidine-4-carboxylate;
3-(4-Chlorophenyl)-2-(2-methoxyphenyl)-5-(morpholin-4-ylsulfonyl)-2,4,5,6-tetrahydropyrrolo[3,4-c]pyrazole;
3-(4-Chlorophenyl)-2-(2-methoxyphenyl)-5-(pyrrolidin-1-ylsulfonyl)-2,4,5,6-tetrahydropyrrolo[3,4-c]pyrazole;
3-(4-Chlorophenyl)-5-{[(2S,6S)-2,6-dimethylmorpholin-4-yl]sulfonyl}-2-(2-methoxyphenyl)-2,4,5,6-tetrahydropyrrolo[3,4-c]pyrazole;
3-(4-Chlorophenyl)-2-(2-methoxyphenyl)-5-(piperidin-1-ylsulfonyl)-2,4,5,6-tetrahydropyrrolo[3,4-c]pyrazole;
3-(4-Chlorophenyl)-N,N-dimethyl-2-[2-(1-methylethoxy)phenyl]-2,6-dihydropyrrolo[3,4-c]pyrazole-5(4H)-sulfonamide;
2-(4-Chloro-2-methoxyphenyl)-3-(4-chlorophenyl)-5-[(1-methylethyl)sulfonyl]-2,4,5,6-tetrahydropyrrolo[3,4-c]pyrazole;
2-(4-Chloro-2-methoxyphenyl)-3-(4-chlorophenyl)-N,N-dimethyl-2,6-dihydropyrrolo[3,4-c]pyrazole-5(4H)-sulfonamide;
3-(4-Chlorophenyl)-2-(4-methoxy-2-methylphenyl)-5-(methylsulfonyl)-2,4,5,6-tetrahydropyrrolo[3,4-c]pyrazole;
3-(4-Chlorophenyl)-2-(4-methoxy-2-methylphenyl)-5-[(1-methylethyl)sulfonyl]-2,4,5,6-tetrahydropyrrolo[3,4-c]pyrazole;
3-(4-Chlorophenyl)-5-(cyclohexylsulfonyl)-2-(4-methoxy-2-methylphenyl)-2,4,5,6-tetrahydropyrrolo[3,4-c]pyrazole;
3-(4-Chlorophenyl)-2-(4-methoxy-2-methylphenyl)-N,N-dimethyl-2,6-dihydropyrrolo[3,4-c]pyrazole-5(4H)-sulfonamide;
3-(4-Chlorophenyl)-2-(4-fluoro-2-methoxyphenyl)-5-(methylsulfonyl)-2,4,5,6-tetrahydropyrrolo[3,4-c]pyrazole;
3-(4-Chlorophenyl)-2-(4-fluoro-2-methoxyphenyl)-5-[(1-methylethyl)sulfonyl]-2,4,5,6-tetrahydropyrrolo[3,4-c]pyrazole;
3-(4-Chlorophenyl)-5-(cyclohexylsulfonyl)-2-(4-fluoro-2-methoxyphenyl)-2,4,5,6-tetrahydropyrrolo[3,4-c]pyrazole;
3-(4-Chlorophenyl)-2-(4-fluoro-2-methoxyphenyl)-5-[(4-methylpiperidin-1-yl)sulfonyl]-2,4,5,6-tetrahydropyrrolo[3,4-c]pyrazole;
3-(4-Chlorophenyl)-2-(2-methoxy-4-methylphenyl)-5-(methylsulfonyl)-2,4,5,6-tetrahydropyrrolo[3,4-c]pyrazole;
3-(4-Chlorophenyl)-2-(2-methoxy-4-methylphenyl)-5-[(1-methylethyl)sulfonyl]-2,4,5,6-tetrahydropyrrolo[3,4-c]pyrazole;
3-(4-Chlorophenyl)-2-(2-methoxy-4-methylphenyl)-5-[(1-methylbutyl)sulfonyl]-2,4,5,6-tetrahydropyrrolo[3,4-c]pyrazole;
3-(4-Chlorophenyl)-2-(2-methoxy-4-methylphenyl)-5-[(4-methylpiperidin-1-yl)sulfonyl]-2,4,5,6-tetrahydropyrrolo[3,4-c]pyrazole;
3-(4-Chlorophenyl)-2-(2-fluoro-4-methoxyphenyl)-5-(methylsulfonyl)-2,4,5,6-tetrahydropyrrolo[3,4-c]pyrazole;

3-(4-Chlorophenyl)-2-(2-fluoro-4-methoxyphenyl)-5-[(1-methylethyl)sulfonyl]-2,4,5,6-tetrahydropyrrolo[3,4-c]pyrazole;

3-(4-Chlorophenyl)-2-(2-fluoro-4-methoxyphenyl)-5-[(4-methylpiperidin-1-yl)sulfonyl]-2,4,5,6-tetrahydropyrrolo[3,4-c]pyrazole;

2-(1,3-Benzodioxol-4-yl)-3-(4-chlorophenyl)-5-[(1-methylethyl)sulfonyl]-2,4,5,6-tetrahydropyrrolo[3,4-c]pyrazole;

2-(1,3-Benzodioxol-4-yl)-3-(4-chlorophenyl)-5-[(2-methylpropyl)sulfonyl]-2,4,5,6-tetrahydropyrrolo[3,4-c]pyrazole;

2-(1,3-Benzodioxol-4-yl)-3-(4-chlorophenyl)-5-[(4-methylpiperidin-1-yl)sulfonyl]-2,4,5,6-tetrahydropyrrolo[3,4-c]pyrazole;

3-(4-Chlorophenyl)-2-(2,3-dihydro-1-benzofuran-7-yl)-5-[(1-methylethyl)sulfonyl]-2,4,5,6-tetrahydropyrrolo[3,4-c]pyrazole;

3-(4-Chlorophenyl)-2-(2,3-dihydro-1-benzofuran-7-yl)-5-[(2-methylpropyl)sulfonyl]-2,4,5,6-tetrahydropyrrolo[3,4-c]pyrazole;

3-(4-Chlorophenyl)-2-(2,3-dihydro-1-benzofuran-7-yl)-5-[(4-methylpiperidin-1-yl)sulfonyl]-2,4,5,6-tetrahydropyrrolo[3,4-c]pyrazole 3-(4-Chlorophenyl)-5-[(3,5-dimethylisoxazol-4-yl)sulfonyl]-2-(2-methoxyphenyl)-2,4,5,6-tetrahydropyrrolo[3,4-c]pyrazole;

2-[3-(4-Chlorophenyl)-5-[(1-methylethyl)sulfonyl]-5,6-dihydropyrrolo[3,4-c]pyrazol-2(4H)-yl]-N,N-dimethylaniline;

2-[3-(4-Chlorophenyl)-5-(ethylsulfonyl)-5,6-dihydropyrrolo[3,4-c]pyrazol-2(4H)-yl]-N,N-dimethylaniline;

3-(4-Chlorophenyl)-N,N-dimethyl-2-[2-(2,2,2-trifluoroethoxy)phenyl]-2,6-dihydropyrrolo[3,4-c]pyrazole-5(4H)-sulfonamide;

2-(2-tert-Butoxyphenyl)-3-(4-chlorophenyl)-N,N-dimethyl-2,6-dihydropyrrolo[3,4-c]pyrazole-5(4H)-sulfonamide;

3-(6-Chloropyridin-3-yl)-2-(2-methoxyphenyl)-5-[(1-methylethyl)sulfonyl]-2,4,5,6-tetrahydropyrrolo[3,4-c]pyrazole;

3-{2-(2-Methoxyphenyl)-5-[(1-methylethyl)sulfonyl]-2,4,5,6-tetrahydropyrrolo[3,4-c]pyrazol-3-yl}quinoline;

2-(2-Methoxyphenyl)-5-[(1-methylethyl)sulfonyl]-3-(6-methylpyridin-3-yl)-2,4,5,6-tetrahydropyrrolo[3,4-c]pyrazole;

3-(4-Chlorophenyl)-2-[2-(2,2-difluoroethoxy)phenyl]-N,N-dimethyl-2,6-dihydropyrrolo[3,4-c]pyrazole-5(4H)-sulfonamide;

2-(2-Methoxyphenyl)-3-[6-(1-methylethoxy)pyridin-3-yl]-5-[(1-methylethyl)sulfonyl]-2,4,5,6-tetrahydropyrrolo[3,4-c]pyrazole;

2-(2-Methoxyphenyl)-3-(6-methoxypyridin-3-O-5-[(1-methylethyl)sulfonyl]-2,4,5,6-tetrahydropyrrolo[3,4-c]pyrazole;

or a pharmaceutically acceptable salt form thereof.

15. A pharmaceutical composition comprising a compound of claim 1 or 14 and at least one of a pharmaceutically acceptable carrier, a pharmaceutically acceptable excipient, and a pharmaceutically acceptable diluent.

16. A pharmaceutical composition of claim 15, wherein the composition is a solid oral dosage form.

17. A pharmaceutical composition of claim 15, wherein the composition is a syrup, an elixir or a suspension.

\* \* \* \* \*